United States Patent
Leimer et al.

(10) Patent No.: US 10,253,213 B2
(45) Date of Patent: Apr. 9, 2019

(54) SILK PROTEIN COATINGS

(71) Applicant: AMSILK GMBH, Planegg/Martinsried (DE)

(72) Inventors: Axel H. Leimer, Frankfurt am Main (DE); Lin Romer, Munich (DE)

(73) Assignee: Amsilk GmbH, Planegg/Martinsried (DE)

( * ) Notice: Subject to any disclaimer, the term of this patent is extended or adjusted under 35 U.S.C. 154(b) by 0 days.

(21) Appl. No.: 14/958,775

(22) Filed: Dec. 3, 2015

(65) Prior Publication Data

US 2016/0280960 A1    Sep. 29, 2016

Related U.S. Application Data

(62) Division of application No. 13/514,265, filed as application No. PCT/EP2010/007440 on Dec. 7, 2010, now Pat. No. 9,217,017.

(60) Provisional application No. 61/267,596, filed on Dec. 8, 2009.

(30) Foreign Application Priority Data

Dec. 8, 2009 (EP) .................................... 09015193

(51) Int. Cl.
| | | |
|---|---|---|
| C07K 14/435 | (2006.01) | |
| C09D 189/00 | (2006.01) | |
| D06M 15/15 | (2006.01) | |
| D06M 23/10 | (2006.01) | |
| C03C 17/28 | (2006.01) | |
| C04B 41/48 | (2006.01) | |
| C08J 7/04 | (2006.01) | |
| C23C 2/04 | (2006.01) | |

(52) U.S. Cl.
CPC ............ *C09D 189/00* (2013.01); *C03C 17/28* (2013.01); *C04B 41/4807* (2013.01); *C07K 14/43518* (2013.01); *C08J 7/04* (2013.01); *C23C 2/04* (2013.01); *D06M 15/15* (2013.01); *D06M 23/10* (2013.01); *C07K 2319/00* (2013.01); *C07K 2319/60* (2013.01); *C08J 2323/06* (2013.01); *C08J 2323/12* (2013.01); *C08J 2327/18* (2013.01); *C08J 2367/03* (2013.01); *C08J 2377/00* (2013.01); *C08J 2489/00* (2013.01); *Y10T 428/2933* (2015.01); *Y10T 442/20* (2015.04)

(58) Field of Classification Search
None
See application file for complete search history.

(56) References Cited

U.S. PATENT DOCUMENTS

| | | | | |
|---|---|---|---|---|
| 5,695,777 A | * | 12/1997 | Donovan | A61F 13/023 424/443 |
| 6,497,893 B1 | * | 12/2002 | Everhart | A61K 8/0208 424/1.69 |
| 7,060,260 B2 | * | 6/2006 | Fahnestock | A61K 8/64 424/401 |
| 2004/0102614 A1 | * | 5/2004 | Islam | D01F 4/00 530/353 |
| 2004/0132978 A1 | * | 7/2004 | Fahnestock | C07K 14/43518 530/353 |
| 2009/0123967 A1 | * | 5/2009 | Scheibel | B82Y 5/00 435/69.1 |
| 2014/0113144 A1 | | 4/2014 | Loth et al. | |

FOREIGN PATENT DOCUMENTS

| | | | | |
|---|---|---|---|---|
| EP | 0230702 A1 | * | 8/1987 | ....... C07K 14/43586 |
| WO | 2005/120622 A2 | | 12/2005 | |
| WO | 2006/008163 A2 | | 1/2006 | |
| WO | 2007/025719 A1 | | 3/2007 | |
| WO | WO-2007025719 A1 | * | 3/2007 | ............... B82Y 5/00 |
| WO | WO 2007025719 A1 | * | 3/2007 | ............... B82Y 5/00 |
| WO | 2007/128378 A1 | | 11/2007 | |
| WO | 2008/083908 A1 | | 7/2008 | |
| WO | WO 2008/083908 A1 | * | 7/2008 | |
| WO | WO-2008083908 A1 | * | 7/2008 | ............. B32B 27/12 |
| WO | 2011/069643 A2 | | 6/2011 | |

OTHER PUBLICATIONS

Scheibel, Spider silks: recombinant synthesis, assembly, spinning, and engineering of synthetic proteins, Microbial Cell Factories 2004, 3:14, 2004.*
MITnews, "MIT lab works to mimic spider silk", Apr. 18, 2003.*
http://www.chm.bris.ac.uk/motm/spider/page3.htm; obtained Apr. 14, 2014, pp. 1-2.*
Lee et al., "Application of Silk Sericin to Finishing of Synthetic Fabrics", Sen'i Gakkaishi, 2005, p. 9-15 (Year: 2005).*
Accession No. A24713; Sericin-silkworm (fragment), 1993; p. 1 (Year: 1993).*
Molecular Probes, Inc., FluoReporter® Texas Red®—X Protein Labeling Kit (F-6162), 2001, pp. 1-3 (Year: 2001).*
Huemmerich et al., "Primary Structure Elements of Spider Dragline Silks and Their Contribution to Protein Solubility", Biochemistry, 2004, pp. 13604-13612 (Year: 2004).*
EP 07100223.2, 2007 Certified Priority Document; pp. 1-27 (Year: 2007).*
English Translation of Office Action dated Nov. 10, 2014 from corresponding Japanese application No. JP2012-542392.
Hardy, et al., "Polymeric materials based on silk proteins," *Polymer*, vol. 49(20), pp. 4309-4327 (2008).

(Continued)

*Primary Examiner* — Lianko G Garyu
(74) *Attorney, Agent, or Firm* — Kilpatrick Townsend & Stockton LLP

(57) ABSTRACT

The present invention relates to a method for coating an inert or naturally occurring material with a silk polypeptide. It further relates to a coated inert or naturally occurring material obtainable by said method and to uses thereof. It also relates to products comprising said coated material.

24 Claims, 8 Drawing Sheets

Specification includes a Sequence Listing.

(56) References Cited

OTHER PUBLICATIONS

Romer, et al., "The elaborate structure of spider silk," *Prion*, vol. 2(4), pp. 154-161 (2008).
Scheibel, "Spider silks: recombinant synthesis, assembly, spinning, and engineering of synthetic proteins," *Microbial Cell Factories*, vol. 3(14), 10 pages. (2004).
Database WPI, Week 200433, Thomson Scientific, London, GB, XP-002609431, AN 2004-350223 and JP 2003 171874, 2 pages (Jun. 20, 2003).
Database WPI, Week 200361, Thomson Scientific, London, GB, XP-002609432, AN 2003-638858 and JP 2002 363861, 3 pages (Dec. 18, 2002).
Database WPI, Week 200346, Thomson Scientific, London, GB, XP-002609433, AN 2003-493215 and WO 03/038181, 2 pages (May 8, 2003).
Database WPI, Week 199739, Thomson Scientific, London, GB, XP-002609434, AN 1997-420780 and JP 9 188972, 2 pages (Jul. 22, 1997).
Database WPI, Week 199316, Thomson Scientific, London, GB, XP-002609435, AN 1993-131620 and JP 5 071073, 2 pages (Mar. 23, 1993).
International Search Report for International Application No. PCT/EP2010/007440, 9 pages, dated Jun. 21, 2012.
Office Action issued by the European Patent Office for European Application No. 10793159.4, 3 pages, dated Apr. 12, 2013.
Patient Information and Consent to Breast Implantation, Annex II of MEDDEV 2 5/6-rev.1 (Jul. 1998).
MITnews, "MIT lab works to mimic spider silk," Apr. 18, 2013.
Scheibel, "Spider silks: recombinant synthesis, assembly, spinning, and engineering of synthetic proteins," Microbial Cell Factories 2004, 3:14, 20014.
English translation of Office Action dated Nov. 10, 2014 from corresponding Japanese application, JP2012-542392.
Anderson et al., :Bioactive Silk-Like Protein Polymer Films on Silicon Devices, Materials Research Society Symp. Proc. vol. 330, 1994, pp. 171-177.
Sano, "Process in the Development of Contact Lens Materials," Journal of Japan Contact Lens Society, vol. 50, 2008, 23 pages.

\* cited by examiner untreated	coated fabric

A    B

SILK PROTEIN COATINGS

The present invention relates to a method for coating an inert or naturally occurring material with a silk polypeptide. It further relates to a coated inert or naturally occurring material obtainable by said method and to uses thereof. The present invention also relates to products comprising said coated material.

BACKGROUND OF THE INVENTION

Spider silks are protein polymers that display extraordinary physical properties. Among the different types of spider silks, draglines are most intensely studied. Dragline-silks are utilized by orb weaving spiders to build frame and radii of their webs and as lifelines. For both purposes high tensile strength and elasticity are required. The combination of such properties results in a toughness that is higher than that of most other known materials. The dragline silk of *Araneus diadematus*, for example, demonstrates high tensile strength of 1.9 Gpa approximately equivalent to that of steel (1.3 Gpa) and aramid fibers.

Systems for the recombinant production of spider silk proteins in *E. coli* have been developed earlier (WO 2006/008163, WO 2006/002827). As an example, it is referred to WO 2006/008163 (claiming priority of U.S. provisional application No. 60/590,196). In this expression system, single building blocks (=modules) can be varied freely and can thus be adapted to the requirements of the specific case. Modules of this type are disclosed also in Hummerich, D., Helsen, C. W., Oschmann, J., Rudolph, R. & Scheibel, T. (2004): "Primary structure elements of dragline silks and their contribution to protein solubility and assembly, Biochemistry 43, 13604-13612". Further modules are described in WO 2007/025719. It is known from nature that spider silk proteins can be processed into threads. Spiders are experts in using different types of proteins to form silk threads and cobwebs. Technical processes to transform spider silk proteins into threads have been described, for example, in WO 2007/031301.

Synthetic or inorganic materials, e.g. synthetic or inorganic fibers, have been important for the industry for decades. Among these, the aramid thread kevlar, for example, is five times stronger than steel on an equal weight basis, yet, at the same time is lightweight. It also shows low electrical conductivity and has a very high chemical resistance—it is inert. On the one hand, this condition is desired, e.g. for protective clothing. On the other hand, however, aramid threads are very difficult to modify after production. It is nearly impossible to efficiently dye aramid threads or to attach molecules to the surface of aramid threads. Aramid threads are also only slightly wettable. This is also true for other inert synthetic or inorganic materials—they have a high chemical resistance, are only slightly wettable and can not be modified after polymerization under mild conditions, i.e. under low temperatures and without the use of toxic solvents. Common coatings either do not stick well to the surface of inert synthetic or inorganic materials, e.g. inert synthetic or inorganic fibers, and common coatings are not very durable or have to be applied under harsh conditions, i.e. high temperatures and/or toxic solvents.

Thus, there is a need for novel, suitable methods to modify inert synthetic or inorganic materials, e.g. inert synthetic or inorganic threads, after production, preferably at low temperatures and without the use of toxic solvents.

The inventors of the present invention have surprisingly found that the use of silk polypeptides as coating materials provides a highly efficient coating under mildest conditions and enables the manufacture of silk coated inert synthetic or inorganic materials tailored for specific applications. Up to now, very harsh conditions (if at all), like plasma treatment, were necessary to alter inert synthetic or inorganic materials, e.g. inert synthetic or inorganic fibers. There is also no method of coating inert synthetic or inorganic material available employing silk polypeptides, and, more importantly, no one thought about coating existing inert synthetic or inorganic fibers with a layer of pure silk—as this seemed completely impossible so far.

The inventive coating allows attachment of molecules under mild conditions, i.e. under low temperatures and without the use of toxic solvents, to inert synthetic or inorganic materials. In the medical technology, for example, agents, such as pharmaceutical agents, can be efficiently coupled to silk covered inert materials under non-destroying conditions.

In addition, inert synthetic or inorganic materials show several limitations. Most inert synthetic or inorganic materials, e.g. inert synthetic fibers such as aramid fibers or carbon fibers, have an non-desirable surface feel in comparison to natural fibers like, for example, insect silk. This means that most inert synthetic or inorganic materials are harsh, rough and brittle and, therefore, not pleasurable to touch. On the other hand, insect silk fibers share not the characteristics of inert synthetic or inorganic fibers and are often much more expensive.

Therefore, there is a need for novel inert synthetic or inorganic materials having an improved surface feel, i.e. improved haptic.

The inventors of the present invention have surprisingly found that silk coated inert synthetic or inorganic materials, e.g. silk coated aramid or carbon fibers, combine the advantages of inert synthetic or inorganic materials and the advantages of natural materials. Silk coated inert synthetic or inorganic materials have an improved surface feel (haptic) which renders these materials more pleasurable to touch. This effect is accompanied by an optical shine caused by the silk surface, which is more appealing than the dull appearance of aramid fibers or the black surface of carbon fibers. As an example, a kevlar fabric is suboptimal for applications in the near vicinity of or at the skin due to the rough and displeasing surface feel. Silk coated kevlar fabrics, however, are comfortable.

The industry is also constantly aiming to improve naturally occurring materials, such as cotton or wool, to exhibit novel and significantly improved physical, chemical and biological properties and functionalities. Furthermore, for textile industry it is desirable to provide naturally occurring materials, such as cotton or wool, with improved strength, elasticity, bending rigidity and/or resistance to motion while retaining air permeability and wearing comfort.

The inventors of the present invention have surprisingly found that the use of silk polypeptides provides a highly efficient coating reaction which enables the production of coated naturally occurring material having the desired properties mentioned above.

The inventive coating reaction using silk polypeptides also allows the effective attachment of molecules to naturally occurring materials to produce materials tailored for specific applications, e.g. coated textiles, clothing, and textiles for footwear having highly active surfaces providing UV-blocking, antimicrobial and self-cleaning properties.

SUMMARY OF THE INVENTION

In a first aspect, the present invention provides a method of coating an inert or naturally occurring material with a silk polypeptide which comprises the steps of:

i) providing a solution which comprises at least one silk polypeptide comprising at least two identical repetitive units and a solvent, and
ii) applying the solution on an inert material or on a naturally occurring material and thereby coating the inert material or the natural occurring material with the silk polypeptide.

In a second aspect, the present invention provides a coated inert or naturally occurring material obtainable by the method of the first aspect.

In a third aspect, the present invention provides products comprising the coated material of the second aspect.

In a fourth aspect, the present invention relates to the use of the coated inert or naturally occurring material of the second aspect.

In a fifth aspect, the present invention relates to the use of a silk polypeptide to dye inert materials. This summary of the invention does not necessarily describe all features of the invention.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise herein, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

As used in this specification and the appended claims, the singular forms "a", "an", and "the" include plural referents, unless the content clearly dictates otherwise.

Residues in two or more polypeptides are said to "correspond" to each other if the residues occupy an analogous position in the polypeptide structures. It is well known in the art that analogous positions in two or more polypeptides can be determined by aligning the polypeptide sequences based on amino acid sequence or structural similarities. Such alignment tools are well known to the person skilled in the art and can be, for example, obtained on the World Wide Web, e.g., ClustalW (www.ebi.ac.uk/clustalw) or Align (http://www.ebi.ac.uk/emboss/align/index.html) using standard settings, preferably for Align EMBOSS: needle, Matrix: Blosum62, Gap Open 10.0, Gap Extend 0.5.

In the context of the present invention, the term "inert material" refers to a material which has a high chemical resistance, is slightly or not wettable and/or cannot be modified after polymerization under mild conditions, i.e. under low temperatures and without the use of toxic solvents.

The term "synthetic material" as used in the context of the present invention refers to a material that has been manufactured or otherwise created by human beings, as opposed to those occurring in nature. The word "synthetic" also means artificially put together in the context of the present invention.

The term "inorganic material" as used in the context of the present invention refers to a material that does not contain hydrocarbon as the principal element (excepting carbonates, cyanides, and cyanates), that is, matter other than plant or animal, i.e. not of biological origin.

The term "naturally occurring material" as used in the context of the present invention refers to a material which exists in nature, which may, however, be modified and further processed, e.g. by bleaching, washing, stretching, spinning etc., as long as the modification does not significantly alter the polymer backbone of the material.

In the context of the present invention, the term "coating" refers to a covering that is applied to the inert or naturally occurring material to be coated. Preferably, said "coating" completely covers or surrounds the inert or naturally occurring material. It is preferred that the "coating" has a thickness of between 1 nm and 50 µm, preferably 40 nm and 50 µm, more preferably between 0.5 µm and 10 µm and most preferably between 1.0 µm and 5 µm.

Unless otherwise indicated, the terms "polypeptide" and "protein" are used interchangeably herein and mean any peptide-linked chain of amino acids, regardless of length or post-translational modification.

In the context of the present invention, the term "silk polypeptide" refers to a silk polypeptide or protein (it is noted that, unless otherwise indicated, these two terms, as used herein, are interchangeable) that is expressed in a recombinant (e.g. microbial, insect, plant or mammalian) expression system, i.e. separated from its natural milieu, (recombinant silk polypeptide or protein), or is harvested from natural sources (e.g. spider, silk worm, mussel, or fly larvae). Preferably, the "silk polypeptide" is isolated or purified. In particular, a "purified silk polypeptide" or an "isolated silk polypeptide" is free or substantially free of cellular material or other contaminating proteins from the cell or tissue source from which the protein is isolated or derived. The language "substantially free of cellular material" includes preparations of a silk polypeptide in which the silk polypeptide is separated from cellular components of the cells from which it is recombinantly produced. Thus, a silk polypeptide that is substantially free of cellular material includes preparations of silk polypeptides having less than about 30%, 20%, 10%, 5% or 1% (by dry weight) of contaminating protein.

A "silk polypeptide" as used in the context of the present invention further refers to a polypeptide with an amino acid sequence which comprises or consists of at least 50%, 60%, 65%, 70%, 75%, 80%, 85%, 90%, preferably at least 95% and most preferably 100% of multiple copies of one identical repetitive unit (e.g. $A_2$, $Q_6$, or $C_{16}$, wherein the items 2, 6, or 16 represent the number of repetitive units) or multiple copies of two or more different repetitive units (e.g. $(AQ)_{24}$, or $(AQ)_{12}C_{16}$). The silk polypeptide can further be modified by adding an artificial tag to facilitate the detection or purification of said protein (e.g. T7 tag).

The terms "repetitive unit" and "repeat unit" can interchangeable be used in the context of the present invention.

In the context of the present invention, the term "silk polypeptide" also refers to a silk polypeptide that comprises or consists of at least two identical repetitive units which comprise or consists of identical copies of amino acid sequences of naturally-occurring silk polypeptides or of variations of amino acid sequences of naturally-occurring silk polypeptides or of combinations of both.

In the context of the present invention, a "repetitive unit" refers to a region which corresponds in amino acid sequence to a region that comprises or consists of at least one peptide motif (e.g. AAAAAA (SEQ ID NO: 13) or GPGQQ (SEQ ID NO: 4)) that repetitively occurs within a naturally occurring silk polypeptide (e.g. MaSpI, ADF-3, ADF-4, or Flag) (i.e. identical amino acid sequence) or to an amino acid sequence substantially similar thereto (i.e. variational amino acid sequence). In this regard "substantially similar" means a degree of amino acid identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9%, preferably over the whole length of the respective reference naturally occurring amino acid sequence. A "repetitive unit" having an amino acid sequence which is "substantially similar" to a corresponding amino acid sequence within a naturally occurring silk polypeptide (i.e. wild-type repetitive unit) is also similar with respect to its functional properties, e.g. a silk polypeptide comprising the "substantially similar repetitive unit" still has the ability to form a coating on a synthetic or naturally occurring material, such as kevlar, wool, etc. Preferably, the silk polypeptide comprising the "substantially similar repetitive unit" is capable of forming a coating of a thickness of between 1 nm and 50 µm, preferably 40 nm and 50 µm, more preferably between 0.5 µm and 10 µm and most preferably between 1.0 µm and 5 µm as it is formable using a silk polypeptide comprising the respective reference (wild-type) repetitive unit. It is also preferred that the coating made from the silk polypeptide comprising the "substantially similar repetitive unit" has a similarly surface structure (surface undulation), e.g. roughness or porosity, compared to a coating made from a silk polypeptide comprising the respective reference (wild-type) repetitive unit. It is particularly preferred that the coating made from the silk polypeptide comprising the "substantially similar repetitive unit" exhibits a surface structure and a thickness similarly to a coating made from a silk polypeptide comprising the respective reference (wild-type) repetitive unit. The skilled person can readily assess the thickness or the surface structure (surface undulation) of a coating using electronic-microscopy.

A "repetitive unit" having an amino acid sequence which is "identical" to the amino acid sequence of a naturally occurring silk polypeptide, for example, can be a portion of a silk polypeptide corresponding to one or more peptide motifs of MaSp I (SEQ ID NO: 43) MaSp II (SEQ ID NO: 44), ADF-3 (SEQ ID NO: 1) and/or ADF-4 (SEQ ID NO: 2). A "repetitive unit" having an amino acid sequence which is "substantially similar" to the amino acid sequence of a naturally occurring silk polypeptide, for example, can be a portion of a silk polypeptide corresponding to one or more peptide motifs of MaSpI (SEQ ID NO: 43) MaSpII (SEQ ID NO: 44), ADF-3 (SEQ ID NO: 1) and/or ADF-4 (SEQ ID NO: 2), but having one or more amino acid substitution at specific amino acid positions.

The "repetitive unit" does not include the non-repetitive hydrophilic amino acid domain generally thought to be present at the carboxyl terminus of naturally occurring silk polypeptides.

A "repetitive unit" according to the present invention further refers to an amino acid sequence with a length of 3 to 200 amino acids, or 5 to 150 amino acids, preferably with a length of 10 to 100 amino acids, or 15 to 80 amino acids and more preferably with a length of 18 to 60, or 20 to 40 amino acids. For example, the repetitive unit according to the present invention can have a length of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, or 200 amino acids. Most preferably, the repetitive unit according to the invention consists of 3, 4, 5, 6, 7, 8, 9, 10, 12, 15, 18, 20, 24, 27, 28, 30, 34, 35, or 39 amino acids.

In a first aspect, the present invention provides a method of coating an inert or naturally occurring material with a silk polypeptide which comprises, essentially consists of, or consists of the steps of:
  i) providing a solution which comprises at least one silk polypeptide comprising at least two identical repetitive units and a solvent, and
  ii) applying the solution on an inert material or on a naturally occurring material and thereby coating the inert material or the natural occurring material with the silk polypeptide.

The inventors of the present invention have surprisingly found that silk polypeptides stably adhere to existing inert materials such as synthetic inert materials or inorganic inert materials (e.g. polyaramid such as Kevlar, polytetrafluorethylene (Teflon), or carbon) without using harsh reaction conditions (i.e. applying of high temperatures and/or use of toxic solvents), but with using mild reaction conditions (i.e. low temperatures and without the use of toxic solvents). It was also surprising for the inventors that an inert material coated with a silk polypeptide according to the above mentioned method has an improved surface feel (i.e. improved haptic and/or smooth surface) compared to a non-coated inert material that renders said material more pleasurable to human touch. The inventors of the present invention have further surprisingly found that a naturally occurring material coated with a silk polypeptide according to the above mentioned method has an improved strength, elasticity, bending rigidity, improved surface feel (i.e. improved haptic) and/or resistance to motion while retaining air permeability and wearing comfort.

Preferably, the solution is applied using dip coating, spray coating and/or padding in the method of the present invention.

"Dip coating" means (i) immersing an inert material or a naturally occurring material into a tank containing at least one silk polypeptide solution as a coating material (ii) incubating an inert material or a naturally occurring material in the tank with the at least one silk polypeptide, e.g. for a period of between 0.1 sec to 10 min, (iii) removing a coated inert material or naturally occurring material from the solution, and (iv) allowing it to drain. The coated inert material or naturally occurring material can then (v) be dried, e.g. by force-drying, baking, using a heat chamber, radiation or a fan (at room temperature or at elevated temperatures). Dip coating allows the creation of a thin film coated inert material or naturally occurring material, e.g. along with the spin coating procedure. Spin coating is a procedure used to apply uniform thin films to a inert or naturally occurring material. In short, an excess amount of a solution is placed on said material, which is then rotated at a constant speed, preferably from 1 m/min to 10 m/s, in order to spread the silk polypeptide by centrifugal force. A machine used for spin coating is called a spin coater, or simply spinner. The method of dip coating is exemplified in Example V and illustrated in FIG. 1.

"Spray coating" means (i) the transfer of the solution comprising at least one silk polypeptide into a spray can or spraying device, (ii) the uniformly distribution of the solution comprising at least one silk polypeptide onto the inert material or the naturally occurring material and (iii) the drying of the coating, e.g. by force-drying, baking, using a heat chamber, radiation or a fan (at room temperature or at elevated temperatures). The method of spray coating is described in Example VI and illustrated in FIG. 1.

"Padding" means (i) immersing or soaking an inert material or a naturally occurring material into a solution containing at least one silk polypeptide as a coating material (ii) incubating an inert material or a naturally occurring material in the solution with the at least one silk polypeptide, e.g. for a period of between 0.1 sec to 10 min, (iii) removing a coated inert material or naturally occurring material from the solution, and conducting (iv) the coated inert material or naturally occurring material through a pair of rolls to squeeze out the excess of silk polypeptide (solution). The coated inert material or naturally occurring material can then (v) be dried, e.g. by force-drying, baking, using a heat chamber, radiation or a fan (at room temperature or at elevated temperatures).

The silk polypeptide used in the method of the present invention preferably consists of between 6 to 1500 amino acids, or between 200 to 1300 amino acids and most preferably between 250 to 1200 amino acids, or between 500 to 1000 amino acids.

Preferably, the silk polypeptide used in the method of the present invention comprises, essentially consists, or consists of between 2 to 80 repetitive units, between 3 to 80 repetitive units, or between 4 to 60 repetitive units, more preferably between 8 to 48 repetitive units, or between 10 to 40 repetitive units and most preferably between 16 to 32 repetitive units. For example, the silk polypeptide used in the method of the present invention can comprise or consists of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 repetitive units. Most preferably, the silk polypeptide comprises 4, 8, 12, 16, 24, 32 or 48 repetitive units. As mentioned above, at least two of the repetitive units comprised in the silk polypeptide used in the method of the present invention are identical repetitive units. Thus, the silk polypeptide used in the method of the present invention may comprise multiple copies of one identical repetitive unit (e.g. $A_2$ or $C_{16}$, wherein the items 2 or 6 represent the number of repetitive units) or multiple copies of two or more different repetitive units (e.g. $(AQ)_{24}$ or $(QAQ)_8$). For example, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 of the 80 repetitive units which may be comprised in the silk polypeptide used in the method of the present invention are identical repetitive units.

The silk polypeptide used in the method of the present invention can comprise or consist of an amino acid sequence of any silk polypeptide known to one skilled in the art. It is preferred that the silk polypeptide used in the method of the present invention comprises or consists of an amino acid sequence of an arthropod silk polypeptide, preferably of a spider silk polypeptide, or an insect silk polypeptide. The silk polypeptide used in the method of the present invention can also comprise or consist of an amino acid sequence of a mussel silk polypeptide.

It is preferred that the spider silk polypeptide comprises or consists of an amino acid sequence of a major ampullate gland polypeptide (MaSp), such as a dragline spider silk polypeptide, a minor ampullate gland polypeptide (MiSp), a flagelliform polypeptide, an aggregate spider silk polypeptide, an aciniform spider silk polypeptide or a pyriform spider silk polypeptide. Most preferably, the spider silk polypeptide comprises or consists of an amino acid sequence of a dragline spider silk polypeptide or a flagelliform spider silk polypeptide. It is generally preferred to select the amino acid sequence of the dragline polypeptide or flagelliform polypeptide of a dragline polypeptide or flagelliform polypeptide of orb-web spiders of Araneidae or Araneoids.

It is preferred that the insect silk polypeptide comprises or consists of an amino acid sequence of a silk polypeptide of Lepidoptera. More preferably, the insect silk polypeptide comprises or consists of an amino acid sequence of a silk polypeptide of Bombycidae, most preferably of *Bombyx mori*.

Preferably, the above mentioned silk polypeptides are recombinantly produced, i.e. are recombinant silk polypeptides. For example, the silk polypeptides used in the method of the present invention are recombinant spider silk polypeptides such as dragline spider silk polypeptides or flagelliform spider silk polypeptides, recombinant insect silk polypeptides, or recombinant mussel silk polypeptides.

In the context of the present invention, the term "solution" means any liquid mixture that contains silk polypeptides and a solvent and is amenable for coating.

The solution provided in the method of the present invention comprises at least one type of silk polypeptide. Preferably, the solution provided in the method of the present invention comprises 2, 3, 4, 5, 6, 7, 8, 9, or 10 different types of silk polypeptides, most preferably 2 different types of silk polypeptides. For example, the solution can comprise dragline spider silk polypeptides, which differ from each other with respect to their amino acid sequence.

The solution provided in the method of the present invention can also comprise dragline spider silk and flagelliform spider silk polypeptides which differ from each other with respect to their naturally origin. The dragline spider silk polypeptide is from the major ampullate gland, while the flagelliform polypeptide is from the flagelliform gland.

The repetitive unit of the silk polypeptide used in the method of the present invention can comprise or consist of an amino acid sequence of any region that comprises or consists of at least one peptide motif that repetitively occurs within a naturally occurring silk polypeptide known to one skilled in the art. Preferably, the repetitive unit of the silk polypeptide used in the method of the present invention comprises or consists of an amino acid sequence of a region that comprises or consists of at least one peptide motif that repetitively occurs within an arthropod silk polypeptide, more preferably within a spider silk polypeptide, or an insect silk polypeptide. The repetitive unit of the silk polypeptide used in the method of the present invention can also comprise or consist of an amino acid sequence of a region that comprises or consists of at least one peptide motif that repetitively occurs within a mussel silk polypeptide.

It is preferred that the spider silk repetitive unit comprises or consists of an amino acid sequence of a region that comprises or consists of at least one peptide motif that repetitively occurs within a naturally occurring major ampullate gland polypeptide (MaSp), such as a dragline spider silk polypeptide, a minor ampullate gland polypeptide (MiSp), a flagelliform polypeptide, an aggregate spider silk polypeptide, an aciniform spider silk polypeptide or a pyriform spider silk polypeptide. Most preferably, the repetitive unit comprises or consists of an amino acid sequence of a region that comprises or consists of at least one peptide motif that repetitively occurs within a naturally occurring dragline spider silk polypeptide or a flagelliform spider silk polypeptide.

It is preferred that the insect silk repetitive unit comprises or consists of an amino acid sequence of a region that comprises or consists of at least one peptide motif that repetitively occurs within a naturally occurring silk polypeptide of Lepidoptera. More preferably, the insect silk repetitive unit comprises or consists of an amino acid sequence of a region that comprises or consists of at least one peptide motif that repetitively occurs within a naturally occurring insect silk polypeptide of Bombycidae, most preferably of *Bombyx mori*.

The term "consensus sequence" as used in the context of the present invention refers to an amino acid sequence which contains amino acids which frequently occur in a certain position (e.g. "G") and wherein, other amino acids which are not further determined are replaced by the place holder "X".

Preferably, the silk polypeptide used in the method of the present invention comprises, essentially consists of, or consists of at least two identical repetitive units each comprising at least one, preferably one, consensus sequence selected from the group consisting of:

i) GPGXX (SEQ ID NO: 3), wherein X is any amino acid, preferably in each case independently selected from A, S, G, Y, P, and Q;
ii) GGX, wherein X is any amino acid, preferably in each case independently selected from Y, P, R, S, A, T, N and Q, more preferably in each case independently selected from Y, P and Q; and
iii) $A_x$, wherein x is an integer from 5 to 10.

It is also preferred that the silk polypeptide used in the method of the present invention comprises or consists of at least two identical repetitive units each comprising at least one, preferably one, amino acid sequence selected from the group consisting of: GGRPSDTYG (SEQ ID NO: 18) and GGRPSSSYG (SEQ ID NO: 19).

The iterated (peptide) motifs GPGXX (SEQ ID NO: 3) and GGX, i.e. glycine rich motifs, provide flexibility to the silk polypeptide and thus, to the thread formed from the silk protein containing said motifs. In detail, the iterated GPGXX (SEQ ID NO: 3) motif forms (3-turn spiral structures, which imparts elasticity to the silk polypeptide. Major ampullate and flagelliform silks both have a GPGXX (SEQ ID NO: 3) motif. The iterated GGX motif is associated with a helical structure having three amino acids per turn and is found in most spider silks. The GGX motif may provide additional elastic properties to the silk. The iterated polyalanine $A_x$ (peptide) motif forms a crystalline β-sheet structure that provides strength to the silk polypeptide. (WO 03/057727). The GGRPSDTYG (SEQ ID NO: 18) and GGRPSSSYG (SEQ ID NO: 19) (peptide) motifs have been selected from Resilin (WO 08/155304). Resilin is an elastomeric protein found in most arthropods (*arthropoda*). It is located in specialised regions of the cuticle, providing low stiffness and high strength (Elvin et al., Nature (473): 999-1002, 2005).

Thus, in a preferred embodiment of the present invention, the silk polypeptide comprises or consists of repetitive units each comprising at least one (e.g. 1, 2, 3, 4, 5, 6, 7, 8, or 9), preferably one, amino acid sequence selected from the group consisting of GPGAS (SEQ ID NO: 5), GPGSG (SEQ ID NO: 6), GPGGY (SEQ ID NO: 7), GPGGP (SEQ ID NO: 8), GPGGA (SEQ ID NO: 9), GPGQQ (SEQ ID NO: 4), GPGGG (SEQ ID NO: 10), GPGQG (SEQ ID NO: 40), and GPGGS (SEQ ID NO: 11). In another preferred embodiment of the present invention, the silk polypeptide comprises or consists of repetitive units each comprising at least one (e.g. 1, 2, 3, 4, 5, 8, 7, or 8), preferably one, amino acid sequence selected from the group consisting of GGY, GGP, GGA, GGR, GGS, GGT, GGN, and GGQ. In a further preferred embodiment of the present invention, the silk polypeptide comprises or consists of repetitive units each comprising at least one (e.g. 1, 2, 3, 4, 5, or 6), preferably one, amino acid sequence selected from the group consisting of AAAAA (SEQ ID NO: 12), AAAAAA (SEQ ID NO: 13), AAAAAAA (SEQ ID NO: 14), AAAAAAAA (SEQ ID NO: 15), AAAAAAAAA (SEQ ID NO: 16), and AAAAAAAAAA (SEQ ID NO: 17).

In another preferred embodiment of the invention, the silk polypeptide comprises or consists of repetitive units each comprising at least one (e.g. 1, 2, 3, 4, 5, 6, 7, 8, 9, 10, 11, 12, 13, 14, 15, 16, 17, 18, 19, 20, 21, 22, 23, 24, or 25), preferably one, amino acid sequence selected from the group consisting of GPGAS (SEQ ID NO: 5), GPGSG (SEQ ID NO: 6), GPGGY (SEQ ID NO: 7), GPGGP (SEQ ID NO: 8), GPGGA (SEQ ID NO: 9), GPGQQ (SEQ ID NO: 4), GPGGG (SEQ ID NO: 10), GPGQG (SEQ ID NO: 40), GPGGS (SEQ ID NO: 11), GGY, GGP, GGA, GGR, GGS, GGT, GGN, GGQ, AAAAA (SEQ ID NO: 12), AAAAAA (SEQ ID NO: 13), AAAAAAA (SEQ ID NO: 14), AAAAAAAA (SEQ ID NO: 15), AAAAAAAAA (SEQ ID NO: 16), AAAAAAAAAA (SEQ ID NO: 17), GGRPSDTYG (SEQ ID NO: 18) and GGRPSSSYG (SEQ ID NO: 19).

Most preferably, the silk polypeptide used in the method of the present invention comprises, essentially consists of, or consists of repetitive units, which comprise or consist of (i) GPGAS (SEQ ID NO: 5), AAAAAA (SEQ ID NO: 13), GGY, and GPGSG (SEQ ID NO: 6) as amino acid sequence, preferably in this order, (ii) AAAAAAAA (SEQ ID NO: 15), GPGGY (SEQ ID NO: 7), GPGGY (SEQ ID NO: 7), and GPGGP (SEQ ID NO: 8) as amino acid sequence, preferably in this order,
(iii) GPGQQ (SEQ ID NO: 4), GPGQQ (SEQ ID NO: 4), GPGQQ (SEQ ID NO: 4) and GPGQQ (SEQ ID NO: 4) as amino acid sequence,
(iv) GPGGA (SEQ ID NO: 9), GGP, GPGGA (SEQ ID NO: 9), GGP, GPGGA (SEQ ID NO: 9), and GGP as amino acid sequence, preferably in this order,
(v) AAAAAAAA (SEQ ID NO: 15), GPGQG (SEQ ID NO: 40), and GGR as amino acid sequence, preferably in this order,
(vi) AAAAAAAA (SEQ ID NO: 15), GPGGG (SEQ ID NO: 10), GGR, GGN, and GGR as amino acid sequence, preferably in this order,
(vii) GGA, GGA, GGA, GGS, GGA, and GGS as amino acid sequence, preferably in this order, and/or
(viii) GPGGA (SEQ ID NO: 9), GPGGY (SEQ ID NO: 7), GPGGS (SEQ ID NO: 11), GPGGY (SEQ ID NO: 7), GPGGS (SEQ ID NO: 11), and GPGGY (SEQ ID NO: 7) as amino acid sequence, preferably in this order.

It should be noted that at least two of the repetitive units comprised in the silk polypeptides mentioned above are identical repetitive units.

Preferably, the silk polypeptide used in the method of the present invention comprises, essentially consists of, or consists of between 2 to 80 repetitive units, between 3 to 80 repetitive units, or between 4 to 60 repetitive units, more preferably between 8 to 48 repetitive units, or between 10 to 40 repetitive units and most preferably between 16 to 32 repetitive units, i.e. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 repetitive units, each comprising at least one, preferably one, consensus sequence selected from the group consisting of:
i) GPGXX (SEQ ID NO: 3), wherein X is any amino acid, preferably in each case independently selected from A, S, G, Y, P, and Q;
ii) GGX, wherein X is any amino acid, preferably in each case independently selected from Y, P, R, S, A, T, N and Q, more preferably in each case independently selected from Y, P and Q; and
iii) $A_x$, wherein x is an integer from 5 to 10.

As mentioned above, at least two of the repetitive units comprised in the silk polypeptide used in the method of the present invention are identical repetitive units.

It is also preferred that the silk polypeptide used in the method of the present invention comprises or consists of between 2 to 80 repetitive units, between 3 to 80 repetitive units, or between 4 to 60 repetitive units, more preferably between 8 to 48 repetitive units, or between 10 to 40 repetitive units and most preferably between 16 to 32 repetitive units, each comprising at least one, preferably one, amino acid sequence selected from the group consisting of: GGRPSDTYG (SEQ ID NO: 18) and GGRPSSSYG (SEQ ID NO: 19).

Thus, the silk polypeptide used in the method of the present invention preferably comprises or consists of between 2 to 80 repetitive units, between 3 to 80 repetitive units, or between 4 to 60 repetitive units, more preferably between 8 to 48 repetitive units, or between 10 to 40 repetitive units and most preferably between 16 to 32 repetitive units, i.e. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 repetitive units, each comprising at least one (e.g. 1, 2, 3, 4, 5, 6, 7, 8, 9, 10, 11, 12, 13, 14, 15, 16, 17, 18, 19, 20, 21, 22, 23, 24, or 25), preferably one, amino acid sequence selected from the group consisting of GPGAS (SEQ ID NO: 5), GPGSG (SEQ ID NO: 6), GPGGY (SEQ ID NO: 7), GPGGP (SEQ ID NO: 8), GPGGA (SEQ ID NO: 9), GPGQQ (SEQ ID NO: 4), GPGQG (SEQ ID NO: 40), GPGGG (SEQ ID NO: 10), GPGGS (SEQ ID NO: 11), GGY, GGP, GGA, GGR, GGS, GGT, GGN, GGQ, AAAAA (SEQ ID NO: 12), AAAAAA (SEQ ID NO: 13), AAAAAAA (SEQ ID NO: 14), AAAAAAAA (SEQ ID NO: 15), AAAAAAAAA (SEQ ID NO: 16), AAAAAAAAAA (SEQ ID NO: 17), GGRPSDTYG (SEQ ID NO: 18) and GGRPSSSYG (SEQ ID NO: 19).

Most preferably, the silk polypeptide used in the method of the present invention comprises, essentially consists of, or consists of
(i) repetitive units which comprise or consist of GPGAS (SEQ ID NO: 5), AAAAAA (SEQ ID NO: 13), GGY, and GPGSG (SEQ ID NO: 6) as amino acid sequence, preferably in this order,
(ii) repetitive units which comprise or consist of AAAAAAAA (SEQ ID NO: 15), GPGGY (SEQ ID NO: 7), GPGGY (SEQ ID NO: 7), and GPGGP (SEQ ID NO: 8) as amino acid sequence, preferably in this order,
(iii) repetitive units which comprise or consist of GPGQQ (SEQ ID NO: 4), GPGQQ (SEQ ID NO: 4), GPGQQ (SEQ ID NO: 4) and GPGQQ (SEQ ID NO: 4) as amino acid sequence,
(iv) repetitive units which comprise or consist of GPGGA (SEQ ID NO: 9), GGP, GPGGA (SEQ ID NO: 9), GGP, GPGGA (SEQ ID NO: 9), and GGP as amino acid sequence, preferably in this order,
(v) repetitive units which comprise or consist of AAAAAAAA (SEQ ID NO: 15), GPGQG (SEQ ID NO: 40), and GGR as amino acid sequence, preferably in this order,
(vi) repetitive units which comprise or consist of AAAAAAAA (SEQ ID NO: 15), GPGGG (SEQ ID NO: 10), GGR, GGN, and GGR as amino acid sequence, preferably in this order,
(vii) repetitive units which comprise or consist of GGA, GGA, GGA, GGS, GGA, and GGS as amino acid sequence, preferably in this order, and/or
(viii) repetitive units which comprise or consist of GPGGA (SEQ ID NO: 9), GPGGY (SEQ ID NO: 7), GPGGS (SEQ ID NO: 11), GPGGY (SEQ ID NO: 7), GPGGS (SEQ ID NO: 11), and GPGGY (SEQ ID NO: 7) as amino acid sequence, preferably in this order.

It should be noted that at least two of the repetitive units comprised in the silk polypeptides mentioned above are identical repetitive units.

Preferably, the silk polypeptide used in the method of the present invention comprises, essentially consists of, or consists of
(i) $(GPGXX)_n$ (SEQ ID NO: 3) as a repetitive unit, wherein X is any amino acid, preferably in each case independently selected from A, S, G, Y, P, and Q and n is 2, 3, 4, 5, 6, 7, 8, or 9;
ii) $(GGX)_n$ as a repetitive unit, wherein X is any amino acid, preferably in each case independently selected from Y, P, R, S, A, T, N and Q, more preferably in each case independently selected from Y, P and Q, and n is 2, 3, 4, 5, 6, 7, or 8; and/or iii) $(A_x)_n$ as a repetitive unit, wherein x is an integer from 5 to 10 and n is 2, 3, 4, 5, 6, 7, 8, 9, or 10.

As mentioned above, at least two of the repetitive units comprised in the silk polypeptides used in the method of the present invention are identical repetitive units.

It is preferred that the repetitive units are independently selected from module A (SEQ ID NO: 20), module C (SEQ ID NO: 21), module Q (SEQ ID NO: 22), module K (SEQ ID NO: 23), module sp (SEQ ID NO: 24), module S (SEQ ID NO: 25), module R (SEQ ID NO: 26), module X (SEQ ID NO: 27), or module Y (SEQ ID NO: 28), or variants thereof (i.e. module A variants, module C variants, module Q variants, module K variants, module sp variants, module S variants, module R variants, module X variants or module Y variants). The modules A (SEQ ID NO: 20) and Q (SEQ ID NO: 22) are based on the amino acid sequence of ADF-3 of the spider *Araneus diadematus*. Module C (SEQ ID NO: 21) is based on the amino acid sequence of ADF-4 of the spider *Araneus diadematus*. The modules K (SEQ ID NO: 23), sp (SEQ ID NO: 24), X (SEQ ID NO: 27) and Y (SEQ ID NO: 28) are based on the amino acid sequence of the flagelliform protein FLAG of the spider *Nephila clavipes* (WO 2006/008163). The modules S (SEQ ID NO: 25) and R (SEQ ID NO: 26) are based on Resilin (*Arthropoda*) (WO 2008/155304).

Thus, in a preferred embodiment of the present invention, the repetitive units of the silk polypeptide consist of module A: GPYGPGASAAAAAAGGYGPGSGQQ (SEQ ID NO: 20), module C: GSSAAAAAAAASGPGGYGPENQGPS-GPGGYGPGGP (SEQ ID NO: 21), module Q: GPGQQG-PGQQGPGQQGPGQQ (SEQ ID NO: 22), module K: GPG-GAGGPYGPGGAGGPYGPGGAGGPY (SEQ ID NO: 23), module sp: GGTTIIEDLDITIDGADGPITISEELTI (SEQ ID NO: 24), module S: PGSSAAAAAAAAS-GPGQGQGQGQGGRPSDTYG (SEQ ID NO: 25), module R: SAAAAAAAAGPGGGNGGRPSDTY-GAPGGGNGGRPSSSYG (SEQ ID NO: 26), module X: GGAGGAGGAGGSGGAGGS (SEQ ID NO: 27), or module Y: GPGGAGPGGYGPGGSGPGGYGPGGSGPGGY (SEQ ID NO: 28), or variants thereof.

Preferably, the silk polypeptide used in the method of the present invention comprises, essentially consists of, or consists of between 2 to 80 repetitive units, between 3 to 80 repetitive units, or between 4 to 60 repetitive units, more preferably between 8 to 48 repetitive units, or between 10 to 40 repetitive units and most preferably between 16 to 32 repetitive units, i.e. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 repetitive units, which are independently selected from module A (SEQ ID NO: 20), module C (SEQ ID NO: 21), module Q (SEQ ID NO: 22), module K (SEQ ID NO: 23), module sp (SEQ ID NO: 24), module S (SEQ ID NO: 25), module R (SEQ. ID NO: 26), module X (SEQ ID NO: 27) or module Y (SEQ ID NO: 28), or variants thereof (i.e. module A variants, module C variants, module Q variants, module K variants, module sp variants, module S variants, module R variants, module X variants or module Y variants). It should be noted that at least two of the repetitive units comprised in the silk polypeptide used in the method of the present invention are identical repetitive units (modules).

Thus, it is preferred that the silk polypeptide used in the method of the present invention comprises, essentially consists of, or consists of (i) repetitive unit(s) consisting of module A and/or repetitive unit(s) consisting of module A variants, (ii) repetitive unit(s) consisting of module C and/or repetitive unit(s) consisting of module C variants, (iii) repetitive unit(s) consisting of module Q and/or repetitive unit(s) consisting of module Q variants, (iv) (a) repetitive unit(s) consisting of module A and repetitive unit(s) consisting of module Q, (b) repetitive unit(s) consisting of module A and repetitive unit(s) consisting of module Q variants, (c) repetitive unit(s) consisting of module A variants and repetitive unit(s) consisting of module Q, (d) repetitive unit(s) consisting of module A variants and repetitive unit(s) consisting of module Q variants, (v) (a) repetitive unit(s) consisting of module A and repetitive unit(s) consisting of module C, (b) repetitive unit(s) consisting of module A and repetitive unit(s) consisting of module C variants, (c) repetitive unit(s) consisting of module A variants and repetitive unit(s) consisting of module C, (d) repetitive unit(s) consisting of module A variants and repetitive unit(s) consisting of module C variants, (vi) (a) repetitive unit(s) consisting of module C and repetitive unit(s) consisting of module Q, (b) repetitive unit(s) consisting of module C and repetitive unit(s) consisting of module Q variants, (c) repetitive unit(s) consisting of module C variants and repetitive unit(s) consisting of module Q, (d) repetitive unit(s) consisting of module C variants and repetitive unit(s) consisting of module Q variants, or (vii) (a) repetitive unit(s) consisting of module A, repetitive unit(s) consisting of module Q and repetitive unit(s) consisting of module C, (b) repetitive unit(s) consisting of module A, repetitive unit(s) consisting of module Q and repetitive unit(s) consisting of module C variants, (c) repetitive unit(s) consisting of module A, repetitive unit(s) consisting of module Q variants and repetitive unit(s) consisting of module C, (d) repetitive unit(s) consisting of module A variants, repetitive unit(s) consisting of module Q and repetitive unit(s) consisting of module C, (e) repetitive unit(s) consisting of module A, repetitive unit(s) consisting of module Q variants and repetitive unit(s) consisting of module C variants, (f) repetitive unit(s) consisting of module A variants, repetitive unit(s) consisting of module Q variants and repetitive unit(s) consisting of module C, (g) repetitive unit(s) consisting of module A variants, repetitive unit(s) consisting of module Q and repetitive unit(s) consisting of module C variants, (h) repetitive unit(s) consisting of module A variants, repetitive unit(s) consisting of module Q variants and repetitive unit(s) consisting of module C variants.

The modules A, C, Q, K, sp, S, R, X, Y or variants thereof (i.e. module A variants, module C variants, module Q variants, module K variants, module sp variants, module S variants, module R variants, module X variants or module Y variants) can also be combined with each other in any combination and in any number of each, i.e. module (repetitive unit) A can be combined with module (repetitive unit) Q (i.e. combination AQ), module (repetitive unit) C can be combined with module (repetitive unit) Q (i.e. combination CQ), module (repetitive unit) Q can be combined with module (repetitive unit) A and with module (repetitive unit) Q (i.e. combination QAQ), module (repetitive unit) A can be combined with module (repetitive unit) A and with module (repetitive unit) Q (i.e. combination AAQ), etc., under the proviso that the silk polypeptide used in the method of the present invention comprises or consists of at least two repetitive units which are identical. For example, the silk polypeptide used in the method of the present invention can comprise or consist of $A_n$, $(AA)_n$, $(AQ)_n$, $(QA)_n$, $Q_n$, $(QQ)_n$, $(QAQ)_n$, $(AQA)_n$, $C_n$, $(CC)_n$, $(CCC)_n$, $(CQ)_n$, $(QC)_n$, $(QCQ)_n$, $(CQC)_n$, $(AA)_nQ_n$, $(QQ)_nA_n$, $(AAA)_nQ_n$, $(QQQ)_nA_n$, $(AQQ)_n$, $(QQA)_n$, $K_n$, $sp_n$, $S_n$, $R_n$, $X_n$, $Y_n$, $(Ksp)_n$, $(spK)_n$, $(XY)_n$, $(YX)_n$, $(XX)_n$, $(YY)_n$, $(XXX)_n$, $(YYY)_n$, $(AX)_n$, $(XA)_n$, $(CX)_n$, $(XC)_n$, $(QX)_n$, $(XQ)_n$, $(YQ)_n$, $(QY)_n$, $(SS)_n$, $(SR)_n$, $(RS)_n$, or $(RR)_n$, wherein n is at least 2, preferably 4, 8, 9, 10, 12, 16, 20, 24, or 32. In case that the silk polypeptide consists of $(AQ)_{12}$, it is noted that module (repetitive unit) A is 12 times present and module (repetitive unit) Q is also 12 times present in the silk polypeptide and that, thus, the silk polypeptide consists of 24 modules (repetitive units). The arrangement of the modules (repeat units) of a silk polypeptide consisting of $(AQ)_{12}$ is as follows: AQAQAQAQAQAQAQAQAQAQAQAQ. Further, in case that the silk polypeptide of the modules (repeat units) of a silk polypeptide consists of $(QAQ)_8$, it is noted that module (repeat unit) A is 8 times present and module (repetitive unit) Q is 16 times present in the silk polypeptide and that, thus, the silk polypeptide consists of 24 modules (repetitive units). The arrangement of the modules (repeat units) of a silk polypeptide consisting of $(QAQ)_8$ is as follows: QAQQAQQAQQAQQAQQAQQAQQAQ.

The silk polypeptide used in the method of the present invention can also comprise or consist of $(A*Q)_n$, $(AQ*)_n$, $(A*Q*)_n$, $(Q*A)_n$, $(QA*)_n$, $(Q*A*)_n$, $(QAQ*)_n$, $(QA*Q)_n$, $(Q*AQ)_n$, $(QA*Q*)_n$, $(Q*A*Q)_n$, $(Q*AQ*)_n$, $(Q*A*Q*)_n$, $(AQA*)_n$, $(AQ*A)_n$, $(A*QA)_n$, $(AQ*A*)_n$, $(A*Q*A)_n$, $(A*QA*)_n$, $(A*Q*A*)_n$, wherein n is at least 2, preferably 4, 8, 9, 10, 12, 16, 20, 24, or 32 and wherein * indicates a module variant, i.e. module A or Q variant.

The terms "combined with each other" or "concatenated with each other" may mean in the context of the present invention that the modules (repetitive units) are directly combined or concatenated with each other or may mean in the context of the present invention that the modules (repetitive units) are combined or concatenated with each other via one or more spacer amino acids. In preferred embodiments, the modules (repetitive units) comprised in the silk polypeptide are directly combined or concatenated with each other. In other preferred embodiments, the modules (repetitive units) comprised in the silk polypeptide are combined or concatenated with each other via 1 to 25 or 1 to 20 spacer amino acids, more preferably via 1 to 15 or 1 to 10 spacer amino acids, and most preferably, via 1 to 5 spacer amino acids, i.e. via 1, 2, 3, 4, 5, 6, 7, 8, 9, 10, 11, 12, 13, 14, 15, 16, 17, 18, 19, 20, 21, 22, 23, 24, or 25 spacer amino acids. Said spacer amino acids may be any amino acids naturally occurring in proteins. Preferably, said spacer amino acid is not proline. It is preferred that the spacer amino acid(s) contain(s) charged groups. Preferably, the spacer amino acid(s) containing charged groups is (are) independently selected from the group consisting of aspartate, glutamate, histidine, and lysine. Said spacer amino acids should be amino acids which do not negatively affect the ability of a silk polypeptide to coat, preferably to uniformly coat, the inert or naturally occurring material, such as kevlar or wool. Further, said spacer amino acids should be amino acids which do not cause steric hindrance, e.g. amino acids having a small size such as lysine and cysteine.

In more preferred embodiments, the silk polypeptide comprises modules which are directly combined with each other and modules which are combined with each other via 1 to 25 or 1 to 20 spacer amino acids, more preferably via 1 to 15 or 1 to 10 spacer amino acids, and most preferably, via 1 to 5 spacer amino acids, i.e. via 2, 3, 4, 5, 6, 7, 8, 9, 10, 11, 12, 13, 14, 15, 16, 17, 18, 19, 20, 21, 22, 23, 24, or 25 spacer amino acids.

A module A, C, Q, K, sp, S, R, X or Y variant differs from the reference (wild-type) module A, C, Q, K, sp, S, R, X or Y from which it is derived by up to 1, 2, 3, 4, 5, 6, 7, 8, 9, 10, 11, 12, 13, 14, or 15 amino acid changes in the amino acid sequence (i.e. substitutions, additions, insertions, deletions, N-terminal truncations and/or C-terminal truncations). Such a module variant can alternatively or additionally be characterised by a certain degree of sequence identity to the reference (wild-type) module from which it is derived. Thus, a module A, C, Q, K, sp, S, R, X or Y variant has a sequence identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9% to the respective reference (wild-type) module A, C, Q, K, sp, S, R, X or Y. Preferably, the sequence identity is over a continuous stretch of at least 10, 15, 18, 20, 24, 27, 28, 30, 34, 35, or more amino acids, preferably over the whole length of the respective reference (wild-type) module A, C, Q, K, sp, S, R, X or Y.

It is particularly preferred that the sequence identity is at least 80% over the whole length, is at least 85% over the whole length, is at least 90% over the whole length, is at least 95% over the whole length, is at least 98% over the whole length, or is at least 99% over the whole length of the respective reference (wild-type) module A, C, Q, K, sp, S, R, X or Y. It is further particularly preferred that the sequence identity is at least 80% over a continuous stretch of at least 10, 15, 18, 20, 24, 28, or 30 amino acids, is at least 85% over a continuous stretch of at least 10, 15, 18, 20, 24, 28, or 30 amino acids, is at least 90% over a continuous stretch of at least 10, 15, 18, 20, 24, 28, or 30 amino acids, is at least 95% over a continuous stretch of at least 10, 15, 18, 20, 24, 28, or 30 amino acids, is at least 98% over a continuous stretch of at least 10, 15, 18, 20, 24, 28, or 30 amino acids, or is at least 99% over a continuous stretch of at least 10, 15, 18, 20, 24, 28, or 30 amino acids of the respective reference (wild-type) module A, C, Q, K, sp, S, R, X or Y.

A fragment (or deletion variant) of module A, C, Q, K, sp, S, R, X or Y has preferably a deletion of up to 1, 2, 3, 4, 5, 6, 7, 8, 9, 10, 11, 12, 13, 14, or 15 amino acids at its N-terminus and/or at its C-terminus. The deletion can also be internally.

Additionally, the module A, C, Q, K, sp, S, R, X or Y variant or fragment is only regarded as a module A, C, Q, K, sp, S, R, X or Y variant or fragment within the context of the present invention, if the modifications with respect to the amino acid sequence on which the variant or fragment is based do not negatively affect the ability of a silk polypeptide to coat, preferably to uniformly coat, the inert or naturally occurring material, such as kevlar or wool. Preferably, the silk polypeptide comprising the module A, C, Q, K, sp, S, R, X or Y variant or fragment is capable of forming a coating of a thickness of between 1 nm and 50 µm, preferably between 40 nm and 50 µm, more preferably between 0.5 µm and 10 µm and most preferably between 1.0 µm and 5 µm as it is formable using a silk polypeptide comprising the respective reference (wild-type) module A, C, Q, K, sp, S, R, X or Y. It is also preferred that the coating made from the silk polypeptide comprising the module A, C, Q, K, sp, S, R, X or Y variant or fragment has a similarly surface structure (surface undulation), e.g. roughness or porosity, compared to a coating made from a silk polypeptide comprising the respective reference (wild-type) module A, C, Q, K, sp, S, R, X or Y. It is particularly preferred that the coating made from the silk polypeptide comprising the module A, C, Q, K, sp, S, R, X or Y variant or fragment exhibits a surface structure and a thickness similarly to a coating made from a silk polypeptide comprising the respective reference (wild-type) module A, C, Q, K, sp, S, R, X or Y. The skilled person can readily assess the thickness or the surface structure (surface undulation) of a coating using electronic-microscopy.

Thus, in a preferred embodiment of the present invention the repetitive units are independently selected from module $A^C$ (SEQ ID NO: 29), module $A^K$ (SEQ ID NO: 30), module $C^C$ (SEQ ID NO: 31), module $C^{K1}$ (SEQ ID NO: 32), module $C^{K2}$ (SEQ ID NO: 33) or module $C^{KC}$ (SEQ ID NO: 34). The modules $A^C$ (SEQ ID NO: 29), $A^K$ (SEQ ID NO: 30), $C^C$ (SEQ ID NO: 31), $C^{K1}$ (SEQ ID NO: 32), $C^{K2}$ (SEQ ID NO: 33) and $C^{KC}$ (SEQ ID NO: 34) are variants of the module A which is based on the amino acid sequence of ADF-3 of the spider *Araneus diadematus* and of module C which is based on the amino acid sequence of ADF-4 of the spider *Araneus diadematus* (WO 2007/025719). In module $A^C$ (SEQ ID NO: 29) the amino acid S (serine) at position 21 has been replaced by the amino acid C (cysteine), in module $A^K$ (SEQ ID NO: 30) the amino acid S at position 21 has been replaced by the amino acid K (lysine), in module $C^C$ (SEQ ID NO: 31) the amino acid S at position 25 has been replaced by the amino acid 25 by C, in module $C^{K1}$ (SEQ ID NO: 32) the amino acid S at position 25 has been replaced by the amino acid K, in module $C^{K2}$ (SEQ ID NO: 33) the amino acid E (glutamate) at position 20 has been replaced by the amino acid K, and in module $C^{KC}$ (SEQ ID NO: 34) the amino acid E at position 20 has been replaced by the amino acid K and the amino acid S at position 25 has been replaced by the amino acid C (WO 2007/025719).

Preferably, the repetitive units in the silk polypeptide used in the method of the present invention consist of module $A^C$: GPYGPGASAAAAAAGGYGPGCGQQ (SEQ ID NO: 29), module $A^K$: GPYGPGASAAAAAAGGYGPGKGQQ (SEQ ID NO: 30), module $C^C$: GSSAAAAAAAASGPGGYG-PENQGPCGPGGYGPGGP (SEQ ID NO: 31), module $C^{K1}$: GSSAAAAAAAASGPGGYGPENQGPKGPGGYGPGGP (SEQ ID NO: 32), module $C^{K2}$: GSSAAAAAAAASGPG-GYGPKNQGPSGPGGYGPGGP (SEQ ID NO: 33), or module $C^{KC}$: GSSAAAAAAAASGPGGYGPKNQGPCG-PGGYGPGGP (SEQ ID NO: 34).

It is also preferred that the silk polypeptide used in the method of the present invention comprises, essentially consists of, or consists of between 2 to 80 repetitive units, between 3 to 80 repetitive units, or between 4 to 60 repetitive units, preferably between 8 to 48 repetitive units, or between 10 to 40 repetitive units and most preferably between 16 to 32 repetitive units, i.e. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 repetitive units, which are independently selected from module $A^C$ (SEQ ID NO: 29), module $A^K$ (SEQ ID NO: 30), module $C^C$ (SEQ ID NO: 31), module $C^{K1}$ (SEQ ID NO: 32), module $C^{K2}$ (SEQ ID NO: 33) or module $C^{KC}$ (SEQ ID NO: 34). It should be noted that at least two of the repetitive units comprised in the silk polypeptide used in the method of the present invention are identical repetitive units (modules).

For example, the silk polypeptide used in the method of the present invention can comprises or consists of the modules $C^C_4$, $C^C_8$, $C^C_{16}$, $C^C_{32}$, $A^C_5$, $A^C_8$, or $A^C_{10}$.

The modules $A^K$, $C^C$, $C^{K1}$, $C^{K2}$ and $C^{KC}$ can also be combined with each other, i.e. module (repetitive unit) $A^K$ can be combined with module (repetitive unit) $C^C$ (i.e. combination $A^K C^C$), module (repetitive unit) $C^{K1}$ can be combined with module (repetitive unit) $C^{K2}$ and with module (repetitive unit) $C^{KC}$ (i.e. combination $C^{K1}C^{K2}C^{KC}$), etc., under the proviso that the silk polypeptide used in the method of the present invention comprises or consists of at least two repetitive units which are identical. Thus, the silk polypeptide used in the method of the present invention can also comprise or consist of the modules $(A^K)_n$, $(C^C)_n$, $(C^{K1})_n$, $(C^{K2})_n$, $(C^{KC})_n$, $(A^K A^C)_n$, $(C^C C^C)_n$, $(C^{K1}C^{K2})_n$, $(C^{K2}C^{K1})_n$, $(C^{K1}C^{K2}C^{K1})_n$, $(C^{K2}C^{K1}C^{K2})_n$, $(C^{K1}C^{K2}C^{KC})_n$, $(C^{KC}C^{K2}C^{KC})_n$, or $(C^{KC}C^{K2}C^{K1})_n$, wherein n is at least 2, preferably 4, 5, 6, 7, 8, 10, 12, 16, or 20. The term "combined with each other" is defined above.

It is further preferred that the silk polypeptide used in the method of the present invention comprises, essentially consists of, or consists of between 2 to 80 repetitive units, between 3 to 80 repetitive units or between 4 to 60 repetitive units, preferably between 8 to 48 repetitive units, or between 10 to 40 repetitive units and most preferably between 16 to 32 repetitive units, i.e. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 repetitive units, which are independently selected from module A (SEQ ID NO: 20) or variants thereof, module C (SEQ ID NO: 21) or variants thereof, module Q (SEQ ID NO: 22) or variants thereof, module K (SEQ ID NO: 23) or variants thereof, module sp (SEQ ID NO: 24) or variants thereof, module S (SEQ ID NO: 25) or variants thereof, module R (SEQ ID NO: 26) or variants thereof, module X (SEQ ID NO: 27) or variants thereof, module Y (SEQ ID NO: 28) or variants thereof, module $A^C$ (SEQ ID NO: 29), module $A^K$ (SEQ ID NO: 30), module $C^C$ (SEQ ID NO: 31), module $C^{K1}$ (SEQ ID NO: 32), module $C^{K2}$ (SEQ ID NO: 33) or module $C^{KC}$ (SEQ ID NO: 34). Again, it should be noted that at least two of the repetitive units comprised in the silk polypeptide used in the method of the present invention are identical repetitive units (modules).

The modules $A^K$, $C^C$, $C^{K1}$, $C^{K2}$ and $C^{KC}$ can also be combined with the modules A, C, Q, K, sp, S, R, X or Y, i.e. module (repetitive unit) $A^K$ can be combined with module (repetitive unit) C (i.e. combination $A^K C$), or module (repetitive unit) $C^C$ can be combined with module (repetitive unit) C (i.e. combination $C^C C$), etc., under the proviso that the silk polypeptide used in the method of the present invention comprises or consists of at least two repetitive units which are identical. Thus, the silk polypeptide used in the method of the present invention can also comprise or consist of the modules $(AQA^K)_n$, $(QA^K)_n$, $(QA^K Q)_n$, $(A^K QA)_n$, $(A^K QA^K)_n$, $(CC^C)_n$, $(CC^C C)_n$, $(C^C CC^C)_n$, $(CC^C C^C)_n$, $(C^C Q)_n$, $(QC^C)_n$, $(QC^C Q)_n$, $(C^C QC)_n$, $(CQC^C)_n$, $(C^C QC^C)_n$, $(CC^{K1}C)_n$, $(C^{K1}C)_n$, $(C^{K1}CC)_n$, $(CC^{K1}C)_n$, $(C^{KC}C^{KC}C)_n$, $(CC^{KC}C^{KC})_n$, $(C^{KC}Q)_n$, $(QC^{KC})_n$, $(QC^{KC}Q)_n$, $(A^K C^{K1}Q)_n$, $(QC^{K2}A^K)_n$, or $(C^{K1}C^{K2}C)_n$, wherein n is at least 2, preferably 4, 5, 6, 7, 8, 10, 12, 16, or 20. The term "combined with each other" is defined above.

For example, the silk polypeptide used in the method of the present invention comprises or consists of the modules $C_{16}C^C$, $C^C C_{16}$, $C_8 C^C C_8$, $C_8 C^C_8$, $C^C_8 C_8$, $C_4 C^C_8 C_4$, $C^C_4 C_8 C^C_4$, $C^C (AQ)_{24}$, or $(AQ)_{24} C^C$.

The silk polypeptide used in the method of the present invention can further comprise at least one non-repetitive (NR) unit, i.e. 1, 2, 3, 4, 5, 6, or more NR units, preferably one NR unit. In the context of the present invention, the term "non-repetitive (NR) unit" refers to a region of amino acids present in a naturally occurring silk polypeptide that displays no obvious repetition pattern (non-repetitive unit or NR unit). Preferably, the amino acid sequence of the non-repetitive unit corresponds to a non-repetitive amino acid sequence of naturally occurring dragline polypeptides, preferably of ADF-3 (SEQ ID NO: 1) or ADF-4 (SEQ ID NO: 2), or to an amino acid sequence substantially similar thereto.

It is particularly preferred that the amino acid sequence of the non-repetitive unit corresponds to a non-repetitive carboxy terminal amino acid sequence of naturally occurring dragline polypeptides, preferably of ADF-3 (SEQ ID NO: 1) or ADF-4 (SEQ ID NO: 2), or to an amino acid sequence substantially similar thereto. More preferably, the amino acid sequence of the non-repetitive unit corresponds to a non-repetitive carboxy terminal amino acid sequence of ADF-3 (SEQ ID NO: 1) which comprises amino acids 513 through 636, or of ADF-4 (SEQ ID NO: 2) which comprises amino acids 302 through 410, or to an amino acid sequence substantially similar thereto.

In this regard "substantially similar" means a degree of amino acid identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9%, preferably over 20, 30, 40, 50, 60, 70, 80 or more amino acids, more preferably over the whole length of the respective reference non-repetitive (carboxy terminal) amino acid sequence of naturally occurring dragline polypeptides, preferably of ADF-3 (SEQ ID NO: 1) or ADF-4 (SEQ ID NO: 2).

A "non-repetitive unit" having an amino acid sequence which is "substantially similar" to a corresponding non-repetitive (carboxy terminal) amino acid sequence within a naturally occurring dragline polypeptide (i.e. wild-type non-repetitive (carboxy terminal) unit), preferably within ADF-3 (SEQ ID NO: 1) or ADF-4 (SEQ ID NO: 2), is also similar with respect to its functional properties, e.g. a silk polypeptide comprising the "substantially similar non-repetitive unit" still has the ability to form a coat on a synthetic or naturally occurring material, such as kevlar, wool, etc. Preferably, the silk polypeptide comprising the "substantially similar non-repetitive unit" is capable of forming a coating of a thickness of between 1 nm and 50 µm, preferably between 40 nm and 50 µm, more preferably between 0.5 µm and 10 µm and most preferably between 1.0 µm and 5 µm as it is formable using a silk polypeptide comprising the respective reference (wild-type) non-repetitive (carboxy terminal) unit. It is also preferred that the coating made from the silk polypeptide comprising the "substantially similar non-repetitive unit" has a similarly surface structure (surface undulation), e.g. roughness or porosity, compared to a coating made from a silk polypeptide comprising the respective reference (wild-type) non-repetitive (carboxy terminal) unit. It is particularly preferred that the coating made from the silk polypeptide comprising the "substantially similar repetitive unit" exhibits a surface structure and a thickness similarly to a coating made from a silk polypeptide comprising the respective reference (wild-type) non-repetitive (carboxy terminal) unit. The skilled person can readily assess the thickness or the surface structure (surface undulation) of a coating using electronic-microscopy.

Most preferably, the non-repetitive (NR) unit is NR3 (SEQ ID NO: 41) or variants thereof, or NR4 (SEQ ID NO: 42) or variants thereof. The NR3 (SEQ ID NO: 41) unit is based on the amino acid sequence of ADF-3 of the spider *Araneus diadematus* and the NR4 (SEQ ID NO: 42) unit is based on the amino acid sequence of ADF-4 of the spider *Araneus diadematus* (WO 2006/008163).

A NR3 or NR4 unit variant differs from the reference NR3 (SEQ ID NO: 41) or NR4 (SEQ ID NO: 42) unit from which it is derived by up to 1, 2, 3, 4, 5, 6, 7, 8, 9, 10, 11, 12, 13, 14, 15, 16, 17, 18, 19, 20, 25, or 30 amino acid changes in the amino acid sequence (i.e. exchanges, insertions, deletions, N-terminal truncations and/or C-terminal truncations). Such a NR3 or NR4 unit variant can alternatively or additionally be characterised by a certain degree of sequence identity to the reference NR3 or NR4 unit from which it is derived. Thus, a NR3 or NR4 unit variant has a sequence identity of at least 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9% to the respective reference NR3 or NR4 unit. Preferably, the sequence identity is over a continuous stretch of at least 10, 20, 30, 40, 50, 60, 70, 80, 90, or more amino acids, preferably over the whole length of the respective reference NR3 or NR4 unit.

It is particularly preferred that the sequence identity is at least 80% over the whole length, is at least 85% over the whole length, is at least 90% over the whole length, is at least 95% over the whole length, is at least 98% over the whole length, or is at least 99% over the whole length of the respective reference NR3 or NR4 unit. It is further particularly preferred that the sequence identity is at least 80% over a continuous stretch of at least 20, 30, 40, 50, 60, 70, or 80 amino acids, is at least 85% over a continuous stretch of at least 20, 30, 40, 50, 60, 70, or 80 amino acids, is at least 90% over a continuous stretch of at least 20, 30, 40, 50, 60, 70, or 80 amino acids, is at least 95% over a continuous stretch of at least 20, 30, 40, 50, 60, 70, or 80 amino acids, is at least 98% over a continuous stretch of at least 20, 30, 40, 50, 60, 70, or 80 amino acids, or is at least 99% over a continuous stretch of at least 20, 30, 40, 50, 60, 70, or 80 amino acids of the respective reference NR3 or NR4 unit.

A fragment (or deletion variant) of a NR3 or NR4 unit has preferably a deletion of up to 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, or 60 amino acids at its N-terminus and/or at its C-terminus. The deletion can also be internally.

Additionally, the NR3 or NR4 unit variant or fragment is only regarded as a NR3 or NR4 unit variant or fragment within the context of the present invention, if the modifications with respect to the amino acid sequence on which the variant or fragment is based do not negatively affect the ability of a silk polypeptide to coat, preferably to uniformly coat, the inert or naturally occurring material, such as kevlar or cotton. Preferably, the silk polypeptide comprising the NR3 or NR4 variant or fragment is capable of forming a coating of a thickness of between 1 nm and 50 µm, preferably between 40 nm and 50 µm, more preferably between 0.5 µm and 10 µm and most preferably between 1.0 µm and 5.0 µm as it is formable using a silk polypeptide comprising the respective reference NR3 or NR4 unit. It is also preferred that the coating made from the silk polypeptide comprising the NR3 or NR4 variant or fragment has a similarly surface structure (surface undulation), e.g. roughness or porosity, compared to a coating made from a silk polypeptide comprising the respective reference NR3 or NR4 unit. It is particularly preferred that the coating made from the silk polypeptide comprising the NR3 or NR4 unit variant or fragment exhibits a surface structure and a thickness similarly to a coating made from a silk polypeptide comprising the respective reference NR3 or NR4 unit. The skilled person can readily assess the thickness or the surface structure (surface undulation) of a coating using electronic-microscopy.

Alternatively, it can be tested whether the NR3 or NR4 unit variant or fragment still enables the polymerization and/or increases the solubility of a silk polypeptide wherein it is comprised. The skilled person in the art can readily assess whether a silk polypeptide comprising a NR3 or NR4 unit variant or fragment has the above mentioned functional properties like a silk polypeptide comprising the respective reference NR3 or NR4 unit. Suitable assays are well known to the person skilled in the art. For example, the polymerization of silk polypeptides comprising a NR3 or NR4 unit variant or fragment and the polymerization of silk polypeptides comprising the respective reference NR3 or NR4 unit can easily be visualized via native gel electrophoresis. The solubility of a silk polypeptide comprising a NR3 or NR4 unit variant or fragment and the solubility of a silk polypeptide comprising the respective reference NR3 or NR4 unit can simply be tested via saturation of said silk polypeptides in an aqueous solution. The results can finally be compared with each other.

Preferably, the silk polypeptide used in the method of the present invention is selected from the group consisting of ADF-3 (SEQ ID NO: 1) or variants thereof, ADF-4 (SEQ ID NO: 2) or variants thereof, MaSp I (SEQ ID NO: 43) or variants thereof, MaSp II (SEQ ID NO: 44) or variants thereof, $(C)_m$, $(C)_mNR_z$, $NR_z(C)_m$, $(AQ)_n$, $(AQ)_nNR_z$, $NR_z(AQ)_n$, $(QAQ)_o$, $NR_z(QAQ)_o$, $(QAQ)_oNR_z$, $Y_p$, $X_p$, and $K_p$, wherein m is an integer of 8 to 48 (i.e. 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48), n is an integer of 6 to 24 (i.e. 6, 7, 8, 9, 10, 11, 12, 13, 14, 15, 16, 17, 18, 19, 20, 21, 22, 23, or 24), o is an integer of 8 to 16 (i.e. 8, 9, 10, 11, 12, 13, 14, 15, or 16), p is an integer of 8 to 16 (i.e. 8, 9, 10, 11, 12, 13, 14, 15, or 16) and z is an integer of 1 to 3 (i.e. 1, 2, or 3) and NR stands for a non-repetitive unit. The above mentioned formulas are defined by one of the following: In the formula
(i) $(C)_m$, a "m" number of C modules, namely 8 to 48 C modules, represented by the amino acid sequence according to SEQ ID NO: 21, are combined with each other,
(ii) $(C)_mNR_z$, a "m" number of C modules, namely 8 to 48 C modules, represented by the amino acid sequence according to SEQ ID NO: 21, are combined with each other, wherein said C modules are further combined with a "z" number of non-repetitive (NR) units, namely 1 to 3 non-repetitive (NR) units, e.g. the non-repetitive (NR) units NR3 represented by the amino acid sequence according to SEQ ID NO: 41 or NR4 represented by the amino acid sequence according to SEQ ID NO: 42,
(iii) $NR_z(C)_m$, a "z" number of non-repetitive (NR) units, namely 1 to 3 non-repetitive (NR) units, e.g. the non-repetitive (NR) units NR3 represented by the amino acid sequence according to SEQ ID NO: 41 or NR4 represented by the amino acid sequence according to SEQ ID NO: 42, is present (z=1) or are combined with each other (z=2 or 3), wherein said non-repetitive (NR) unit(s) is (are) further combined with a "m" number of C modules, namely 8 to 48 C modules, represented by the amino acid sequence according to SEQ ID NO: 21,
(iv) $(AQ)_n$, a "n" number of A and Q module combinations, namely 6 to 24 A and Q module combinations, wherein module A is represented by the amino acid sequence according to SEQ ID NO: 20 and module Q is represented by the amino acid sequence according to SEQ ID NO: 22, are combined with each other,
(v) $(AQ)_nNR_z$, a "n" number of A and Q module combinations, namely 6 to 24 A and Q module combinations, wherein module A is represented by the amino acid sequence according to SEQ ID NO: 20 and module Q is represented by the amino acid sequence according to SEQ ID NO: 22, are combined with each other, and wherein said A and Q module combinations are further combined with a "z" number of non-repetitive (NR) units, namely 1 to 3 non-repetitive (NR) units, e.g. the non-repetitive (NR) units NR3 represented by the amino acid sequence according to SEQ ID NO: 41 or NR4 represented by the amino acid sequence according to SEQ ID NO: 42,
(vi) $NR_z(AQ)_n$, a "z" number of non-repetitive (NR) units, namely 1 to 3 non-repetitive (NR) units, e.g. the non-repetitive (NR) units NR3 represented by the amino acid sequence according to SEQ ID NO: 41 or NR4 represented by the amino acid sequence according to SEQ ID NO: 42, is present (z=1) or are combined with each other (z=2 or 3), wherein said non-repetitive (NR) unit(s) is (are) further combined with a "n" number of A and Q module combinations, namely 6 to 24 A and Q module combinations, wherein module A is represented by the amino acid sequence according to SEQ ID NO: 20 and module Q is represented by the amino acid sequence according to SEQ ID NO: 22,
(vii) $(QAQ)_o$, a "o" number of Q, A and Q module combinations, namely 8 to 16 Q, A and Q module combinations, wherein module Q is represented by an amino acid sequence according to SEQ ID NO: 22 and module A is represented by the amino acid sequence according to SEQ ID NO: 20, are combined with each other,
(viii) $(QAQ)_oNR_z$, a "o" number of Q, A and Q module combinations, namely 8 to 16 Q, A and Q module combinations, wherein module Q is represented by an amino acid sequence according to SEQ ID NO: 22 and module A is represented by the amino acid sequence according to SEQ ID NO: 20, are combined with each other, and wherein said Q, A and Q module combinations are further combined with a "z" number of non-repetitive (NR) units, namely 1 to 3 non-repetitive (NR) units, e.g. the non-repetitive (NR) units NR3 represented by the amino acid sequence according to SEQ ID NO: 41 or NR4 represented by the amino acid sequence according to SEQ ID NO: 42,
(ix) $NR_z(QAQ)_o$, a "z" number of non-repetitive (NR) units, namely 1 to 3 non-repetitive (NR) units, e.g. the non-repetitive (NR) units NR3 represented by the amino acid sequence according to SEQ ID NO: 41 or NR4 represented by the amino acid sequence according to SEQ ID NO: 42, is present (z=1) or are combined with each other (z=2 or 3), wherein said non-repetitive (NR) unit(s) is (are) further combined with a "o" number of Q, A and Q module combinations, namely 8 to 16 Q, A and Q module combinations, wherein module Q is represented by an amino acid sequence according to SEQ ID NO: 22 and module A is represented by the amino acid sequence according to SEQ ID NO: 20, (x) $Y_p$, a "p" number of Y modules, namely 8 to 16 Y modules, represented by the amino acid sequence according to SEQ ID NO: 28, are combined with each other, (xi) $X_p$, a "p" number of X modules, namely 8 to 16 X modules, represented by the amino acid sequence according to SEQ ID NO: 27, are combined with each other, and (xii) $K_m$ a "p" number of K modules, namely 8 to 16 K modules, represented by the amino acid sequence according to SEQ ID NO: 23, are combined with each other.

Most preferably, the silk polypeptide used in the method of the present invention is $C_{16}NR4$, $C_{32}NR4$, $(AQ)_{12}$, $(AQ)_{24}$, $(AQ)_{12}NR3$, $(AQ)_{24}NR3$, $C_{16}$, $C_{32}$, $Y_8$, $Y_{16}$, $X_8$, $X_{16}$, $K_8$, or $K_{16}$.

An ADF-3, ADF-4, MaSp I or MaSp II variant differs from the reference (wild-type) ADF-3 (SEQ ID NO: 1), ADF-4 (SEQ ID NO: 2), MaSp I (SEQ ID NO: 43) or MaSp II (SEQ ID NO: 44) polypeptide from which it is derived by up to 150 (up to 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, or 150) amino acid changes in the amino acid sequence (i.e. substitutions, insertions, deletions, N-terminal truncations and/or C-terminal truncations). Such a variant can alternatively or additionally be characterised by a certain degree of sequence identity to the reference (wild-type) polypeptide from which it is derived. Thus, an ADF-3, ADF-4, MaSp I or MaSp II variant has a sequence identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9% to the respective reference (wild-type) ADF-3, ADF-4, MaSp I or MaSp II polypeptide. Preferably, the sequence identity is over a continuous stretch of at least 20, 25, 30, 35, 40, 50, 60, 70, 80, 90, 100, 120, 150, 180, 200, 250, 300, 350, 400, or more amino acids, preferably over the whole length of the respective reference (wild-type) ADF-3, ADF-4, MaSp I or MaSp II polypeptide.

It is particularly preferred that the sequence identity is at least 80% over the whole length, is at least 85% over the whole length, is at least 90% over the whole length, is at least 95% over the whole length, is at least 98% over the whole length, or is at least 99% over the whole length of the respective reference (wild-type) ADF-3, ADF-4, MaSp I or MaSp II polypeptide. It is further particularly preferred that the sequence identity is at least 80% over a continuous stretch of at least 20, 30, 50, 100, 150, 200, 250, or 300 amino acids, is at least 85% over a continuous stretch of at least 20, 30, 50, 100, 150, 200, 250, or 300 amino acids, is at least 90% over a continuous stretch of at least 20, 30, 50, 100, 150, 200, 250, or 300 amino acids, is at least 95% over a continuous stretch of at least 20, 30, 50, 100, 150, 200, 250, or 300 amino acids, is at least 98% over a continuous stretch of at least 20, 30, 50, 100, 150, 200, 250, or 300 amino acids, or is at least 99% over a continuous stretch of at least 20, 30, 50, 100, 150, 200, 250, or 300 amino acids of the respective reference (wild-type) ADF-3, ADF-4, MaSp I or MaSp II polypeptide.

A fragment (or deletion variant) of the ADF-3 (SEQ ID NO: 1) polypeptide has preferably a deletion of up to 1, 2, 3, 4, 5, 6, 7, 8, 9, 10, 15, 20, 25, 30, 35, 40, 45, 50, 55, 60, 65, 70, 75, 80, 85, 90, 95, 100, 120, 150, 170, 200, 220, 250, 270, 300, 320, 350, 370, 400, 420, 450, 470, 500, 520, 550, 570, 600, or 610 amino acids at its N-terminus and/or at its C-terminus. The deletion can also be internally.

A fragment (or deletion variant) of the ADF-4 (SEQ ID NO: 2) polypeptide has preferably a deletion of up to 1, 2, 3, 4, 5, 6, 7, 8, 9, 10, 15, 20, 25, 30, 35, 40, 45, 50, 55, 60, 65, 70, 75, 80, 85, 90, 95, 100, 120, 150, 170, 200, 220, 250, 270, 300, 320, 330, 340, 350, 360, 370, 380, or 390 amino acids at its N-terminus and/or at its C-terminus. The deletion can also be internally.

A fragment (or deletion variant) of the MaSp I (SEQ ID NO: 43) polypeptide has preferably a deletion of up to 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 620, 640, 660, 670, 680, or 690 amino acids at its N-terminus and/or at its C-terminus. The deletion can also be internally.

A fragment (or deletion variant) of the MaSp II (SEQ ID NO: 44) polypeptide has preferably a deletion of up to 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 520, 540, 560, or 570 amino acids at its N-terminus and/or at its C-terminus. The deletion can also be internally.

Additionally, the ADF-3, ADF-4, MaSp I or MaSp II variant or fragment is only regarded as an ADF-3, ADF-4, MaSp I or MaSp II variant or fragment within the context of the present invention, if the modifications with respect to the amino acid sequence on which the variant or fragment is based do not negatively affect the ability of the polypeptide to coat, preferably to uniformly coat, the inert or naturally occurring material, such as kevlar or cotton. Preferably, the ADF-3, ADF-4, MaSp I or MaSp II variant or fragment is capable of forming a coating of a thickness of between 1 nm and 50 µm, preferably between 40 nm and 50 µm, more preferably between 0.5 µm and 10 µm and most preferably between 1.0 µm and 5 µm as it is formable using the respective reference (wild-type) ADF-3, ADF-4, MaSp I or MaSp II polypeptide. It is also preferred that the coating made from the ADF-3, ADF-4, MaSp I or MaSp II variant or fragment has a similarly surface structure (surface undulation), e.g. roughness or porosity, compared to a coating made from the respective reference (wild-type) ADF-3, ADF-4, MaSp I or MaSp II polypeptide. It is particularly preferred that the coating made from the ADF-3, ADF-4, MaSp I or MaSp II variant or fragment exhibits a surface structure and a thickness similarly to a coating made from the respective reference (wild-type) ADF-3, ADF-4, MaSp I or MaSp II polypeptide. The skilled person can readily assess the thickness or the surface structure (surface undulation) of a coating using electronic-microscopy.

In another embodiment the silk polypeptide comprises an amino terminal and/or a carboxy terminal TAG selected from the group consisting of (i) $TAG^{CYS1}$ consisting of the amino acid sequence GCGGGGGGSGGGG (SEQ ID NO: 35), (ii) $TAG^{CYS2}$ consisting of the amino acid sequence GCGGGGGG (SEQ ID NO: 36), (iii) $TAG^{CYS3}$ consisting of the amino acid sequence GCGGSGGGSGGGG (SEQ ID NO: 37), (iv) $TAG^{LYS1}$ consisting of the amino acid sequence GKGGGGGGSGGGG (SEQ ID NO: 38), and (v) $TAG^{LYS2}$ consisting of the amino acid sequence GKGGGGGG (SEQ ID NO: 39).

These TAGs contain cysteine and/or lysine and can be used to covalently link the silk polypeptide to the inert material or to link substances to the silk polypeptide as described below.

Most preferably, the silk polypeptide used in the method of the present invention comprises or consists of $TAG^{CYS1}C_{16}$, $C_{16}TAG^{CYS1}$, $TAG^{CYS1}C_{16}TAG^{CYS1}$, $TAG^{CYS2}C_{16}$, $C_{16}TAG^{CYS2}$, $TAG^{CYS2}C_{16}TAG^{CYS2}$, $TAG^{CYS3}C_{16}$, $C_{16}TAG^{CYS3}$, $TAG^{CYS3}C_{16}TAG^{CYS3}$, $TAG^{LYS1}C_{16}$, $C_{16}TAG^{LYS1}$, $TAG^{LYS1}C_{16}TAG^{LYS1}$, $TAG^{LYS2}C_{16}$, $C_{16}TAG^{LYS2}$, or $TAG^{LYS2}C_{16}TAG^{LYS2}$.

Preferably, the concentration of the silk polypeptide in the solution provided in the method of the present invention is in the range of 0.1 wt %/vol to 30 wt %/vol, preferably in the range of 1 wt %/vol to 10 wt %/vol, most preferably in the range of 2 to 8 wt %/vol or 4 to 6 wt %/vol. Thus, for example, the concentration of the silk polypeptide in the solution provided in the method of the present invention is 0.1, 0.4, 0.6, 0.8, 1.0, 1.2, 1.4, 1.6, 1.8, 2.0, 2.2, 2.4, 2.6, 2.8, 3.0, 3.5, 4.0, 4.5, 5.0, 5.5, 6.0, 6.5, 7.0, 7.5, 8.0, 9.0, 10.0, 12.0, 15.0, 18.0, 20.0, 25.0 or 30.0 wt %/vol.

Preferably, the solvent provided in the method of the present invention is a van der Waals forces destabilising solvent, formic acid, an aqueous solution, preferably $H_2O$ or a buffered aqueous solution (e.g. Tris-buffered aqueous solution), or mixtures thereof. Most preferably, the van der Waals forces destabilising solvent is selected from the group consisting of Hexafluoroisopropanol (HFIP), Trichloroacidicacid (TCA), Trifluoroacidicacid (TFA) and Lithium bromide (LiBr). Water is most preferred due to its good availability and non-toxicity. In these solvents, the silk polypeptides are solved or suspended. The term "suspension" in the context of the present invention refers to a dispersion of solid particles in a liquid. If the particles are ~100 nm in diameter, the suspension is colloidal.

It is preferred that the inert or naturally occurring material coated in the method of the present invention is selected from the group consisting of a fiber, a thread comprising a fiber, a twisted yarn comprising a fiber, a woven fabric comprising a fiber and a non-woven fabric comprising a fiber.

The coating of a woven fabric is more practical, less time consuming and requires less coating material. The coating of fibers and subsequent weaving of fabrics is more complex, more expensive but more reproducible and of higher value. The coating of a woven fabric of cotton with the silk polypeptide $C_{16}$ is exemplified in Example IV. FIG. 4 shows a comparison between an untreated already woven fabric and a coated already woven fabric.

It is preferred that the inert material is an inert synthetic material or an inert inorganic material. Preferably, the inert material is
(i) an inert synthetic material selected from the group consisting of polyester (Diolen, Trevira), polyamide (PA, e.g. Nylon or Perlon), polyaramid (e.g. Kevlar, Twaron, or Nomex), polytetrafluorethylene (PTFE; e.g. Teflon), polyethylene (PE; e.g. Dyneema), polypropylene (PP), polyurethane (PU; e.g. Lycra), silicone, a mixture of polyurethane and polyethylenglycol (elastane), ultra high molecular weight polyethylene (UHMWPE), and high-performance polyethylene (HPPE), or
(ii) an inert inorganic material selected from the group consisting of glass, carbon, ceramic, metal, (metal) alloy, sapphire, diamond and semiconductor.

The inventors of the present invention have surprisingly found that the use of silk polypeptides as coating materials provides a highly efficient coating under mildest conditions and enables the manufacture of silk coated inert inorganic materials tailored for specific applications. Up to now, very harsh conditions (if at all), like plasma treatment, were necessary to alter inert inorganic materials, e.g. inert inorganic fibers.

The inert synthetic materials polyester, polyamide (PA) and polyaramid are polycondensation materials (e.g. polycondensation fibers), i.e. said materials are produced by a polycondensation reaction. A polycondensation reaction leads to the formation of a polymer by the linking together of molecules of a monomer and the releasing of water or a similar substance. The inert synthetic materials polytetrafluorethylene (PTFE), polyethylene (PE), and polypropylene (PP) are polymerisation materials (e.g. polymerisation fibers), i.e. said materials are produced by a polymerisation reaction. A polymerization reaction is a process of reacting monomer molecules together in a chemical reaction to form three-dimensional networks or polymer chains. The inert synthetic materials polyurethane (PU) and a mixture of polyurethane and polyethylenglycol are polyaddition materials (e.g. polyaddition fibers), i.e. said materials are produced by a polyaddition reaction. In a polyaddition reaction many monomers are bond together via rearrangement of bonds without the loss of any atom or molecule. This is in contrast to a condensation polymer which is formed by a condensation reaction where a molecule, usually water, is lost during the formation.

It is preferred that the metal as inert inorganic material is selected from the group consisting of platinum (Pt), chromium (Cr), silver (Ag), gold (Au) and compositions/alloys thereof. Preferably, the inorganic material is a semiconductor and is selected from the group consisting of iron (Fe), copper (Cu), germanium (Ge), silicium (Si), selenium (Se), tellurium (Te) and compositions/alloys thereof. It is further preferred that the (metal) alloy is steel.

Preferably, the naturally occurring material is selected from the group consisting of silk, cotton, cellulose, flax, wool, hemp, bamboo, rubber, hair such as real hair (e.g. human hair or animal hair) or artificial hair, and skin such as human skin or animal skin. The real hair (e.g. human hair) or the artificial hair may be hair for hair extensions, periwigs, hair pieces, or toupees. The real hair (e.g. human hair) or the artificial hair may also be part of periwigs, hair pieces, or toupees.

Insofar as the method of the present invention relates to the coating of naturally occurring materials such as hair, particularly real hair (e.g. human or animal hair), or skin (e.g. human or animal skin), with silk polypeptides, said method is preferably for cosmetic purposes, e.g. to reduce the roughness of hair and/or to improve the brilliance of hair, or to improve the humidity and/or softness of skin.

Thus, for example, a polyaramid fiber, polyaramid thread, polytetrafluorethylene fiber, a polytetrafluorethylene thread, a carbon fiber, a carbon thread a glass fiber, a glass thread, a nylon fiber, a nylon thread, a cotton fiber, a cotton thread, a woven fabric of cotton, a non-woven fabric of cotton, a woven fabric of wool, or a non-woven fabric of wool can be coated with a silk polypeptide in the method of the present invention.

The selection of the inert or naturally occurring base material for the coating with the silk polypeptide depends on the subsequent application of the coated inert or naturally occurring material. For example, in case that a thread of inert synthetic material (e.g. a polyaramid thread) having an improved surface feel is desired, it is not required to first coat the fiber of inert synthetic material (e.g. a polyaramid fiber) with a silk polypeptide and to subsequently produce a thread from said fiber. In addition, the direct coating of a woven fabric with a silk polypeptide results in a comparable, but different, coating pattern in comparison to a woven fabric produced from an already silk polypeptide coated fiber. This means that in a woven fabric coating, the interspaces can be filled with a silk polypeptide, while in a woven fabric produced from an already silk polypeptide coated fiber, the interspaces are free of silk polypeptide coating. Therefore, if a coating of the woven fabric material with filled interspaces is desired, it is advantageous to use a woven fabric as a basis material for the coating method of the present invention.

By a way of example, the method of the present invention can comprise the steps of:
  i) providing a solution which comprises a silk polypeptide consisting of $C_{16}$ as repetitive units and $H_2O$ as a solvent, and
  ii) applying the solution on a polyaramid (Kevlar) fiber as an inert synthetic material and thereby coating the polyaramid fiber with the silk polypeptide consisting of $C_{16}$ as repetitive units.

The method of the present invention can further comprise the steps of:
  i) providing an aqueous solution which comprises a silk polypeptide consisting of $C_{16}$ as repetitive units, and
  ii) applying the solution on a polytetrafluorethylene (Teflon) thread as an inert synthetic material and thereby coating the polytetrafluorethylene thread with the silk polypeptide consisting of $C_{16}$ as repetitive units.

The method of the present invention can further comprise the steps of:
  i) providing a solution which comprises a silk polypeptide consisting of $(AQ)_{24}NR3$ as repetitive units and formic acid as a solvent, and
  ii) applying the solution on a polytetrafluorethylene (Teflon) thread as an inert synthetic material and thereby coating the polytetrafluorethylene thread with the silk polypeptide consisting of $(AQ)_{24}NR3$ as repetitive units.

The method of the present invention can also comprise the steps of:
  i) providing a solution which comprises a silk polypeptide consisting of $C_{16}$ as repetitive units and Hexafluoroisopropanol (HFIP) as a solvent, and
  ii) applying the solution on a flax fiber as a naturally occurring material and thereby coating the flax fiber with the silk polypeptide consisting of $C_{16}$ as repetitive units.

In addition, the method of the present invention can comprise the steps of:
  i) providing an aqueous solution which comprises a silk polypeptide consisting of $C_{32}$ as repetitive units, and
  ii) applying the solution on a woven fabric of wool as a naturally occurring material and thereby coating the woven fabric of wool with the silk polypeptide consisting of $C_{32}$ as repetitive units.

In the context of the above mentioned examples $C_{16}$ means 16 repetitive units of module C and $C_{32}$ means 16 or 32 repetitive units of module C.

Preferably, the silk polypeptide in the coating is covalently and/or non-covalently linked to the inert material or to the naturally occurring material. The term "covalent linkage" means a type of chemical linkage, wherein each atom of a bond pair contributes one electron to form a pair of electrons in a chemical bond. It is preferred that the silk polypeptide is covalently linked (a) via a cysteine residue, a lysine residue, the amino terminus, the carboxy terminus, the amino terminal TAG or the carboxy terminal TAG of the silk polypeptide, and/or
(b) via cross-linking to the inert or naturally occurring material.

The silk polypeptide can be covalently linked via the formation of an amide-bond or a disulfide-bond to the naturally occurring material (e.g. wool or flax) in the method of the present invention. The term "amide-bond" (amide-linkage) refers to a chemical bond formed between two molecules (e.g. polypeptides) when the carboxyl group of one molecule reacts with the amine group of the other molecule, thereby releasing a molecule of water ($H_2O$). The term "disulfide-bond" (disulfide-linkage) refers to a chemical bond, which is usually derived by the coupling of two thiol groups of cysteine residues. The linkage is also called an SS-bond or disulfide bridge.

Thus, for example, the silk polypeptide (e.g. the silk polypeptide comprising $C_{16}$) used in the method of the present invention can be covalently linked via its amino terminus or via its carboxy terminus to the naturally occurring material (e.g. flax or wool) by forming an amide-bond. The silk polypeptide can be also covalently linked via its amino terminal TAG (e.g. $TAG^{CYS1}C_{16}$) or via its carboxy terminal TAG (e.g. $C_{16}TAG^{CYS1}$) to the naturally occurring material (e.g. flax or wool) by forming an disulfide-bond. In addition, the silk polypeptide (e.g. $A^KQ_4$) can be covalently linked via its lysine residue (e.g. the lysine residue in the repetitive unit $A^K$ of the silk polypeptide $A^KQ_4$) to the naturally occurring material (e.g. flax or wool) by forming an amide-bond. Furthermore, the silk polypeptide can be covalently linked via its cysteine residue (e.g. the cysteine residue in the repetitive unit $A^C$ of the silk polypeptide $A^CQ_4$) to the naturally occurring material (e.g. flax or wool) by forming a disulfide-bond.

Combinations of the covalent linkages of the silk polypeptide to the naturally occurring material as mentioned under (a) are also preferred. Thus, for example, the silk polypeptide (e.g. $C_{16}TAG^{CYS1}$) can be covalently linked (i) via its cysteine residue (e.g. the cysteine residue in the carboxy terminal $TAG^{CYS1}$ of the silk polypeptide $C_{16}TAG^{CYS1}$) to the naturally occurring material (flax or wool) by forming a disulfide-bond and (ii) via its amino terminus (e.g. the amino terminus of $C_{16}$ of the silk polypeptide $C_{16}TAG^{CYS1}$) to the naturally occurring material (e.g. flax or wool) by forming an amide-bond. The silk polypeptide (e.g. $A^C_4TAG^{LYS1}$) can also be covalently linked (i) via its lysine residue (e.g. the lysine residue in the carboxy terminal $TAG^{LYS1}$ of the silk polypeptide $A^C_4TAG^{LYS1}$) to the naturally occurring material (e.g. flax or wool) by forming an amide-bond and (ii) via its cysteine residue (e.g. the cysteine residue in the repetitive unit $A^C$ of the silk polypeptide $A^C_4TAG^{LYS1}$) to the naturally occurring material (e.g. flax or wool) by forming a disulfide-bond.

The silk polypeptide can also be non-covalently linked to the inert or naturally occurring material. The term "non-covalent linkage" means a type of linkage (interaction) that does not involve the sharing of pairs of electrons, but rather involves more dispersed variations of electromagnetic interactions, hydrophobic interactions or van der Waals interactions.

It is particularly preferred that the silk polypeptide is non-covalently linked to the inert material (e.g. polyester, polyaramid, or polytetrafluorethylene) or naturally occurring material (e.g. wool, flax or cotton) via an ionic (electrostatic) linkage (interaction) or via a hydrophobic linkage (interaction). The term "hydrophobic linkage" (hydrophobic interaction) refers to a linkage (an interaction) dependent from the tendency of hydrocarbons to form intermolecular aggregates in an aqueous medium. The term "ionic (electrostatic) linkage" (ionic (electrostatic) interaction) refers to a non-covalent bond (ionic (electrostatic) bond) in which one atom loses an electron to form a positive ion and the other atom gains to electron to form a negative ion.

The coating of an aramid (Kevlar) fiber with the silk polypeptide $C_{16}$ is described in Example I. The aramid filament coated with the silk polypeptide $C_{16}$ is shown in FIG. 2.

The unexpected finding that inert materials or naturally occurring materials can be coated with a silk polypeptide layer enables new opportunities for various applications. It is common knowledge that proteins generally tend to aggregate unspecifically, especially in the presence of inert materials. Standard proteins like haemoglobin, BSA or Cytochrome C simply aggregate and, thus, result in an uneven surface—if they stick at all to the surface. Surprisingly, silk polypeptides (e.g. spider silk polypeptides) form an even and smooth surface layer, in particular on stiff and rough inert synthetic materials like polyaramid or carbon materials (e.g. polyaramid or carbon threads). Apart from the optical and haptic advantages, silk polypeptide coatings allow further modifications and, thus, a new range of possible applications for the coated inert or naturally occurring materials.

Thus, in a preferred embodiment of the present invention, the silk polypeptide further comprises at least one substance, i.e. 1, 2, 3, 4, 5, 6, or more substances, preferably 1 or 2 substances, which is covalently and/or non-covalently linked to the silk polypeptide.

Preferably, the substance is covalently and/or non-covalently linked to the silk polypeptide prior to step i), subsequently to step i), and/or subsequently to step ii) of the method of the present invention.

If the coupling/linking of the substance to the silk polypeptide is performed prior to the application of the silk polypeptides on the inert or naturally occurring material (i.e. prior to step i), or subsequently to step i) of the method of the present invention), afterwards (i.e. subsequently to step ii) of the method of the present invention) or several times (i.e. prior to step i) and subsequently to step i) and subsequently to step ii); prior to step i) and subsequently to step ii); prior to step i) and subsequently to step i); or subsequently to step i) and subsequently to step ii) of the method of the present invention) depends on the substance attached, the type of attachment and the desired application of the coated material. The multiple coupling of silk polypeptides is advantageous in case that different substances are coupled to the silk polypeptide.

It is preferred that the non-covalent linkage of a substance is performed subsequently to step ii) of the method of the present invention. If a coated product with a high amount of covalently linked substance is desired, it is preferred that the linkage of the substance is performed several times, e.g. subsequently to step i) and subsequently to step ii). Preferably, the substance is covalently linked (a) via a cysteine residue, a lysine residue, the amino terminus, the carboxy terminus, the amino terminal TAG or the carboxy terminal TAG of the silk polypeptide, and/or
(b) via crosslinking
to the silk polypeptide.

The substances can be covalently linked to the silk polypeptide via cross-linking in the process of the present invention. The term "cross-linking" refers to a process of chemically joining two molecules by a covalent bond. Cross-linking or coupling reagents contain reactive ends to specific functional groups (primary amines, suithydryl, etc.) on polypeptides or on other molecules. Preferably, the cross-linking or coupling reagent used in the method of the present invention is 1-ethyl-3-(3-dimethylaminopropyl)-carbodiimide hydrochloride (EDC) or Glutaraldehyde.

Therefore, for example, the substance (e.g. an enzyme, antibody or antibody fragment) used in the method of the present invention can be covalently linked via the amino terminus or via the carboxy terminus of the silk polypeptide to the silk polypeptide (e.g. the silk polypeptide comprising $C_{16}$) by forming an amide-bond. The substance (e.g. enzyme or antibody) can also be covalently linked via the amino terminal TAG (e.g. $TAG^{CYS1}C_{16}$) or via the carboxy terminal TAG (e.g. $C_{16}TAG^{CYS1}$) of the silk polypeptide to the silk polypeptide by forming a disulfide-bond. In addition, the substance (e.g. enzyme or antibody) can be covalently linked via the lysine residue of the silk polypeptide (e.g. the lysine residue in the repetitive unit $A^K$ of the silk polypeptide $A^KQ_4$) to the silk polypeptide (e.g. $A^KQ_4$) by forming an amide-bond. Furthermore, the substance (e.g. enzyme or antibody) can be covalently linked via the cysteine residue of the silk polypeptide (e.g. the cysteine residue in the repetitive unit $A^C$ of the silk polypeptide $A^CQ_4$) to the silk polypeptide (e.g. $A^CQ_4$) by forming a disulfide-bond.

Combinations of the covalent linkages of the substance to the silk polypeptide as mentioned under (a) are also preferred. Thus, for example, the substance (e.g. enzyme or antibody) can be covalently linked (i) via the amino terminus and (ii) via the carboxy terminus of the silk polypeptide to the silk polypeptide (e.g. the silk polypeptide comprising $C_{16}$) by forming an amide-bond. The substance (e.g. enzyme or antibody) can be covalently linked (i) via the cysteine residue of the silk polypeptide (e.g. the cysteine residue in the carboxy terminal $TAG^{CYS1}$ of the silk polypeptide $C_{16}TAG^{CYS1}$) to the silk polypeptide (e.g. $C_{16}TAG^{CYS1}$) by forming a disulfide-bond and (ii) via the amino terminus of the silk polypeptide (e.g. the amino terminus of $C_{16}$ of the silk polypeptide $C_{16}TAG^{CYS1}$) to the silk P (e.g. $C_{16}TAG^{CYS1}$) by forming an amide-bond. The substance (e.g. enzyme or antibody) can also be covalently linked (i) via the lysine residue of the silk polypeptide (e.g. the lysine residue in the carboxy terminal $TAG^{LYS1}$ of the silk polypeptide $A^C{}_4TAG^{LYS1}$) to the silk polypeptide (e.g. $A^C{}_4TAG^{LYS1}$) by forming an amide-bond and (ii) via the cysteine residue of the silk polypeptide (e.g. the cysteine residue in the repetitive unit $A^C$ of the silk polypeptide $A^C{}_4TAG^{LYS1}$) to the silk polypeptide (e.g. $A^C{}_4TAG^{LYS1}$) by forming a disulfide-bond.

As mentioned above, the substance (e.g. a dye or an enzyme) can also be covalently linked via cross-linking to the silk polypeptide in the process of the present invention. Preferably, the cross-linking or coupling reagent used in the method of the present invention is 1-ethyl-3-(3-dimethylaminopropyl)-carbodiimide hydrochloride (EDC) or Glutaraldehyde. The crosslinking of the enzyme β-galactosidase and the fluoresceine dye to a polyaramid fiber coated with the silk polypeptide $C_{16}$ is described in Example II.

Preferably, the covalently linked/coupled substance is selected from the group consisting of a polypeptide, a lipid, a dye, a conjugated metal, activated carbon, and an agent. Most preferably, (i) the polypeptide is an enzyme, preferably β-galactosidase, an antibody, a hormone, preferably insulin, or an antigen;

(ii) the lipid is a cholesterol, a steroid, a wax, or an oil;
(iii) the dye is a synthetic dye, preferably an azo compound, an inorganic dye, preferably a metal salt, or an organic dye, preferably a fluoresceine dye or a rhodamine dye;
(iv) the conjugated metal is Nanogold®;
(v) the activated carbon is selected from the group consisting of powdered activated carbon (PAC), granular activated carbon (GAC) and extruded activated carbon (EAC);
(vi) the agent is selected from the group consisting of a pharmaceutical agent, a hemostatic agent, a growth-stimulating agent, an anti-inflammatory agent, an anti-fowling agent, an antimicrobial agent, an antibacterial agent, an antifungal agent, a pesticide and an UV protecting agent.

The substances to be incorporated may be solid, semi-solid or liquid without limitation. The substance can also be non-covalently linked to the silk polypeptide. It is particularly preferred that the substance is non-covalently linked to the silk polypeptide via an ionic (electrostatic) linkage (interaction), via a hydrophobic linkage (interaction) or via adhesion.

Preferably, the non-covalently linked/coupled substance is selected from the group consisting of a polypeptide, a lipid, a dye, a conjugated metal, an activated carbon, a metal salt, and an agent. Most preferably,
(i) the polypeptide is an enzyme, preferably β-galactosidase, an antibody, a hormone, preferably insulin, or an antigen;
(ii) the lipid is a cholesterol, a steroid, a wax, or an oil;
(iii) the dye is a synthetic dye, preferably an azo compound, an inorganic dye, preferably a metal salt, or an organic dye, preferably a fluoresceine dye or a rhodamine dye;
(iv) the conjugated metal is Nanogold®;
(v) the activated carbon is selected from the group consisting of powdered activated carbon (PAC), granular activated carbon (GAC) and extruded activated carbon (EAC);
(vi) the metal salt is a cation selected from the group consisting of copper, cobalt nickel, or silver;
(vii) the agent is selected from the group consisting of a pharmaceutical agent, a hemostatic agent, a growth-stimulating agent, an anti-inflammatory agent, an anti-fowling agent, an antimicrobial agent, an antibacterial agent, an antifungal agent, a pesticide and an UV protecting agent.

The non-covalent linkage of either copper chloride or cobalt chloride to an aramid fiber coated with the silk polypeptide $C_{16}$ is described in Example III.

The non-covalent coupling is suitable for the introduction of metal salts or agents into the coating to allow a defined release of the substance over a certain period of time. This is needed for some purposes, i.e. polyaramid thread coatings in medicinal technology. Thus, for the first time, it is now possible to achieve a controlled release of salts or agents from a coated inert synthetic or inorganic material, e.g. polyaramid threads or fabrics. It was completely unforeseeable that inert synthetic or inorganic materials, e.g. polyaramid threads or fabrics, can be modified in such a convenient way.

For other applications, e.g. the manufacture of water-repellent fabrics, the covalent linkage of a substance to the silk polypeptide is more suitable. During rain, the incorporated substance should not be washed out from the silk coated inert synthetic material, inert inorganic material, or naturally occurring material. In addition, for the manufacturing of fabrics having an antiseptic or anti-transpire effect, it is also favoured to covalently link the substance, e.g. silver or bacteriostatic compounds to the silk coated inert synthetic material, inert inorganic material, or naturally occurring material It is preferred that step ii) of the method of the present invention is carried out at temperatures between 4° C. and 80° C., preferably between 4° C. and 40° C. For example, step ii) of the method of the present invention can be carried out at 4° C., 8° C., 10° C., 12° C., 15° C., 18° C., 20° C., 21° C., 22° C., 23° C., 24° C., 25° C., 28° C., 30° C., 35° C., 40° C., 45° C., 50° C., 55° C., 60° C., 65° C., 70° C., 75° C., or 80° C. Most preferably, step ii) of the method of the present invention is carried out between 20° C. and 25° C.

The inventors of the present invention have surprisingly found that inert or naturally occurring material can be coated under mild reaction conditions, i.e. mild temperatures such as temperatures between 4 and 80° C. The coated product has improved haptic and optical properties. Preferably, the method further comprises the steps of:
iii) providing a solution which comprises at least one silk polypeptide comprising at least two identical repetitive units, and optionally at least one non-repetitive (NR) unit, and a solvent, and
iv) applying the solution on an inert material or on a naturally occurring material and thereby coating for the second time the inert or naturally occurring material with a silk polypeptide,
wherein the silk polypeptide of step (iii) is identical or different to the silk polypeptide of step (i). Thus, for example, in a preferred embodiment of the present invention, the method further comprises the steps of:
iii) providing a solution which comprises the silk polypeptide $C_{16}$ and formic acid as a solvent, and
iv) applying the solution on a polyaramid fiber and thereby coating for the second time the polyaramid fiber with a silk polypeptide,
wherein the silk polypeptide $C_{16}$ of step (iii) is identical to the silk polypeptide $C_{16}$ of step (i). In another preferred embodiment of the present invention, the method further comprises the steps of:
iii) providing a solution which comprises the silk polypeptide $(AQ)_{24}NR4$ and Hexafluoroisopropanol (HFIP) as a solvent, and
iv) applying the solution on a polytetrafluorethylene thread and thereby coating for the second time the polytetrafluorethylene thread with a silk polypeptide,
wherein the silk polypeptide $(AQ)_{24}NR4$ of step (iii) is different to the silk polypeptide $C_{16}$ of step (i). In a further preferred embodiment of the present invention, the method further comprises the steps of:
iii) providing an aqueous solution which comprises the silk polypeptide $C_{16}$, and
iv) applying the solution on a polyaramid fiber and thereby coating for the second time the polyaramid fiber with a silk polypeptide,
wherein the silk polypeptide $C_{16}$ of step (iii) is identical to the silk polypeptide $C_{16}$ of step (i).

It is preferred that the steps (iii) and (iv) of the method of the present invention are repeated several times, preferably 3 to 10 times, i.e. 3, 4, 5, 6, 7, 8, 9, or 10 times, to obtain a coated inert or naturally occurring material of different thickness and multiple layers.

Preferably, the coating of the inert or naturally occurring material has a thickness of between 1 nm and 50 μm, preferably between 40 nm and 50 μm, more preferably between 0.5 µm and 10 µm, more preferably between 0.8 µm and 8 µm and most preferably between 1.0 µm and 5.0 µm, i.e. 1.0 µm, 1.1 µm, 1.2 µm, 1.3 µm, 1.4 µm, 1.5 µm, 1.6 µm, 1.7 µm, 1.8 µm, 1.9 µm, 2.0 µm, 2.1 µm, 2.2 µm, 2.3 µm, 2.4 µm, 2.5 µm, 2.6 µm, 2.7 µm, 2.8 µm, 2.9 µm, 3.0 µm, 3.1 µm, 3.2 µm, 3.3 µm, 3.4 µm, 3.5 µm, 3.6 µm, 3.7 µm, 3.8 µm, 3.9 µm, 4.0 µm, 4.1 µm, 4.2 µm, 4.3 µm, 4.4 µm, 4.5 µm, 4.6 µm, 4.7 µm, 4.8 µm, 4.9 µm, or 5.0 µm.

It is preferred that the coated inert or naturally occurring materials comprises 3, 4, 5, 6, 7, 8, 9, or 10 layers of different or identical silk polypeptides, preferably of different silk polypeptides.

Thus, for example, in a preferred embodiment of the present invention, the method comprises the following steps:
i) providing an aqueous solution which comprises the silk polypeptide $C_{16}$,
ii) applying the solution on a polyaramid thread and thereby coating the polyaramid thread with the silk polypeptide $C_{16}$,
iii) providing an aqueous solution which comprises the silk polypeptide $(AQ)_{24}NR^4$, and
iv) applying the solution on a polyaramid thread and thereby coating for the second time the polyaramid thread with a silk polypeptide,
wherein the silk polypeptide $(AQ)_{24}NR4$ of step (iii) is different to the silk polypeptide $C_{16}$ of step (i), and wherein the coating of the polyaramid thread comprises two different layers (i.e. first layer: silk polypeptide $C_{16}$ and second layer silk polypeptide $(AQ)_{24}NR4$) and has a thickness of 0.05 µm.

It is further preferred that the method of the present invention comprises subsequently to step ii), step iii), and/or step iv) a step of post-modifying the coated or natural material by means of staining/finishing which confer protection against visible light, ultra-violet radiation or water-resistance, abrasion, mechanical stress, acids and/or bases.

In a second aspect, the present invention provides a coated inert or naturally occurring material obtainable by the method of the first aspect.

In a third aspect, the present invention provides products comprising the coated inert or naturally occurring material of the second aspect, such as
(i) a fiber,
(ii) a thread comprising the fiber of (i), or
(iii) a twisted yarn, a woven fabric or a non-woven fabric comprising the fiber of (i).

In a fourth aspect, the present invention relates to the use of the coated inert or naturally occurring material of the second aspect for controlled release of the at least one substance, i.e. 1, 2, 3, 4, 5, 6, or more substances, preferably 1 or 2 substances, over a certain period of time, preferably over 6 hours up to 8 days, more preferably over 24 hours up to 5 days and most preferably over 12 hours, 24 hours, 48 hours, 12 hours, 96 hours, or 120 hours, or for the manufacture of protective or water-repellent clothing.

In a fifth aspect, the present invention relates to the use of a silk polypeptide to dye inert materials. It is preferred that the inert materials are synthetic inert materials or inorganic inert materials. Preferably, the inert material is
(i) a synthetic inert material selected from the group consisting of polyester, polyamide (PA), polyaramid, polytetrafluorethylene (PTFE), polyethylene (PE), polypropylene (PP), polyurethane (PU), silicone, a mixture of polyurethane and polyethylenglycol (elastane), ultra high molecular weight polyethylene (UHM-WPE), and high-performance polyethylene (HPPE), or
(ii) an inorganic inert material selected from the group consisting of, glass, carbon, ceramic, metal, sapphire, diamond, and semiconductor.

In a further aspect, the present invention relates to a silk polypeptide for the treatment or prevention of skin diseases selected from the group consisting of allergy, rash, eczema dermatitis, herpes, skin infections, psoriasis, acne, sun burn, and warts. Preferably, the prevention of skin diseases relates to a moisturizing effect and protection against UV radiation.

In another aspect, the present invention relates to the use of a silk polypeptide for the manufacture of a medicament for the treatment or prevention of skin diseases selected from the group consisting of allergy, rash, eczema dermatitis, herpes, skin infections, psoriasis, acne, sun burn, and warts. Preferably, the prevention of skin diseases relates to a moisturizing effect and protection against UV radiation.

The following figures and examples are merely illustrative of the present invention and should not be construed to limit the scope of the invention as indicated by the appended claims in any way.

BRIEF DESCRIPTION OF THE FIGURES

FIG. 2 shows that the spider silk coating is uniformly distributed over the aramid (Kevlar) filament.

FIG. 3 shows the coating of an untreated inert synthetic fiber with a spider silk polypeptide and the subsequently coating of the coated inert synthetic fiber with an agent or a chemical molecule.

In FIG. 7 A, western-blot analysis of $AQ_{24}NR3$ with and without Cy5 is shown. Human hair coated by Cy5-labeled $AQ_{24}NR3$ is shown in FIGS. 7 B and C.

EXAMPLES

In order to perform coating reactions, the inventors exemplarily designed the synthetic silk polypeptides $C_{16}$, $C_{32}$, $C_{16}NR4$, $(AQ)_{24}$ and $(AQ)_{24}NR3$ which are derived from the dragline silk proteins ADF-3 and ADF-4 from the European garden cross spider *Araneus diadematus*. The proteins were chosen based on previous observations that ADF-3 and ADF-4 as well as their variants display an efficient assembly behaviour.

Figure 2:
FIG. 2: Electron microscopy of a spider silk coated aramid (Kevlar) filament.
Figure 2:
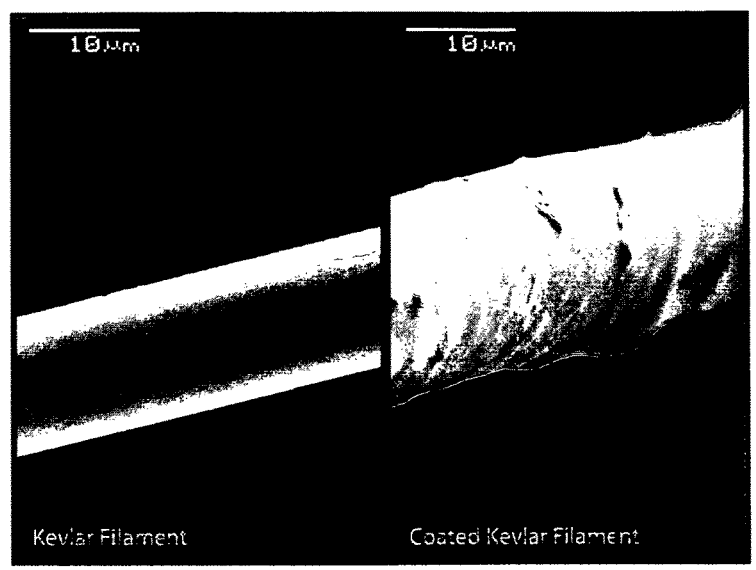
Figure 2:
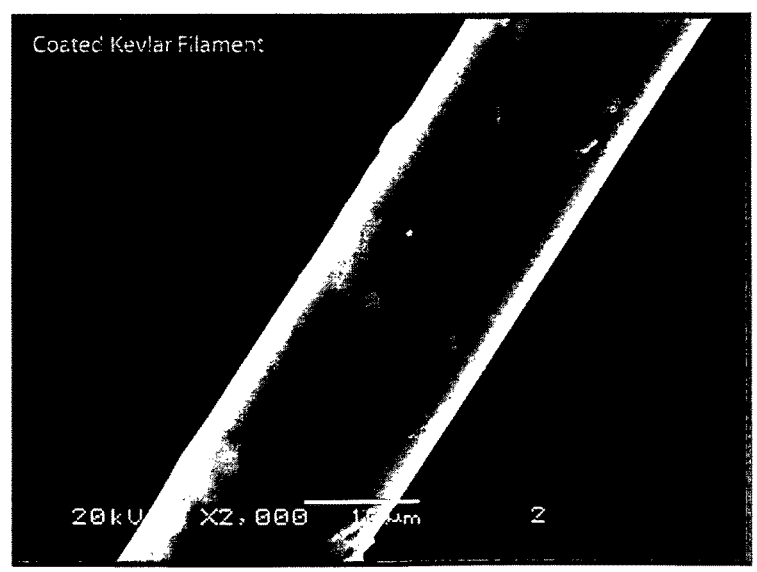

Example I: Coating of an Aramid Fiber with the Spider Silk Polypeptide $C_{16}$ A single aramid (Kevlar) fiber was incubated for 5 seconds in a HFIP (Hexafluoroisopropanol) solution containing 2 wt %/vol of the spider silk polypeptide $C_{16}$ at room temperature (25° C.). After evaporation of the solvent, the spider silk polypeptide $C_{16}$ formed a transparent film around the aramid fiber. The thickness of the film measured via electron microscopy was 3 μm (see FIG. 2).

The same results can be obtained with other solvents such as formic acid and water. Similar experiments were performed using nylon fibers, glass fibers, carbon fibers, cellulose fibers, PTFE (teflon) fibers, elastane (spandex) fibers and human hair. All examined fibers could be coated accordingly, using the described method.

To test the chemical stability of the coated fiber, spider silk polypeptide $C_{16}$ coatings were incubated for 24 hours in 8 M urea, 6 M guanidinium hydrochloride and 6 M guanidinium thiocyanate. Spider silk polypeptide $C_{16}$ coatings processed with 1M potassium phosphate or 100% methanol could only be dissolved in guanidinium thiocyanate. This remarkable chemical stability of spider silk polypeptide $C_{16}$ coatings is identical to that of natural dragline silk and to that of recombinantly produced and assembled ADF-4. Previous studies could correlate assembly properties and stabilities of assembled structures directly with the amino acid sequences of the silk proteins. Thus, properties of spider silk coatings can directly be modified by altering the primary structure of the silk protein via manipulation of the corresponding silk gene.

Figure 3:
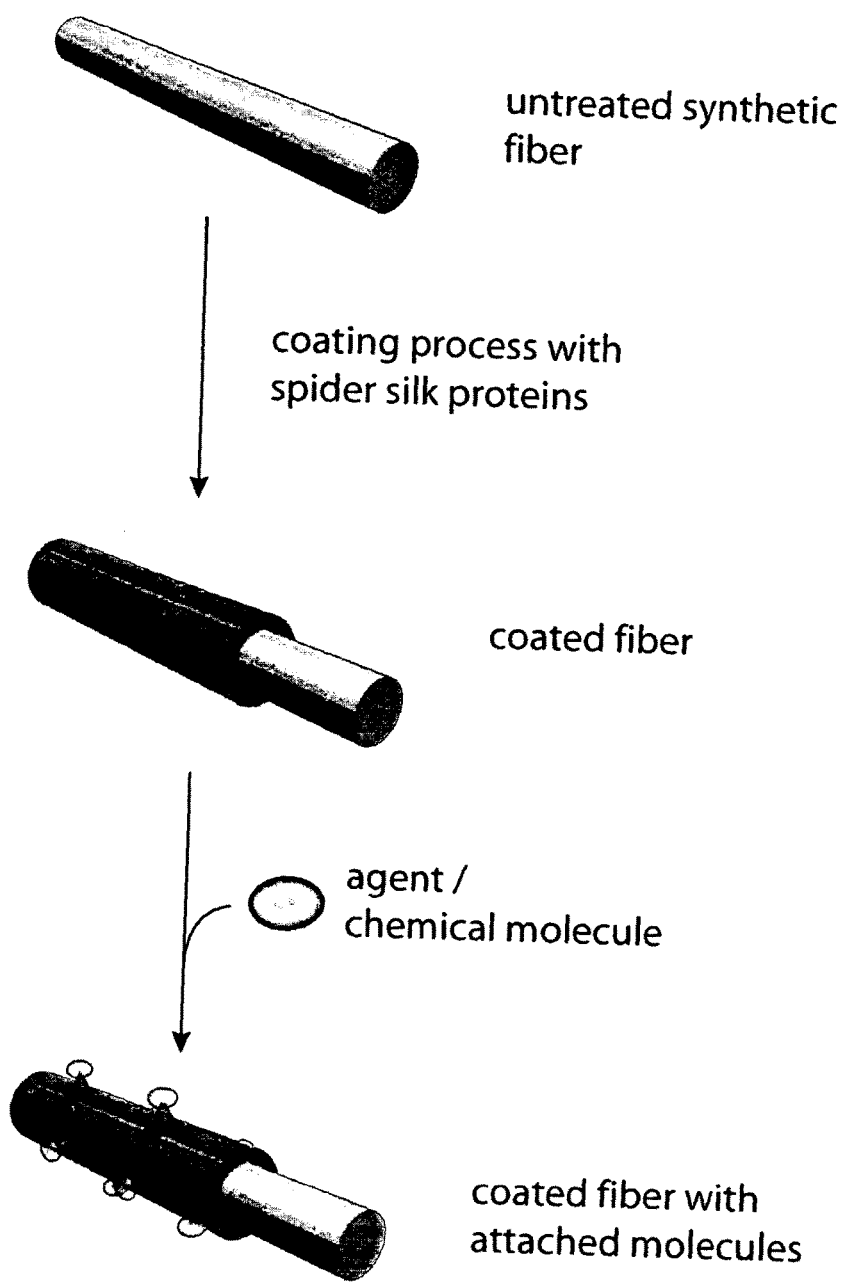
FIG. 3: Technical process to covalently attach molecules to the spider silk coating.

Example II: Covalent Coupling Via Chemically Crosslinking of a Substance to the Silk Polypeptide $C_{16}$ Coated on an Aramid Fiber Many applications of fibers require the presence of specific functionalities on the fiber surface. In order to demonstrate that the spider silk coatings can be subsequently modified with a substance, the chromophor fluorescein and the enzyme ß-galactosidase were chemically coupled to a silk polypeptide $C_{16}$ coated on an aramid fiber as a proof of principle (see FIG. 3). The coupling was achieved by activating surface exposed carboxyl groups of the spider silk polypeptide $C_{16}$ using 1-ethyl-3-(3-dimethylaminopropyl) carbodiimide (EDC). The spider silk polypeptide $C_{16}$ coated aramid fibers were further incubated with ethylenediamine leading to the formation of an amide. The remaining free amino group of ethylenediamine was subsequently coupled to fluoresceinisothiocyanate resulting in the efficient covalent linkage of fluorescein via formation of a stable thiourea derivative.

Similarly, incubation of ß-galactosidase with EDC-activated $C_{16}$ films led to the formation of amide bonds between carboxyl groups of the silk polypeptide $C_{16}$ and primary amines (e.g. from lysine residues) of ß-galactosidase which were accessible at the enzyme's surface. After repeated washing of such modified fibers, ß-galactosidase activity could be detected using 5-bromo-4-chloro-3-indolyl-ß-D-galactopyranoside (X-Gal) as a substrate.

Example III: Non-Covalent Coupling of a Substance to the Silk Polypeptide $C_{16}$ Coated on an Aramid Fiber In addition to the above mentioned covalent coupling of a substance to spider silk polypeptide $C_{16}$ coated aramid fibers, non-covalent coupling was also performed. A single aramid fiber was incubated for 5 seconds in a formic acid containing 2 wt %/vol of the spider silk polypeptide $C_{16}$ and copper chloride or cobalt chloride at room temperature (25° C.). After separation from the bath and evaporation of the solvent, the cobalt chloride or the copper chloride formed a colored around the aramid fiber coated with the spider silk polypeptide $C_{16}$.

Figure 4:
FIG. 4: Electron microscopy of an untreated already woven fabric and a coated already woven fabric at different magnifications.
Figure 4:
Figure 4:
Figure 4:

Example IV: Coating of a Woven Fabric of Cotton with the Spider Silk Polypeptide $C_{16}$ Not only single fibers but also already woven fabrics are suitable templates for coating with spider silk. An already woven fabric of cotton and a cotton fibre were separately incubated in a 2 wt %/vol spider silk polypeptide $C_{16}$ solution. After drying, the woven fabric of cotton and the cotton fibre showed a comparable coating behaviour (see FIG. 4).

The direct coating of prefabricated fabrics, thus, results in a comparable, but different, coating pattern in comparison to fabrics made out of already silk-coated fibers. With fabric-coating, for example, the interspaces can be coated, whereas otherwise only the fibers and the intersections, but not the interspaces are engulfed by the spider silk coating. This shows that either coating of the fibers before weaving or treating of the already woven fabric results in evenly coated material—suitable for different applications.

Figure 1:
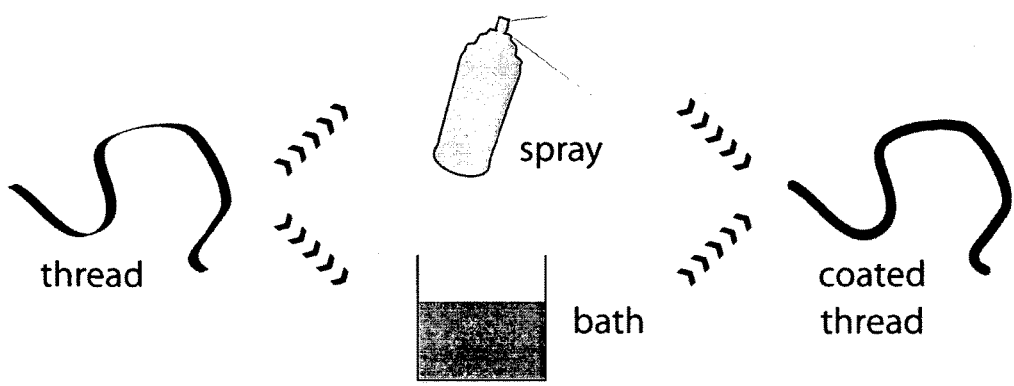
FIG. 1: Technical processes to coat a thread with a silk polypeptide. According to FIG. 1, the silk polypeptide can be applied on a thread via spray coating or via dip coating.

Example V: Dip Coating of an Aramid Thread with the Spider Silk Polypeptide $C_{16}$ To perform the dip coating of an aramid thread with the spider silk polypeptide $C_{16}$, the spider silk polypeptide $C_{16}$ was dissolved in an aqueous solution (10 mM Tris, pH 7.5). The concentration of the silk polypeptide $C_{16}$ in the aqueous solution was 2 wt %/vol. The dip coating procedure (see also FIG. 1) included:
  i) immersion: the aramid thread was immersed in the spider silk polypeptide $C_{16}$ solution at a constant speed of 5 m/s;
  ii) incubation: the substrate was incubated in the coating solution for 2 minutes to allow for the coating material to adhere to the substrate
  iii) withdrawal: the excess of the substrate was removed from the aramid thread at a constant speed of 5 m/s; and
  iv) post treatment: the coating was dried at room temperature (25° C.).

Example VI: Spray Coating of an Aramid Thread with the Spider Silk Polypeptide $C_{16}$ To perform the spray coating of an aramid thread with the spider silk polypeptide $C_{16}$, the spider silk polypeptide $C_{16}$ was dissolved in an aqueous solution (10 mM Tris, pH 7.5). The concentration of the silk polypeptide $C_{16}$ in the aqueous solution was 2 wt %/vol. The spray coating procedure (see also FIG. 1) included:

i) Preparation: the spider silk polypeptide $C_{16}$ solution was transferred into a spray can or spraying device:
ii) Coating: the silk polypeptide $C_{16}$ solution was uniformly distributed onto the aramid thread by the spray can
iii) Post treatment: the coating was dried at room temperature (25° C.).

Example VII: Padding of an Aramid Thread with the Spider Silk Polypeptide $C_{16}$ Spider silk polypeptide $C_{16}$ was dissolved in formic acid. The concentration of the silk polypeptide $C_{16}$ in formic acid was 10 mg/ml. Different types of thread (Teflon (Goodfellow, diameter of fiber: 0.0211 mm), cellulose (Goodfellow, diameter of fiber: 0.015 mm), cotton wool, Kevlar (Goodfellow, diameter of fiber: 0.017 mm), elastane (spandex), untreated human hair and treated (free of dandruff) human hair) have been coated according the dip coating method. Spandex and cotton wool threads have been washed in deionized $H_2O$ and dried before coating. The threads were incubated in the in the spider silk polypeptide $C_{16}$/formic acid solution for 5 seconds to allow for the coating material to adhere to the substrate. The coating was dried at room temperature (25° C.).

Example VIII: Coating of a Nylon Thread with the Spider Silk Polypeptide $C_{16}$ Spider silk polypeptide $C_{16}$ was dissolved in aqueous solution (10 mM Tris pH 7.5). The concentration of the silk polypeptide $C_{16}$ in formic acid was 1 wt %/vol. The nylon thread (Goodfellow, diameter of fiber: 0.01 mm) was incubated in the in the coating solution for 5 seconds to allow for the coating material to adhere to the substrate. The coating was dried at room temperature (25° C.).

Example IX: Coating of a Material with Different Spider Silk Proteins

Different proteins $C_{16}$, $AQ_{24}NR_3$, $C_{16}NR_4$, $AQ_{24}$, $C_8$ and $C_{32}$ were used in order to coat a material (coated glass slide, particularly glass slide coated with a material having a silicium matrix, Sciences Services, Munich, Germany). The coating of a glass slide with different proteins $C_{16}$, $AQ_{24}NR_3$, $C_{16}NR_4$, $AQ_{24}$, $C_8$ and $C_{32}$ has been exemplarily shown with a coated glass slide, particularly glass slide coated with a silicium matrix. The results of the coating of the coated glass slide, particularly glass slide coated with a silicium matrix, with different proteins $C_{16}$, $AQ_{24}NR_3$, $C_{16}NR_4$, $AQ_{24}$, $C_8$ and $C_{32}$ are comparable to the coating of other glass slides (which are not coated, particularly not coated with a material having a silicium matrix) with different proteins $C_{16}$, $AQ_{24}NR_3$, $C_{16}NR_4$, $AQ_{24}$, $C_8$ and $C_{32}$. The final protein concentrations of $C_{16}$, $AQ_{24}NR_3$ and $C_{16}NR_4$ in an aqueous Tris buffered solution were 3%, 0.5%, and 2.1%, respectively. The dip-coating method was used. Said method comprised the following steps: 60 s dipping in the solution, 30 s drying out the solution, re-plunging the material in the solution 30 times and rinsing with purified water (Milli-Q). $AQ_{24}$, $C_8$ and $C_{32}$ were dissolved in formic acid at the concentration of 2%. The spin-coating method was used at 1000 rpm for 1 min. The surface of the coated material (coated glass slide, particularly glass slide coated with a material having a silicium matrix,) was then scratched using a small needle. The height difference between the coating and the raw material was analyzed on different spots using a laser scanning microscope (VK 9700 Keyence, Neu Isenburg, Germany).

Table 1 shows that the material (glass slide) could be homogenously coated with different spider silk proteins. The thickness of the coating depends on the nature of the proteins (hydrophilic & charged), the wettability of the solvent and the coating method.

TABLE 1

| Spider silk protein | Coating | Coating thickness (nm) | Homogeneity |
|---|---|---|---|
| $C_{16}$ | yes | 316 ± 14 | ✓✓ |
| $AQ_{24}NR_3$ | yes | 262 ± 7 | ✓ |
| $C_{16}NR_4$ | yes | 130 ± 21 | ✓ |
| $AQ_{24}$ | yes | 113 ± 10 | ✓ |
| $C_8$ | yes | 66 ± 8 | ✓ |
| $C_{32}$ | yes | 80 ± 8 | ✓ |

(✓✓: highly homogenous coating, ✓: homogenous coating)

Example X: Coating of a Material with the Spider Silk Polypeptide $C_{16}$ Using Different Solvents Different solvents (Tris 100 mM, pH 8; Trifluoroacetic acid; Formic acid; Hexafluoro isopropanol) were used in order to dissolve $C_{16}$ and coat a material (coated glass slide, particularly glass slide coated with a material having a silicium matrix, Sciences Services; Munich, Germany). The coating of a glass slide with different proteins $C_{16}$, $AQ_{24}NR_3$, $C_{16}NR_4$, $AQ_{24}$, $C_8$ and $C_{32}$ has been exemplarily shown with a coated glass slide, particularly glass slide coated with a silicium matrix. The results of the coating of the coated glass slide, particularly glass slide coated with a silicium matrix, with different proteins $C_{16}$, $AQ_{24}NR_3$, $C_{16}NR_4$, $AQ_{24}$, $C_8$ and $C_{32}$ are comparable to the coating of other glass slides (which are not coated, particularly not coated with a material having a silicium matrix) with different proteins $C_{16}$, $AQ_{24}NR_3$, $C_{16}NR_4$, $AQ_{24}$, $C_8$ and $C_{32}$. For the coating, an aqueous solution (Tris (100 mM, pH 8) was used. The final protein concentration of $C_{16}$ in said solution was 3%. The dip-coating method was used. Said method comprised the following steps: 60 s dipping in the solution, 30 s drying out the solution, re-plunging the material in the solution 30 times and rinsing with millipore water. $C_{16}$ was also dissolved directly in Trifluoroacetic acid, Formic acid and Hexafluoro isopropanol at a final concentration of 1%. The spin-coating method was used at 1000 rpm for 1 min. The surface of the coated material (coated glass slide, particularly glass slide coated with a material having a silicium matrix,) was then scratched using a small needle. The height difference between the coating and the raw material was analyzed on different spots using a laser scanning microscope (VK 9700 Keyence, Neu-Isenburg, Germany).

Table 2 shows that the material (glass slide) could be coated with $C_{16}$. The thickness depends on the nature of the protein, the wettability of the solvent and the coating method.

TABLE 2

| Solvent | Coating | Coating thickness (nm) | Homogeneity |
|---|---|---|---|
| Tris 100 mM, pH 8 | yes | 316 ± 14 | ✓✓ |
| Trifluoroacetic acid | yes | 134 ± 8 | ✓ |
| Formic acid | yes | 44 ± 3 | ✓✓ |
| Hexafluoroisopropanol | yes | 53 ± 14 | ✓ |

(✓✓: highly homogenous coating, ✓: homogenous coating)

Example XI: Coating of Naturally Occurring Materials with $C_{16}$ $C_{16}$ and $AQ_{24}NR_3$ were used to coat different naturally occurring materials (organic materials) such as human hair, cotton ("Obergarn" fiber), rubber, wool and cellulose (Goodfellow d=0.015 mm, Huntington, Great Britain). European blond bleached hair was drop-coated using an aqueous solution of $C_{16}$ in Tris buffer (100 mM, pH 8) at a protein concentration of 3% until drying and rinsed with purified water (Milli Q). European virgin hair was drop-coated using a solution of $AQ_{24}NR_3$ dissolved in purified water (Milli Q) at a protein concentration of 0.85% until drying. Cotton, rubber, wool and cellulose were coated using an aqueous solution of $C_{16}$ in Tris buffer (100 mM, pH 8) at a protein concentration of 1.35%. The dip-coating method was used. Said method comprised the following steps: 120 s dipping in the solution, 120 s drying out the solution, re-plunging the material in the solution 10 times and rinsing with purified water (Milli Q). Each coated fiber (coating) was compared to a non-coated reference fiber (reference). The radii of the coated fiber and the non-coated fiber of human hair, cotton, wool and cellulose were compared to quantify the thickness of the coating. The coatings were analyzed on different spots using a laser scanning microscope (VK 9700 Keyence; Neu-Isenburg, Germany). The results are summarized in Table 3.

TABLE 3

| Material | Coating | Radius Reference (μm) | Radius Coating (μm) | Coating thickness (μm) | Roughness Ra*(μm) Coating | Roughness Ra*(μm) Reference | Homogeneity |
|---|---|---|---|---|---|---|---|
| Treated Hair | yes | 30.8 | 34.25 | 3.45 | 0.287 | 0.32 | ✓ |
| Virgin Hair | yes | 35 | 38.7 | 3.7 | 0.256 | 0.371 | ✓ |
| Cotton | yes | | | ~2.45 | | | x |
| Rubber | yes | | | | | | ✓ |
| Wool | yes | 10.7 ± 0.5 | 11.8 ± 0.3 | 1 | | | ✓ |
| Cellulose | yes | 9.42 ± 0.1 | 12.7 ± 0.1 | 3.27 | | | x |

(*Ra: arithmetic middle height; ✓✓: highly homogenous coating, ✓: homogenous coating; x: slightly homogenous coating)

Table 3 shows the coating of different naturally occurring materials (organic materials). The materials showed an increased thickness after coating. Treated and Virgin hair showed a decrease in roughness. Cotton fibers rolled together to form a bigger fiber. Therefore, it was difficult to image a single fiber and estimate the diameter difference. Although the thickness could not be exactly estimated as the fibers did not have a constant diameter over their whole length, the coating was clearly visible. Wool could be coated homogeneously with $C_{16}$. Cellulose could be coated with $C_{16}$. Because of the characteristics of cellulose, no homogenous coating could be detected by the coating method in this experiment. As cellulose is not a round smooth fiber, the coating was not thick enough to be homogeneous. However, an increase of the coating cycle number can increase the homogeneity of the coating.

Figure 5:
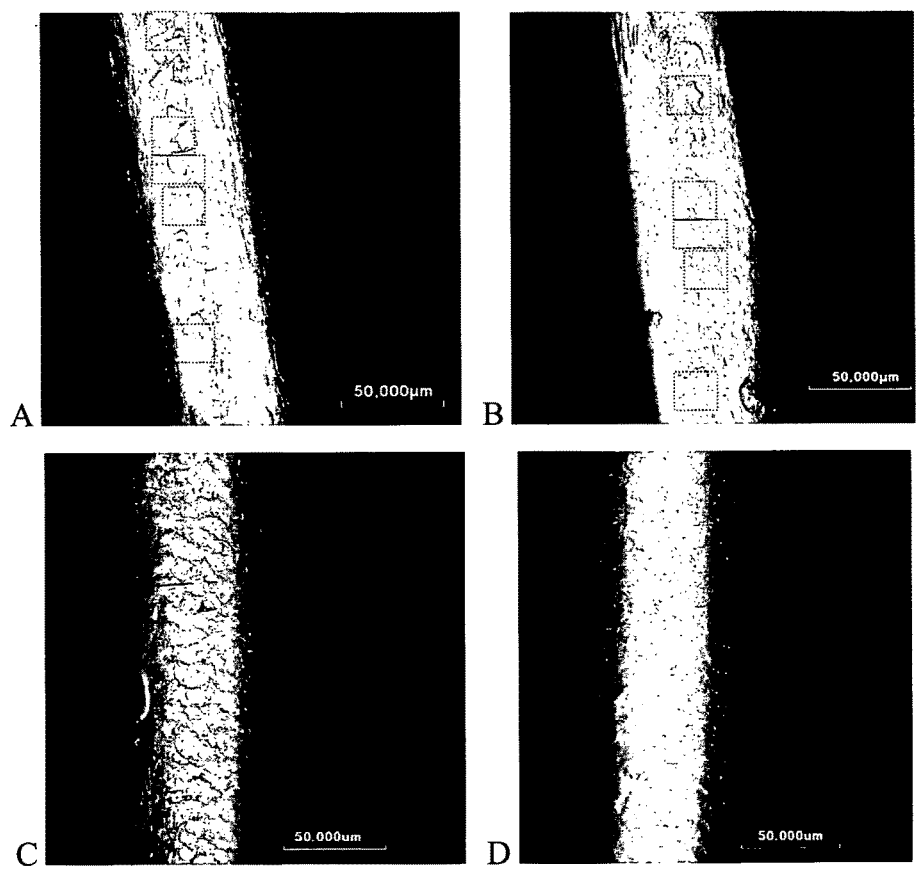
FIG. 5: Laser scanning microscope image (laser-intensity-magnification 50×) of a European blond bleached hair (A, B), before (A) and after coating (B) with spider silk polypeptide $C_{16}$ (3%) and of a virgin European hair (C, D), before (C) and after (D) coating with $AQ_{24}NR_3$ (0.85%). The quadrates shown in FIG. 5 A and FIG. 5 B designate specific distinctive spots on the hair sample to allow comparison of the same section of the hair sample before and after coating.

Laser scanning images in FIG. 5 show differences in the coating of hair keratin fibers. For both bleached and virgin hair, the cuticles disappeared under the coatings and the fiber surfaces were more homogeneous. The roughness decreased with the thickness of the coating. The addition of material smoothed the hair fibers. The light reflection could be measured as laser intensity. For the reference bleached hair, the average value over the full length was 13198 and for the coated hair the average value was about 13632 (over 16384 grey steps). For the virgin hair, the reference average value was about 13517, while the average value for coated hair was 13746. The laser intensity is specified in grey steps. The minimum represents the value 0 and the maximum represents the value 16384. The higher the value the higher the reflection/brilliance of the sample/material. In case of bleached hair and virgin hair, the value for the coated hair was higher compared to a reference, respectively. The coating enhanced the brilliance of the fibers.

Example XII: Coating of Inorganic Inert Materials with Spider Silk Polypeptide $C_{16}$ $C_{16}$ was used to coat different inorganic inert materials such as glass (glass slide, Roth; Karlsruhe, Germany), carbon (carbon fiber plate, R&G GmbH) and metal (metal plate). For the glass slide, $C_{16}$ was dissolved directly in formic acid (final protein concentration 1%). The spin-coating method was used at 1000 rpm for 1 min. For the carbon and metal plate, the coating was performed with $C_{16}$ in an aqueous solution (Tris 100 mM, pH 8). The final concentration was 1.35%. The dip-coating method for the carbon plate comprised the following steps: 120 s dipping in the solution, 120 s drying out the solution, re-plunging the material in the solution 10 times and rinsing with millipore water. The dip-coating method for the metal plate comprised the following steps: 120 s dipping in the solution, 120 s drying out the solution, re-plunging the material in the solution, 1000 times, and rinsing with purified water (Milli Q). The surface of the coated material (metal plate, carbon plate) was then scratched using a small needle. The surface of the coated material (metal plate, carbon plate) was analyzed on different spots using a laser scanning microscope (VK 9700 Keyence, Neu-Isenburg, Germany). Coated and non-coated materials were compared. The height difference between the coating and the raw material estimated the thickness of the coating. The coating smoothed the substrate surface. The results are summarized in Table 4.

TABLE 4

| Inorganic inert material | Coating | Coating thickness (nm) | Roughness* (nm) | | Homogeneity |
|---|---|---|---|---|---|
| | | | Coating | Reference | |
| Glass | yes | 76.5 ± 11 | Ra = 18<br>Rq = 22 | Ra = 30<br>Rq = 37 | ✓ |
| Carbon fiber plate | yes | | | | x |
| Metal plate | yes | | | | x |

(*Roughness: Ra: arithmetic middle height; Rq: quadratic height average, ✓: homogenous coating; x: slightly homogenous coating)

Table 4 shows the thickness of the $C_{16}$ coating on inorganic materials. Glass, carbon and metal could be coated. In case of glass, homogenous coating could be detected. Coated glass showed a decreased roughness compared to non-coated glass (reference).

Example XIII: Coating of Synthetic Inert Materials with Spider Silk Polypeptide $C_{16}$ $C_{16}$ was used to coat different synthetic inert materials such as polyester (PET, Syngarn fiber), polyamide (PA, Good fellow d=0.01 mm), polytetrafluorethylene (PTFE, Good Fellow d=0.0211 mm), polypropylene (PP, Good Fellow plate), ultra high molecular weight polyethylene (UHMW PE, Good Fellow plate), elastane and polyaramid. The coating of polyester, polyamide, PTFE, polypropylene, UHMW polyethylene was performed with $C_{16}$ in an aqueous solution (Tris 100 mM, pH 8). The final protein concentration was 1.35%. The dip-coating method was used. Said method comprised the following steps: 60 s dipping in the solution, 30 s drying out the solution, and re-plunging the sample in the solution 30 times and rinsing with millipore water. Elastane and polyaramid were coated using a solution of $C_{16}$ in Tris buffer (100 mM, pH 8) with a final protein concentration of 14%. The fibers were dipped 3 times in the solution and rinsed with millipore water. Each material was compared to a non-coated reference. PE, PA, PTFE, elastane, and polyaramid were in form of a fiber. The radius of the fiber can be compared to estimate the thickness of the coating. It was not possible to estimate the coating thickness over the whole length of the fiber. Thus, the fibers were analyzed on different spots using a laser scanning microscope (VK 9700 Keyence, Neu-Isenburg, Germany). The results are shown in Table 5.

TABLE 5

| Synthetic inert material | Coating | Radius ref (μm) | Radius coated (μm) | Coating thickness (μm) | Homogeneity |
|---|---|---|---|---|---|
| PET | yes | 4.7 ± 0.4 | 5.8 ± 0.4 | 1.16 | ✓ |
| PA | yes | 5 ± 0.02 | 5.75 ± 0.3 | 0.74 | x |
| PTFE | yes | 5.4 ± 0.05 | 9.7 ± 0.5 | 4.3 | x |
| PP | yes | | | | ✓ |
| UHMW PE | yes | | | | |
| Elastane | yes | 299.3 ± 3 | 348.8 ± 40 | 49.5 | ✓ |
| Polyaramid | yes | 79 ± 1 | 84 ± 1 | 5 | x |

Figure 6:
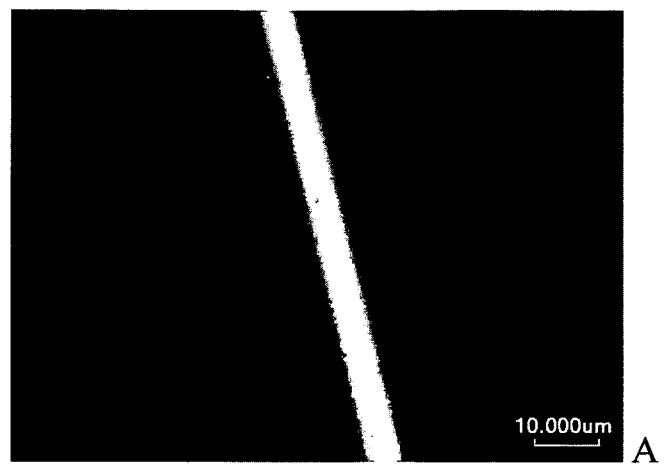
FIG. 6: Laser scanning microscope images (Laser-intensity-Magnification 150×) of nylon (PA) fiber before (A) and after coating (B) with C16 (3%).
Figure 6:
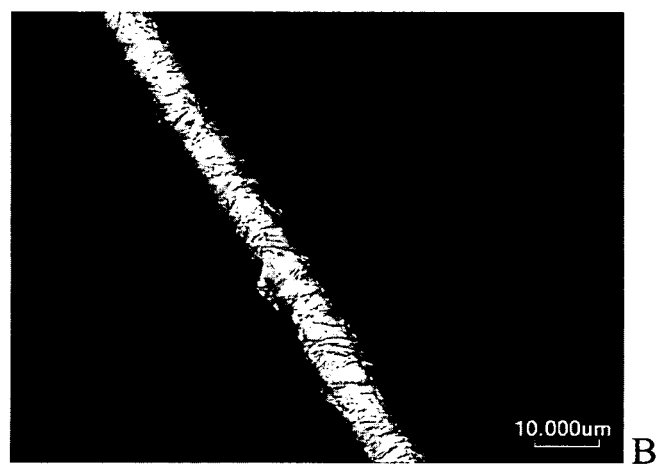

Table 5 shows the thickness of the $C_{16}$ coating on synthetic inert materials. All materials could be coated. In case of PET, PA, PTFE, elastane, and polyaramid, an increase in the thickness of the coated synthetic inert material compared to the non-coated reference was detected. In case of PTFE fibers, the coating was slightly homogeneous. The coating thickness value of 4.3 μm is an average. For PP and UHMW PE plates, a coating could be clearly detected. Elastane consists of many fibers which are rolled together. Thus, the measured thickness value represents the coating thickness on several fibers which are rolled together. The coating of the smooth surface of the polyamid (PA) fiber resulted in a less homogenous surface. This is shown by laser scanning microscope images (FIG. 6) of a polyamid (PA, nylon) fiber. A fiber before (FIG. 6 A) and after coating (FIG. 6 B) with $C_{16}$ is shown. The coating was detectable all over the fiber. After coating, the fiber surface was less homogeneous (FIG. 6 B).

Figure 7:
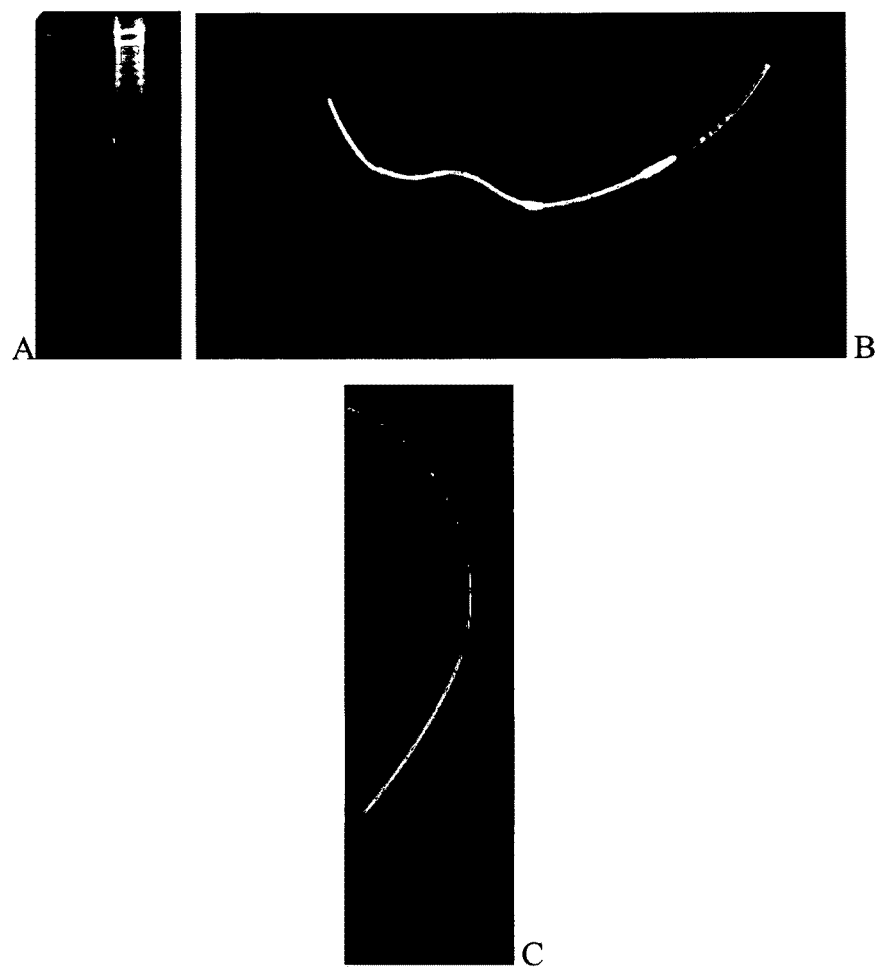
FIG. 7: Fluorescence images (Proxima-Imager) under fluorescence light (EpiVex) and Cy5 filter.

Example XIV: Coating of Human Hair with $AQ_{24}NR_3$ Crosslinked with a Cy5 Fluorescent Tag A solution of $AQ_{24}NR_3$ (protein concentration 4 mg/ml) in guanidine thiocyanate (5 M) was prepared and dialyzed against Tris buffer 100 mM at pH 8 resulting in a protein solution at 1 mg/ml (the coating with this protein is shown in FIG. 7 B). In a further experiment, a solution of $AQ_{24}NR_3$ (protein concentration 2 mg/ml) in 5 M Urea was prepared and dialyzed against 100 mM Tris buffer, at pH 8 (the coating with this protein is shown in FIG. 7 C). The protein solution was labeled with Amersham™ Cy™5 Maleimide Mono-Reactive Dye (GE Healthcare, cat. no. PA25031). The bioconjugation with the fluorescent tag was done using the cysteine sulphydryl group (one per molecule). A solution of TCEP (10 μL, Tris(2-carboxyethyl)phosphine) at 18 mg/ml in Tris, pH 7), used to reduce the disulphide bonds, was added to the protein solution. The protein solution was incubated for 10 min at room temperature (RT). The dye solution of Cy5-maleimide (GE Healthcare) was mixed with 50 μL of anhydrous Dimethyformamide (DMF); 40 μL was added to the protein solution. The solution was incubated for 2 hours at RT and overnight at 4° C. The protein solution (3 μg) was used directly for western-blot analysis.

An untreated human hair was plunged in the protein solution for 10 min and rinsed with pure water (milli Q) (FIG. 7 B). The tip of an Indian hair was plunged in the labeled protein solution for 10 min and then air-dried (FIG. 7 C). The hair and the gel were imaged using Proxima with Epi-Vex light and Cy5 filter (FIG. 7 A). On the western-blot gel, labeled $AQ_{24}NR_3$ protein and non-labeled $AQ_{24}NR_3$ protein were compared. Only the labeled protein can be detected under the Cy5 filter. As a result, the fluorescent labeled protein emitted light, while the non-labeled could not be seen. The proteins were covalently bound to the fluorescent dye. Silk in solution can be chemically modified using the different addressable amino groups. Cy5-labeled $AQ_{24}NR_3$ protein can be used to coat different substrates, such as hair, without altering the coating characteristics as well as the fluorescence characteristics. The hair coating is visible under Cy5-filter (FIG. 7).

As a general conclusion, the experiments show exemplarily that the method of the present invention allows coating of synthetic inert materials, inorganic inert materials, and naturally occurring materials. The coating homogeneity depends on the chemical nature of the silk (hydrophilicity and charges), the chemical nature of the material, the geometry of the material, the chosen solvent and the coating method. Chemically modified silk protein can also be coated on different substrates.

Example XV: Coating of Human Indian and Human Virgin Hair with $AQ_{24}NR_3$

The experiment shows the effects of protein-coating on European virgin hair (never treated with chemicals) and Indian hair (treated with chemicals; used for extensions). The protein $AQ_{24}NR_3$ was used in different protein concentrations for the treatment of hair. For a 0.2% protein solution, $AQ_{24}NR_3$ was dissolved in 5 M Urea and dialyzed against pure water (Milli Q). For a 0.6% and 0.85% protein solution, $AQ_{24}NR_3$ was directly dissolved in pure water (Milli Q) without any dialyzing step. The European virgin hair or the Indian hair was plunged for about 10 min in the above mentioned protein solutions and then air-dried. Exactly the same spot on the European virgin hair or the Indian hair (marked by adhesive strip and permanent marker) was analyzed before and after treatment with the above mentioned protein solutions using a laser scanning microscope (VK 9700 Keyence; Neu Isenburg, Germany).

The results are shown in Tables 6 to 9. The analysis was performed with a VK Analyzer of Keyence.

TABLE 6

Thickness coating on Indian hair

| Conditioner concentration | Radius untreated hair [μm] | Radius treated hair [μm] | Coating thickness [μm] |
| --- | --- | --- | --- |
| 0.2% | 30.3 | 31.8 | 1.5 |
| 0.6% | 35 | 37.7 | 2.7 |
| 0.85% | 34.3 | 37.1 | 2.8 |

TABLE 7

Average surface roughness (Ra) of Indian hair

| Conditioner concentration | Ra untreated hair [μm] | Ra treated hair [μm] | Roughness reduction [μm] |
| --- | --- | --- | --- |
| 0.2% | 0.271 | 0.149 | 0.122 |
| 0.6% | 0.531 | 0.264 | 0.267 |
| 0.85% | 0.525 | 0.149 | 0.376 |

TABLE 8

Thickness coating on European virgin hair

| Conditioner concentration | Radius untreated hair [μm] | Radius treated hair [μm] | Coating thickness [μm] |
| --- | --- | --- | --- |
| 0.2% | 28.2 | 29.7 | 1.5 |
| 0.6% | 35.7 | 38.7 | 3 |
| 0.85% | 35 | 38.7 | 3.7 |

TABLE 9

Average surface roughness (Ra) of European virgin hair

| Conditioner concentration | Ra untreated hair [μm] | Ra treated hair [μm] | Roughness reduction [μm] |
| --- | --- | --- | --- |
| 0.2% | 0.5213 | 0.415 | 0.098 |
| 0.6% | 0.894 | 0.781 | 0.113 |
| 0.85% | 0.371 | 0.256 | 0.115 |

An increase of the concentration of the protein-solution (i.e. from 0.2% to 0.85%) resulted in an increase of the radius of the coated hair. The roughness of the hair surface decreased with the increasing thickness of the coating. In addition, the smoothness of the hair surface increased with the increasing thickness of the coating.

Example XVI: Coating of Human Skin with Spider Silk Protein $C_{16}$

Figure 8:
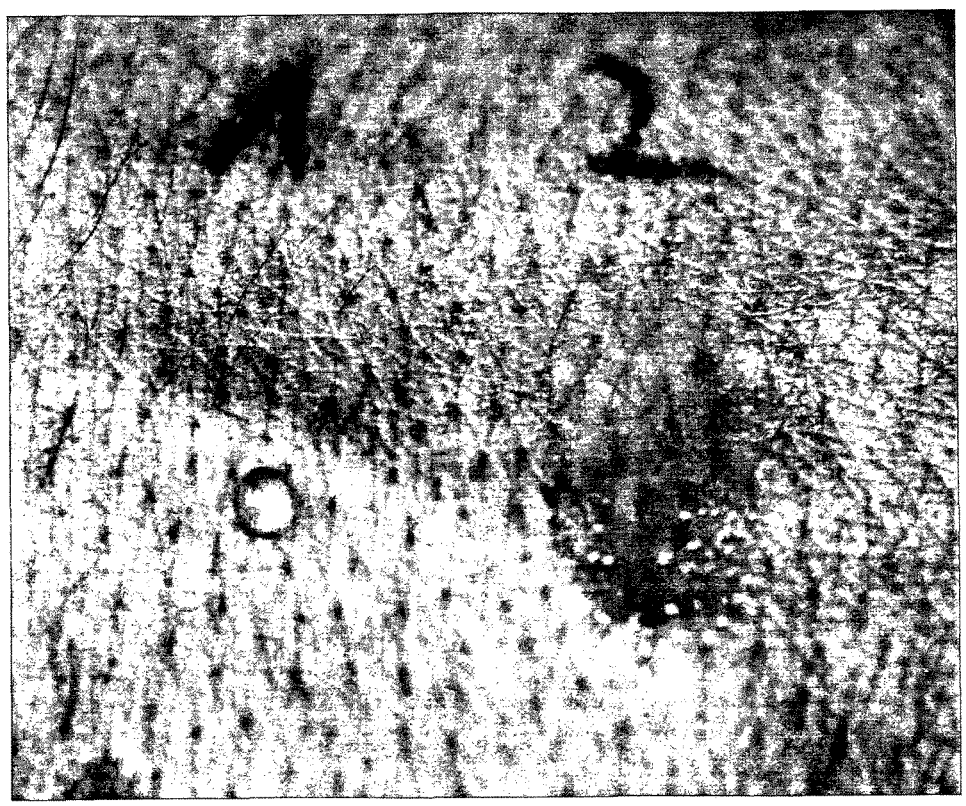
FIG. 8: Untreated human skin (FIG. 8 A) and human skin after coating with silk protein (FIG. 8 B). After coating with silk protein, the hydrophobicity of the skin was significantly decreased, resulting in a much higher wetting behavior of the water droplet

Untreated human skin (FIG. 8 A) and human skin after coating with silk protein (FIG. 8 B). A water droplet (dyed, for clarification) normally does not wet human skin due to the hydrophobic nature of intact skin. After coating with a silk protein, the hydrophobicity of the skin was significantly decreased, resulting in a much higher wetting behavior of the water droplet.

In detail, a solution of the spider silk protein $C_{16}$ (1 mg/ml) in Urea (5%) was prepared. After washing the skin of a hand with a sodium lauryl sulfate free soap and subsequent air drying, 40 μl of the protein-Urea solution (B) and 40 μl of a Urea (5%) control solution (without protein) (A) were applied on a defined skin area (see FIG. 8). The silk coating results in a continuous invisible film which increases the hydrophilic properties of skin and effects protection of skin. After drying 40 μl pure water was applied on the skin (FIG. 8). Due to the increase of hydrophilic properties of the silk coated skin, water was able to permeate immediately into the skin (FIG. 8 B), whereas the water drop in FIG. 8 A did not permeate the uncoated skin. FIG. 8 B (silk coated skin) shows a water drop spread over a large area in contrast to FIG. 8 A (uncoated skin) showing a distinct water drop. The protective properties of the coated invisible film resisted several cycles of washing with water/soap and drying.

The invention claimed is:

1. A method of coating a polypropylene (PP) material with a recombinant spider silk polypeptide which comprises the steps of:
   i) providing a solution which comprises at least one recombinant spider silk polypeptide comprising at least two identical repetitive units and a solvent, and
   ii) applying the solution on the polypropylene (PP) material and thereby coating the polypropylene (PP) material with the recombinant spider silk polypeptide.

2. The method of claim 1, wherein the recombinant spider silk polypeptide comprises at least two identical repetitive units each comprising at least one consensus sequence selected from the group consisting of:
   i) GPGXX (SEQ ID NO: 3), wherein each X is an amino acid, independently selected from A, S, G, Y, P, and Q;
   ii) GGX, wherein X is an amino acid selected from Y, P, R, S, A, T, N and Q; and
   iii) Ax, wherein x is an integer from 5 to 10.

3. The method of claim 2, wherein the repetitive units are independently selected from module A (SEQ ID NO: 20), module C (SEQ ID NO: 21), module Q (SEQ ID NO: 22), module K (SEQ ID NO: 23), module sp (SEQ ID NO: 24), module S (SEQ ID NO: 25), module R (SEQ ID NO: 26), module X (SEQ ID NO: 27) or module Y (SEQ ID NO: 28), or variants thereof.

4. The method of claim 1, wherein the recombinant spider silk polypeptide further comprises at least one non-repetitive (NR) unit.

5. The method of claim 1, wherein the polypropylene (PP) material is selected from the group consisting of a fiber, a thread comprising a fiber, a twisted yarn comprising a fiber, a woven fabric comprising a fiber and a non-woven fabric comprising a fiber.

6. The method of claim 1, wherein the recombinant spider silk polypeptide in the coating is linked to the polypropylene (PP) material via at least one of a covalent link and a non-covalent link.

7. The method of claim 6, wherein the recombinant spider silk polypeptide is covalently linked
   (a) via at least one of a cysteine residue, a lysine residue, an amino terminus, a carboxy terminus, and an amino or carboxy terminal TAG of the spider silk polypeptide; or
   (b) via a crosslink
   to the polypropylene (PP) material.

8. The method of claim 6, wherein the recombinant spider silk polypeptide is non-covalently linked via at least one of an ionic linkage and a hydrophobic linkage to the polypropylene (PP) material.

9. The method of claim 1, wherein the recombinant spider silk polypeptide further comprises at least one substance which is linked to the recombinant silk polypeptide by at least one of a covalent link and a non-covalent link.

10. The method of claim 9, wherein the substance is covalently linked
    (a) via at least one of a cysteine residue, a lysine residue, an amino terminus, a carboxy terminus, and an amino or carboxy terminal TAG of the spider silk polypeptide; or
    (b) via a crosslink
    to the recombinant spider silk polypeptide.

11. The method of claim 9, wherein the substance is non-covalently linked via at least one of an ionic linkage and a hydrophobic linkage to the recombinant spider silk polypeptide.

12. The method of claim 1, wherein the method further comprises the steps of:
    iii) providing a solution which comprises at least one recombinant spider silk polypeptide comprising at least two identical repetitive units, and optionally at least one non-repetitive (NR) unit, and a solvent, and
    iv) applying the solution on the polypropylene (PP) material and thereby coating for the second time the polypropylene (PP) material with the recombinant spider silk polypeptide, wherein the recombinant spider silk polypeptide of step (iii) is identical or different to the spider silk polypeptide of step (i).

13. The method of claim 12, wherein steps (iii) and (iv) are repeated several times to obtain a coated polypropylene (PP) material of different thickness and multiple layers.

14. The method of claim 1, wherein the method comprises subsequently to step ii), a step for post-modifying the coated polypropylene (PP) material.

15. A method of coating a synthetic inert or naturally occurring material with a recombinant silk polypeptide which comprises the steps of:
    i) providing a solution which comprises at least one recombinant silk polypeptide comprising at least two identical repetitive units and a solvent, and
    ii) applying the solution on the synthetic inert material or on the naturally occurring material and thereby coating the synthetic inert material or the natural occurring material with the recombinant silk polypeptide,
    wherein the recombinant silk polypeptide is non-covalently linked via at least one of an ionic linkage and a hydrophobic linkage to the synthetic inert material or naturally occurring material, and
    wherein the synthetic inert material is selected from the group consisting of polypropylene (PP) and polytetrafluorethylene (PTFE), or
    wherein the naturally occurring material is selected from the group consisting of skin and hair.

16. A method of coating a polypropylene (PP) material with a recombinant spider silk polypeptide, comprising the steps of:
    i) providing a solution essentially consisting of at least one recombinant spider silk polypeptide comprising at least two identical repetitive units and a solvent, and ii) applying the solution on the polypropylene material and thereby coating the polypropylene material with the recombinant spider silk polypeptide.

17. A coated polypropylene (PP) material obtainable by the method of claim 1.

18. A fiber comprising the polypropylene (PP) material of claim 17.

19. A thread comprising the fiber of claim 18.

20. A twisted yarn, a woven fabric or a non-woven fabric comprising the fiber of claim 18.

21. A polypropylene (PP) material coated with a recombinant spider silk polypeptide.

22. A fiber comprising the polypropylene (PP) material of claim 21.

23. A thread comprising the fiber of claim 22.

24. A twisted yarn, a woven fabric or a non-woven fabric comprising the fiber of claim 22.

* * * * *

SEQUENCE LISTING

<160> NUMBER OF SEQ ID NOS: 44

<210> SEQ ID NO 1
<211> LENGTH: 636
<212> TYPE: PRT
<213> ORGANISM: Araneus diadematus
<220> FEATURE:
<221> NAME/KEY: PEPTIDE
<222> LOCATION: (1)..(636)
<223> OTHER INFORMATION: ADF-3

```
<400> SEQUENCE: 1

Ala Arg Ala Gly Ser Gly Gln Gln Gly Pro Gly Gln Gln Gly Pro Gly
1               5                   10                  15

Gln Gln Gly Pro Gly Gln Gln Gly Pro Tyr Gly Pro Gly Ala Ser Ala
            20                  25                  30

Ala Ala Ala Ala Ala Gly Gly Tyr Gly Pro Gly Ser Gly Gln Gln Gly
        35                  40                  45

Pro Ser Gln Gln Gly Pro Gly Gln Gln Gly Pro Gly Gln Gln Gly Pro
    50                  55                  60

Tyr Gly Pro Gly Ala Ser Ala Ala Ala Ala Ala Gly Gly Tyr Gly
65              70                  75                  80

Pro Gly Ser Gly Gln Gln Gly Pro Gly Gln Gln Gly Pro Tyr Gly Pro
            85                  90                  95

Gly Ser Ser Ala Ala Ala Ala Ala Gly Gly Asn Gly Pro Gly Ser
                100                 105                 110

Gly Gln Gln Gly Ala Gly Gln Gln Gly Pro Gly Gln Gln Gly Pro Gly
            115                 120                 125

Ala Ser Ala Ala Ala Ala Ala Gly Gly Tyr Gly Pro Gly Ser Gly
    130                 135                 140

Gln Gln Gly Pro Gly Gln Gln Gly Pro Gly Gln Gln Gly Pro Tyr Gly
145             150                 155                 160

Pro Gly Ala Ser Ala Ala Ala Ala Ala Gly Gly Tyr Gly Pro Gly
            165                 170                 175

Ser Gly Gln Gly Pro Gly Gln Gln Gly Pro Gly Gln Gln Gly Pro Tyr
        180                 185                 190

Gly Pro Gly Ala Ser Ala Ala Ala Ala Ala Gly Gly Tyr Gly Pro
    195                 200                 205

Gly Ser Gly Gln Gln Gly Pro Gly Gln Gln Gly Pro Gly Gln Gln Gly
    210                 215                 220

Pro Gly Gly Gln Gly Pro Tyr Gly Pro Gly Ala Ser Ala Ala Ala Ala
225             230                 235                 240

Ala Ala Gly Gly Tyr Gly Pro Gly Tyr Gly Gln Gln Gly Pro Gly Gln
            245                 250                 255

Gln Gly Pro Gly Gly Gln Gly Pro Tyr Gly Pro Gly Ala Ser Ala Ala
        260                 265                 270

Ser Ala Ala Ser Gly Gly Tyr Gly Pro Gly Ser Gly Gln Gln Gly Pro
    275                 280                 285

Gly Gln Gln Gly Pro Gly Gln Gly Pro Tyr Gly Pro Gly Ala Ser
    290                 295                 300

Ala Ala Ala Ala Ala Ala Gly Gly Tyr Gly Pro Gly Ser Gly Gln Gln
305             310                 315                 320

Gly Pro Gly Gln Gln Gly Pro Gly Gln Gln Gly Pro Gly Gln Gln Gly
            325                 330                 335

Pro Gly Gly Gln Gly Pro Tyr Gly Pro Gly Ala Ser Ala Ala Ala Ala
            340                 345                 350

Ala Ala Gly Gly Tyr Gly Pro Gly Ser Gly Gln Gln Gly Pro Gly Gln
            355                 360                 365

Gln Gly Pro Gly Gln Gln Gly Pro Gly Gln Gln Gly Pro Gly Gln Gln
        370                 375                 380

Gly Pro Gly Gln Gln Gly Pro Gly Gln Gln Gly Pro Gly Gln Gln Gly
385             390                 395                 400

Pro Gly Gln Gln Gly Pro Gly Gly Gln Gly Ala Tyr Gly Pro Gly Ala
```

```
                405                 410                 415
Ser Ala Ala Gly Ala Ala Gly Gly Tyr Gly Pro Gly Ser Gly Gln
            420                 425                 430

Gln Gly Pro Gly Gln Gln Gly Pro Gly Gln Gln Gly Pro Gly Gln
        435                 440                 445

Gly Pro Gly Gln Gln Gly Pro Gly Gln Gln Gly Pro Gly Gln Gln Gly
    450                 455                 460

Pro Gly Gln Gln Gly Pro Tyr Gly Pro Gly Ala Ser Ala Ala Ala
465                 470                 475                 480

Ala Ala Gly Gly Tyr Gly Pro Gly Ser Gly Gln Gln Gly Pro Gly Gln
            485                 490                 495

Gln Gly Pro Gly Gln Gln Gly Pro Gly Gln Gly Pro Tyr Gly Pro
        500                 505                 510

Gly Ala Ala Ser Ala Ala Val Ser Val Gly Gly Tyr Gly Pro Gln Ser
    515                 520                 525

Ser Ser Val Pro Val Ala Ser Ala Val Ala Ser Arg Leu Ser Ser Pro
    530                 535                 540

Ala Ala Ser Ser Arg Val Ser Ser Ala Val Ser Ser Leu Val Ser Ser
545                 550                 555                 560

Gly Pro Thr Lys His Ala Ala Leu Ser Asn Thr Ile Ser Ser Val Val
            565                 570                 575

Ser Gln Val Ser Ala Ser Asn Pro Gly Leu Ser Gly Cys Asp Val Leu
        580                 585                 590

Val Gln Ala Leu Leu Glu Val Val Ser Ala Leu Val Ser Ile Leu Gly
    595                 600                 605

Ser Ser Ser Ile Gly Gln Ile Asn Tyr Gly Ala Ser Ala Gln Tyr Thr
    610                 615                 620

Gln Met Val Gly Gln Ser Val Ala Gln Ala Leu Ala
625                 630                 635

<210> SEQ ID NO 2
<211> LENGTH: 410
<212> TYPE: PRT
<213> ORGANISM: Araneus diadematus
<220> FEATURE:
<221> NAME/KEY: PEPTIDE
<222> LOCATION: (1)..(410)
<223> OTHER INFORMATION: ADF-4

<400> SEQUENCE: 2

Ala Gly Ser Ser Ala Ala Ala Ala Ala Ser Gly Ser Gly Gly
1               5                   10                  15

Tyr Gly Pro Glu Asn Gln Gly Pro Ser Gly Pro Val Ala Tyr Gly Pro
            20                  25                  30

Gly Gly Pro Val Ser Ser Ala Ala Ala Ala Ala Gly Ser Gly
        35                  40                  45

Pro Gly Gly Tyr Gly Pro Glu Asn Gln Gly Pro Ser Gly Pro Gly Gly
    50                  55                  60

Tyr Gly Pro Gly Gly Ser Gly Ser Ser Ala Ala Ala Ala Ala Ala
65                  70                  75                  80

Ala Ser Gly Pro Gly Gly Tyr Gly Pro Gly Ser Gln Gly Pro Ser Gly
            85                  90                  95

Pro Gly Gly Ser Gly Gly Tyr Gly Pro Gly Ser Gln Gly Ala Ser Gly
        100                 105                 110

Pro Gly Gly Pro Gly Ala Ser Ala Ala Ala Ala Ala Ala Ala
    115                 120                 125
```

-continued

```
Ala Ser Gly Pro Gly Gly Tyr Gly Pro Gly Ser Gln Gly Pro Ser Gly
    130                 135                 140

Pro Gly Ala Tyr Gly Pro Gly Gly Pro Gly Ser Ser Ala Ala Ala Ala
145                 150                 155                 160

Ala Ala Ala Ala Ser Gly Pro Gly Gly Tyr Gly Pro Gly Ser Gln Gly
                165                 170                 175

Pro Ser Gly Pro Gly Val Tyr Gly Pro Gly Gly Pro Gly Ser Ser Ala
            180                 185                 190

Ala Ala Ala Ala Ala Gly Ser Gly Pro Gly Gly Tyr Gly Pro Gly Glu
        195                 200                 205

Asn Gln Gly Pro Ser Gly Pro Gly Gly Tyr Gly Pro Gly Gly Ser Gly
    210                 215                 220

Ser Ser Ala Ala Ala Ala Ala Ala Ala Ser Gly Pro Gly Gly Tyr
225                 230                 235                 240

Gly Pro Gly Ser Gln Gly Pro Ser Gly Pro Gly Gly Ser Gly Gly Tyr
                245                 250                 255

Gly Pro Gly Ser Gln Gly Gly Ser Gly Pro Gly Ala Ser Ala Ala Ala
            260                 265                 270

Ala Ala Ala Ala Ala Ser Gly Pro Gly Gly Tyr Gly Pro Gly Ser Gln
        275                 280                 285

Gly Pro Ser Gly Pro Gly Tyr Gln Gly Pro Ser Gly Pro Gly Ala Tyr
    290                 295                 300

Gly Pro Ser Pro Ser Ala Ser Ala Ser Val Ala Ala Ser Val Tyr Leu
305                 310                 315                 320

Arg Leu Gln Pro Arg Leu Glu Val Ser Ser Ala Val Ser Ser Leu Val
                325                 330                 335

Ser Ser Gly Pro Thr Asn Gly Ala Ala Val Ser Gly Ala Leu Asn Ser
                340                 345                 350

Leu Val Ser Gln Ile Ser Ala Ser Asn Pro Gly Leu Ser Gly Cys Asp
            355                 360                 365

Ala Leu Val Gln Ala Leu Leu Glu Leu Val Ser Ala Leu Val Ala Ile
        370                 375                 380

Leu Ser Ser Ala Ser Ile Gly Gln Val Asn Val Ser Ser Val Ser Gln
385                 390                 395                 400

Ser Thr Gln Met Ile Ser Gln Ala Leu Ser
                405                 410

<210> SEQ ID NO 3
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: REPEAT
<222> LOCATION: (1)..(5)
<223> OTHER INFORMATION: consensus peptide motif
<220> FEATURE:
<221> NAME/KEY: MOD_RES
<222> LOCATION: (4)..(5)
<223> OTHER INFORMATION: Xaa is any amino acid
<220> FEATURE:
<221> NAME/KEY: MOD_RES
<222> LOCATION: (4)..(5)
<223> OTHER INFORMATION: Xaa is preferably Ala, Ser, Gly, Tyr, Pro or
      Gln

<400> SEQUENCE: 3

Gly Pro Gly Xaa Xaa
```

```
<210> SEQ ID NO 4
<211> LENGTH: 5
<212> TYPE: PRT
<213> ORGANISM: Araneus diadematus
<220> FEATURE:
<221> NAME/KEY: VARIANT
<222> LOCATION: (4)..(4)
<223> OTHER INFORMATION: Q at position 4 may also be alanine, serine,
      glycine, tyrosine, proline, or glutamine
<220> FEATURE:
<221> NAME/KEY: VARIANT
<222> LOCATION: (5)..(5)
<223> OTHER INFORMATION: Q at position 5 may also be alanine, serine,
      glycine, tyrosine, proline, or glutamine

<400> SEQUENCE: 4

Gly Pro Gly Gln Gln
1               5

<210> SEQ ID NO 5
<211> LENGTH: 5
<212> TYPE: PRT
<213> ORGANISM: Araneus diadematus
<220> FEATURE:
<221> NAME/KEY: REPEAT
<222> LOCATION: (1)..(5)
<223> OTHER INFORMATION: peptide motif (ADF-3)

<400> SEQUENCE: 5

Gly Pro Gly Ala Ser
1               5

<210> SEQ ID NO 6
<211> LENGTH: 5
<212> TYPE: PRT
<213> ORGANISM: Araneus diadematus
<220> FEATURE:
<221> NAME/KEY: REPEAT
<222> LOCATION: (1)..(5)
<223> OTHER INFORMATION: peptide motif (ADF-3)

<400> SEQUENCE: 6

Gly Pro Gly Ser Gly
1               5

<210> SEQ ID NO 7
<211> LENGTH: 5
<212> TYPE: PRT
<213> ORGANISM: Araneus diadematus
<220> FEATURE:
<221> NAME/KEY: REPEAT
<222> LOCATION: (1)..(5)
<223> OTHER INFORMATION: peptide motif (ADF-4)

<400> SEQUENCE: 7

Gly Pro Gly Gly Tyr
1               5

<210> SEQ ID NO 8
<211> LENGTH: 5
<212> TYPE: PRT
<213> ORGANISM: Araneus diadematus
<220> FEATURE:
<221> NAME/KEY: REPEAT
<222> LOCATION: (1)..(5)
<223> OTHER INFORMATION: peptide motif (ADF-4)

<400> SEQUENCE: 8
```

```
Gly Pro Gly Gly Pro
1               5

<210> SEQ ID NO 9
<211> LENGTH: 5
<212> TYPE: PRT
<213> ORGANISM: Nephila clavipes
<220> FEATURE:
<221> NAME/KEY: REPEAT
<222> LOCATION: (1)..(5)
<223> OTHER INFORMATION: peptide motif (flagelliform protein)

<400> SEQUENCE: 9

Gly Pro Gly Gly Ala
1               5

<210> SEQ ID NO 10
<211> LENGTH: 5
<212> TYPE: PRT
<213> ORGANISM: Unknown
<220> FEATURE:
<223> OTHER INFORMATION: Arthropoda
<220> FEATURE:
<221> NAME/KEY: REPEAT
<222> LOCATION: (1)..(5)
<223> OTHER INFORMATION: peptide motif (resilin)

<400> SEQUENCE: 10

Gly Pro Gly Gly Gly
1               5

<210> SEQ ID NO 11
<211> LENGTH: 5
<212> TYPE: PRT
<213> ORGANISM: Nephila clavipes
<220> FEATURE:
<221> NAME/KEY: REPEAT
<222> LOCATION: (1)..(5)
<223> OTHER INFORMATION: peptide motif (flagelliform protein)

<400> SEQUENCE: 11

Gly Pro Gly Gly Ser
1               5

<210> SEQ ID NO 12
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: REPEAT
<222> LOCATION: (1)..(5)
<223> OTHER INFORMATION: Ax peptide motif

<400> SEQUENCE: 12

Ala Ala Ala Ala Ala
1               5

<210> SEQ ID NO 13
<211> LENGTH: 6
<212> TYPE: PRT
<213> ORGANISM: Araneus diadematus
<220> FEATURE:
<221> NAME/KEY: REPEAT
<222> LOCATION: (1)..(6)
<223> OTHER INFORMATION: Ax peptide motif (ADF 3)

<400> SEQUENCE: 13
```

```
Ala Ala Ala Ala Ala Ala
1               5

<210> SEQ ID NO 14
<211> LENGTH: 7
<212> TYPE: PRT
<213> ORGANISM: Araneus diadematus
<220> FEATURE:
<221> NAME/KEY: REPEAT
<222> LOCATION: (1)..(7)
<223> OTHER INFORMATION: Ax peptide motif (ADF-4)

<400> SEQUENCE: 14

Ala Ala Ala Ala Ala Ala Ala
1               5

<210> SEQ ID NO 15
<211> LENGTH: 8
<212> TYPE: PRT
<213> ORGANISM: Araneus diadematus
<220> FEATURE:
<221> NAME/KEY: REPEAT
<222> LOCATION: (1)..(8)
<223> OTHER INFORMATION: Ax peptide motif (ADF-4)

<400> SEQUENCE: 15

Ala Ala Ala Ala Ala Ala Ala Ala
1               5

<210> SEQ ID NO 16
<211> LENGTH: 9
<212> TYPE: PRT
<213> ORGANISM: Artificial Sequence
<220> FEATURE:
<223> OTHER INFORMATION: synthetic
<220> FEATURE:
<221> NAME/KEY: REPEAT
<222> LOCATION: (1)..(9)
<223> OTHER INFORMATION: Ax peptide motif

<400> SEQUENCE: 16

Ala Ala Ala Ala Ala Ala Ala Ala Ala
1               5

<210> SEQ ID NO 17
<211> LENGTH: 10
<212> TYPE: PRT
<213> ORGANISM: Araneus diadematus
<220> FEATURE:
<221> NAME/KEY: REPEAT
<222> LOCATION: (1)..(10)
<223> OTHER INFORMATION: Ax peptide motif (ADF-4)

<400> SEQUENCE: 17

Ala Ala Ala Ala Ala Ala Ala Ala Ala Ala
1               5                   10

<210> SEQ ID NO 18
<211> LENGTH: 9
<212> TYPE: PRT
<213> ORGANISM: Unknown
<220> FEATURE:
<223> OTHER INFORMATION: Arthropoda
<220> FEATURE:
<221> NAME/KEY: REPEAT
<222> LOCATION: (1)..(9)
<223> OTHER INFORMATION: peptide motif (based on resilin)

<400> SEQUENCE: 18
```

```
Gly Gly Arg Pro Ser Asp Thr Tyr Gly
1               5

<210> SEQ ID NO 19
<211> LENGTH: 9
<212> TYPE: PRT
<213> ORGANISM: Unknown
<220> FEATURE:
<223> OTHER INFORMATION: Arthropoda
<220> FEATURE:
<221> NAME/KEY: REPEAT
<222> LOCATION: (1)..(9)
<223> OTHER INFORMATION: peptide motif (based on resilin)

<400> SEQUENCE: 19

Gly Gly Arg Pro Ser Ser Ser Tyr Gly
1               5

<210> SEQ ID NO 20
<211> LENGTH: 24
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(24)
<223> OTHER INFORMATION: Module A (ADF-3)

<400> SEQUENCE: 20

Gly Pro Tyr Gly Pro Gly Ala Ser Ala Ala Ala Ala Ala Ala Gly Gly
1               5                   10                  15

Tyr Gly Pro Gly Ser Gly Gln Gln
            20

<210> SEQ ID NO 21
<211> LENGTH: 35
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(35)
<223> OTHER INFORMATION: Module C (ADF-4)

<400> SEQUENCE: 21

Gly Ser Ser Ala Ala Ala Ala Ala Ala Ala Ala Ser Gly Pro Gly Gly
1               5                   10                  15

Tyr Gly Pro Glu Asn Gln Gly Pro Ser Gly Pro Gly Tyr Gly Pro
            20                  25                  30

Gly Gly Pro
        35

<210> SEQ ID NO 22
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(20)
<223> OTHER INFORMATION: Module Q (ADF-3)

<400> SEQUENCE: 22

Gly Pro Gly Gln Gln Gly Pro Gly Gln Gln Gly Pro Gly Gln Gln Gly
```

Pro Gly Gln Gln
            20

<210> SEQ ID NO 23
<211> LENGTH: 27
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(27)
<223> OTHER INFORMATION: Module K (flagelliform protein)

<400> SEQUENCE: 23

Gly Pro Gly Gly Ala Gly Gly Pro Tyr Gly Pro Gly Gly Ala Gly Gly
1               5                   10                  15

Pro Tyr Gly Pro Gly Gly Ala Gly Gly Pro Tyr
            20                  25

<210> SEQ ID NO 24
<211> LENGTH: 28
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(28)
<223> OTHER INFORMATION: Module sp (flagelliform protein)

<400> SEQUENCE: 24

Gly Gly Thr Thr Ile Ile Glu Asp Leu Asp Ile Thr Ile Asp Gly Ala
1               5                   10                  15

Asp Gly Pro Ile Thr Ile Ser Glu Glu Leu Thr Ile
            20                  25

<210> SEQ ID NO 25
<211> LENGTH: 34
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(34)
<223> OTHER INFORMATION: Module S (Resilin)

<400> SEQUENCE: 25

Pro Gly Ser Ser Ala Ala Ala Ala Ala Ala Ala Ser Gly Pro Gly
1               5                   10                  15

Gln Gly Gln Gly Gln Gly Gln Gly Gln Gly Gly Arg Pro Ser Asp Thr
            20                  25                  30

Tyr Gly

<210> SEQ ID NO 26
<211> LENGTH: 39
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(39)
<223> OTHER INFORMATION: Module R (Resilin)

-continued

```
<400> SEQUENCE: 26

Ser Ala Ala Ala Ala Ala Ala Ala Gly Pro Gly Gly Gly Asn Gly
1               5                   10                  15

Gly Arg Pro Ser Asp Thr Tyr Gly Ala Pro Gly Gly Gly Asn Gly Gly
                20                  25                  30

Arg Pro Ser Ser Ser Tyr Gly
            35

<210> SEQ ID NO 27
<211> LENGTH: 18
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(18)
<223> OTHER INFORMATION: Module X (flagelliform protein)

<400> SEQUENCE: 27

Gly Gly Ala Gly Gly Ala Gly Gly Ala Gly Gly Ser Gly Gly Ala Gly
1               5                   10                  15

Gly Ser

<210> SEQ ID NO 28
<211> LENGTH: 30
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(30)
<223> OTHER INFORMATION: Module Y (flagelliform protein)

<400> SEQUENCE: 28

Gly Pro Gly Gly Ala Gly Pro Gly Gly Tyr Gly Pro Gly Gly Ser Gly
1               5                   10                  15

Pro Gly Gly Tyr Gly Pro Gly Gly Ser Gly Pro Gly Gly Tyr
                20                  25                  30

<210> SEQ ID NO 29
<211> LENGTH: 24
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(24)
<223> OTHER INFORMATION: Module Ac

<400> SEQUENCE: 29

Gly Pro Tyr Gly Pro Gly Ala Ser Ala Ala Ala Ala Ala Ala Gly Gly
1               5                   10                  15

Tyr Gly Pro Gly Cys Gly Gln Gln
                20

<210> SEQ ID NO 30
<211> LENGTH: 24
<212> TYPE: PRT
<213> ORGANISM: Artificial Sequence
<220> FEATURE:
<223> OTHER INFORMATION: synthetic
<220> FEATURE:
<221> NAME/KEY: DOMAIN
```

```
<222> LOCATION: (1)..(24)
<223> OTHER INFORMATION: Module Ak

<400> SEQUENCE: 30

Gly Pro Tyr Gly Pro Gly Ala Ser Ala Ala Ala Ala Ala Gly Gly
1               5                   10                  15

Tyr Gly Pro Gly Lys Gly Gln Gln
            20

<210> SEQ ID NO 31
<211> LENGTH: 35
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(35)
<223> OTHER INFORMATION: Module Cc

<400> SEQUENCE: 31

Gly Ser Ser Ala Ala Ala Ala Ala Ala Ala Ser Gly Pro Gly Gly
1               5                   10                  15

Tyr Gly Pro Glu Asn Gln Gly Pro Cys Gly Pro Gly Tyr Gly Pro
            20                  25                  30

Gly Gly Pro
        35

<210> SEQ ID NO 32
<211> LENGTH: 35
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(35)
<223> OTHER INFORMATION: Module Ck1

<400> SEQUENCE: 32

Gly Ser Ser Ala Ala Ala Ala Ala Ala Ala Ser Gly Pro Gly Gly
1               5                   10                  15

Tyr Gly Pro Glu Asn Gln Gly Pro Lys Gly Pro Gly Tyr Gly Pro
            20                  25                  30

Gly Gly Pro
        35

<210> SEQ ID NO 33
<211> LENGTH: 35
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(35)
<223> OTHER INFORMATION: Module Ck2

<400> SEQUENCE: 33

Gly Ser Ser Ala Ala Ala Ala Ala Ala Ala Ser Gly Pro Gly Gly
1               5                   10                  15

Tyr Gly Pro Lys Asn Gln Gly Pro Ser Gly Pro Gly Tyr Gly Pro
            20                  25                  30

Gly Gly Pro
        35
```

```
<210> SEQ ID NO 34
<211> LENGTH: 35
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(35)
<223> OTHER INFORMATION: Module Ckc

<400> SEQUENCE: 34

Gly Ser Ser Ala Ala Ala Ala Ala Ala Ser Gly Pro Gly Gly
1               5                   10                  15

Tyr Gly Pro Lys Asn Gln Gly Pro Cys Gly Pro Gly Gly Tyr Gly Pro
            20                  25                  30

Gly Gly Pro
        35

<210> SEQ ID NO 35
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(13)
<223> OTHER INFORMATION: TAG cys1

<400> SEQUENCE: 35

Gly Cys Gly Gly Gly Gly Gly Gly Ser Gly Gly Gly Gly
1               5                   10

<210> SEQ ID NO 36
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(8)
<223> OTHER INFORMATION: TAG cys2

<400> SEQUENCE: 36

Gly Cys Gly Gly Gly Gly Gly Gly
1               5

<210> SEQ ID NO 37
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(14)
<223> OTHER INFORMATION: TAG cys3

<400> SEQUENCE: 37

Gly Cys Gly Gly Ser Gly Gly Gly Ser Gly Gly Gly Gly
1               5                   10

<210> SEQ ID NO 38
<211> LENGTH: 13
<212> TYPE: PRT
```

```
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(13)
<223> OTHER INFORMATION: TAG lys1

<400> SEQUENCE: 38

Gly Lys Gly Gly Gly Gly Gly Ser Gly Gly Gly Gly
1               5                   10

<210> SEQ ID NO 39
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(8)
<223> OTHER INFORMATION: TAG lys2

<400> SEQUENCE: 39

Gly Lys Gly Gly Gly Gly Gly Gly
1               5

<210> SEQ ID NO 40
<211> LENGTH: 5
<212> TYPE: PRT
<213> ORGANISM: Unknown
<220> FEATURE:
<223> OTHER INFORMATION: Arthropoda
<220> FEATURE:
<221> NAME/KEY: REPEAT
<222> LOCATION: (1)..(5)
<223> OTHER INFORMATION: peptide motif (resilin)

<400> SEQUENCE: 40

Gly Pro Gly Gln Gly
1               5

<210> SEQ ID NO 41
<211> LENGTH: 124
<212> TYPE: PRT
<213> ORGANISM: Artificial Sequence
<220> FEATURE:
<223> OTHER INFORMATION: based on ADF-3
<220> FEATURE:
<221> NAME/KEY: DOMAIN
<222> LOCATION: (1)..(124)
<223> OTHER INFORMATION: NR3 (ADF-3)

<400> SEQUENCE: 41

Gly Ala Ala Ser Ala Ala Val Ser Val Gly Gly Tyr Gly Pro Gln Ser
1               5                   10                  15

Ser Ser Ala Pro Val Ala Ser Ala Ala Ala Ser Arg Leu Ser Ser Pro
            20                  25                  30

Ala Ala Ser Ser Arg Val Ser Ser Ala Val Ser Ser Leu Val Ser Ser
        35                  40                  45

Gly Pro Thr Asn Gln Ala Ala Leu Ser Asn Thr Ile Ser Ser Val Val
    50                  55                  60

Ser Gln Val Ser Ala Ser Asn Pro Gly Leu Ser Gly Cys Asp Val Leu
65                  70                  75                  80

Val Gln Ala Leu Leu Glu Val Val Ser Ala Leu Val Ser Ile Leu Gly
                85                  90                  95
```

Ser Ser Ser Ile Gly Gln Ile Asn Tyr Gly Ala Ser Gln Tyr Thr
            100                 105                 110

Gln Met Val Gly Gln Ser Val Ala Gln Ala Leu Ala
        115                 120

<210> SEQ ID NO 42
<211> LENGTH: 109
<212> TYPE: PRT
<213> ORGANISM: Artificial Sequence
<220> FEATURE:
<223> OTHER INFORMATION: based on ADF-4
<220> FEATURE:
<221> NAME/KEY: DOMAIN
<222> LOCATION: (1)..(109)
<223> OTHER INFORMATION: NR4 (ADF-4)

<400> SEQUENCE: 42

Gly Ala Tyr Gly Pro Ser Pro Ser Ala Ser Ala Ser Val Ala Ala Ser
1               5                   10                  15

Arg Leu Ser Ser Pro Ala Ala Ser Ser Arg Val Ser Ser Ala Val Ser
            20                  25                  30

Ser Leu Val Ser Ser Gly Pro Thr Asn Gly Ala Ala Val Ser Gly Ala
        35                  40                  45

Leu Asn Ser Leu Val Ser Gln Ile Ser Ala Ser Asn Pro Gly Leu Ser
    50                  55                  60

Gly Cys Asp Ala Leu Val Gln Ala Leu Leu Glu Leu Val Ser Ala Leu
65                  70                  75                  80

Val Ala Ile Leu Ser Ser Ala Ser Ile Gly Gln Val Asn Val Ser Ser
                85                  90                  95

Val Ser Gln Ser Thr Gln Met Ile Ser Gln Ala Leu Ser
            100                 105

<210> SEQ ID NO 43
<211> LENGTH: 747
<212> TYPE: PRT
<213> ORGANISM: Araneus diadematus
<220> FEATURE:
<221> NAME/KEY: PEPTIDE
<222> LOCATION: (1)..(747)
<223> OTHER INFORMATION: MaSp I

<400> SEQUENCE: 43

Gln Gly Ala Gly Ala Ala Ala Ala Ala Ala Gly Gly Ala Gly Gln Gly
1               5                   10                  15

Gly Tyr Gly Gly Leu Gly Gly Gln Gly Ala Gly Gln Gly Gly Tyr Gly
            20                  25                  30

Gly Leu Gly Gly Gln Gly Ala Gly Gln Gly Gly Ala Gly Ala Ala Ala
        35                  40                  45

Ala Ala Ala Gly Gly Ala Gly Gln Gly Gly Tyr Gly Gly Leu Gly Ser
    50                  55                  60

Gln Gly Ala Gly Arg Gly Gly Gln Gly Ala Gly Ala Ala Ala Ala Ala
65                  70                  75                  80

Ala Gly Gly Ala Gly Gln Gly Gly Tyr Gly Gly Leu Gly Ser Gln Gly
                85                  90                  95

Ala Gly Arg Gly Gly Leu Gly Gly Gln Gly Ala Gly Ala Ala Ala Ala
            100                 105                 110

Ala Ala Ala Gly Gly Ala Gly Gln Gly Gly Tyr Gly Gly Leu Gly Asn
        115                 120                 125

Gln Gly Ala Gly Arg Gly Gly Gln Gly Ala Ala Ala Ala Ala Ala Gly
    130                 135                 140

```
Gly Ala Gly Gln Gly Gly Tyr Gly Gly Leu Gly Ser Gln Gly Ala Gly
145                 150                 155                 160

Arg Gly Gly Leu Gly Gly Gln Gly Ala Gly Ala Ala Ala Ala Ala Ala
                165                 170                 175

Gly Gly Ala Gly Gln Gly Gly Tyr Gly Gly Leu Gly Gly Gln Gly Ala
            180                 185                 190

Gly Gln Gly Gly Tyr Gly Gly Leu Gly Ser Gln Gly Ala Gly Arg Gly
        195                 200                 205

Gly Leu Gly Gly Gln Gly Ala Gly Ala Ala Ala Ala Ala Ala Ala Gly
    210                 215                 220

Gly Ala Gly Gln Gly Gly Leu Gly Gly Gln Gly Ala Gly Gln Gly Ala
225                 230                 235                 240

Gly Ala Ser Ala Ala Ala Ala Gly Gly Ala Gly Gln Gly Gly Tyr Gly
                245                 250                 255

Gly Leu Gly Ser Gln Gly Ala Gly Arg Gly Gly Glu Gly Ala Gly Ala
            260                 265                 270

Ala Ala Ala Ala Ala Gly Gly Ala Gly Gln Gly Gly Tyr Gly Gly Leu
        275                 280                 285

Gly Gly Gln Gly Ala Gly Gln Gly Gly Tyr Gly Gly Leu Gly Ser Gln
    290                 295                 300

Gly Ala Gly Arg Gly Gly Leu Gly Gly Gln Gly Ala Gly Ala Ala Ala
305                 310                 315                 320

Ala Gly Gly Ala Gly Gln Gly Gly Leu Gly Gly Gln Gly Ala Gly Gln
                325                 330                 335

Gly Ala Gly Ala Ala Ala Ala Ala Gly Gly Ala Gly Gln Gly Gly Gly
            340                 345                 350

Tyr Gly Gly Leu Gly Ser Gln Gly Ala Gly Arg Gly Gly Leu Gly Gly
        355                 360                 365

Gln Gly Ala Gly Ala Val Ala Ala Ala Ala Gly Gly Ala Gly Gly Gln
    370                 375                 380

Gly Gly Tyr Gly Gly Leu Gly Ser Gln Gly Ala Gly Arg Gly Gly Gln
385                 390                 395                 400

Gly Ala Gly Ala Ala Ala Ala Ala Ala Gly Gly Ala Gly Gln Arg Gly
                405                 410                 415

Tyr Gly Gly Leu Gly Asn Gln Gly Ala Gly Arg Gly Gly Leu Gly Gly
            420                 425                 430

Gln Gly Ala Gly Ala Ala Ala Ala Ala Ala Gly Gly Ala Gly Gly Gln
        435                 440                 445

Gly Gly Tyr Gly Gly Leu Gly Asn Gln Gly Ala Gly Arg Gly Gly Gln
    450                 455                 460

Gly Ala Ala Ala Ala Ala Gly Gly Ala Gly Gln Gly Gly Tyr Gly Gly
465                 470                 475                 480

Leu Gly Ser Gln Gly Ala Gly Arg Gly Gly Gln Gly Ala Gly Ala Ala
                485                 490                 495

Ala Ala Ala Ala Val Gly Ala Gly Gln Glu Gly Ile Arg Gly Gln Gly
            500                 505                 510

Ala Gly Gln Gly Gly Tyr Gly Gly Leu Gly Ser Gln Gly Ser Gly Arg
        515                 520                 525

Gly Gly Leu Gly Gly Gln Gly Ala Gly Ala Ala Ala Ala Ala Ala Gly
    530                 535                 540

Gly Ala Gly Gln Gly Gly Leu Gly Gly Gln Gly Ala Gly Gln Gly Ala
545                 550                 555                 560
```

Gly Ala Ala Ala Ala Ala Gly Gly Val Arg Gln Gly Gly Tyr Gly
              565                 570                 575

Gly Leu Gly Ser Gln Gly Ala Gly Gly Gln Gly Ala Gly Ala
        580                 585                 590

Ala Ala Ala Ala Gly Gly Ala Gly Gln Gly Gly Tyr Gly Gly Leu
        595                 600                 605

Gly Gly Gln Gly Val Gly Arg Gly Gly Leu Gly Gly Gln Ala Gly
    610                 615                 620

Ala Ala Ala Gly Ala Gly Gln Gly Gly Tyr Gly Gly Val Gly
625                 630                 635                 640

Ser Gly Ala Ser Ala Ala Ser Ala Ala Ala Ser Arg Leu Ser Ser Pro
                645                 650                 655

Gln Ala Ser Ser Arg Val Ser Ser Ala Val Ser Asn Leu Val Ala Ser
            660                 665                 670

Gly Pro Thr Asn Ser Ala Ala Leu Ser Ser Thr Ile Ser Asn Val Val
        675                 680                 685

Ser Gln Ile Gly Ala Ser Asn Pro Gly Leu Ser Gly Cys Asp Val Leu
    690                 695                 700

Ile Gln Ala Leu Leu Glu Val Val Ser Ala Leu Ile Gln Ile Leu Gly
705                 710                 715                 720

Ser Ser Ser Ile Gly Gln Val Asn Tyr Gly Ser Ala Gly Gln Ala Thr
                725                 730                 735

Gln Ile Val Gly Gln Ser Val Tyr Gln Ala Leu
            740                 745

<210> SEQ ID NO 44
<211> LENGTH: 627
<212> TYPE: PRT
<213> ORGANISM: Araneus diadematus
<220> FEATURE:
<221> NAME/KEY: PEPTIDE
<222> LOCATION: (1)..(627)
<223> OTHER INFORMATION: MaSp II

<400> SEQUENCE: 44

Pro Gly Gly Tyr Gly Pro Gly Gln Gln Gly Pro Gly Gly Tyr Gly Pro
1               5                   10                  15

Gly Gln Gln Gly Pro Ser Gly Pro Gly Ser Ala Ala Ala Ala Ala
            20                  25                  30

Ala Ala Ala Ala Gly Pro Gly Gly Tyr Gly Pro Gly Gln Gln Gly Pro
        35                  40                  45

Gly Gly Tyr Gly Pro Gly Gln Gln Gly Pro Gly Arg Tyr Gly Pro Gly
    50                  55                  60

Gln Gln Gly Pro Ser Gly Pro Gly Ser Ala Ala Ala Ala Ala Gly
65                  70                  75                  80

Ser Gly Gln Gln Gly Pro Gly Gly Tyr Gly Pro Arg Gln Gln Gly Pro
                85                  90                  95

Gly Gly Tyr Gly Gln Gln Gly Pro Ser Gly Pro Gly Ser Ala
            100                 105                 110

Ala Ala Ala Ser Ala Ala Ala Ser Ala Glu Ser Gly Gln Gln Gly Pro
        115                 120                 125

Gly Gly Tyr Gly Pro Gly Gln Gln Gly Pro Gly Gly Tyr Gly Pro Gly
    130                 135                 140

Gln Gln Gly Pro Gly Gly Tyr Gly Pro Gly Gln Gln Gly Pro Ser Gly
145                 150                 155                 160

Pro Gly Ser Ala Ala Ala Ala Ala Ala Ala Ala Ser Gly Pro Gly Gln

```
                    165                 170                 175
Gln Gly Pro Gly Gly Tyr Gly Pro Gly Gln Gln Gly Pro Gly Gly Tyr
                180                 185                 190

Gly Pro Gly Gln Gln Gly Pro Ser Gly Pro Gly Ser Ala Ala Ala Ala
            195                 200                 205

Ala Ala Ala Ala Ser Gly Pro Gly Gln Gln Gly Pro Gly Gly Tyr Gly
        210                 215                 220

Pro Gly Gln Gln Gly Pro Gly Gly Tyr Gly Pro Gly Gln Gln Gly Leu
225                 230                 235                 240

Ser Gly Pro Gly Ser Ala Ala Ala Ala Ala Ala Gly Pro Gly Gln
            245                 250                 255

Gln Gly Pro Gly Gly Tyr Gly Pro Gly Gln Gln Gly Pro Ser Gly Pro
        260                 265                 270

Gly Ser Ala Ala Ala Ala Ala Ala Ala Ala Gly Pro Gly Gly Tyr
            275                 280                 285

Gly Pro Gly Gln Gln Gly Pro Gly Gly Tyr Gly Pro Gly Gln Gln Gly
        290                 295                 300

Pro Ser Gly Ala Gly Ser Ala Ala Ala Ala Ala Ala Gly Pro Gly
305                 310                 315                 320

Gln Gln Gly Leu Gly Gly Tyr Gly Pro Gly Gln Gln Gly Pro Gly Gly
            325                 330                 335

Tyr Gly Pro Gly Gln Gln Gly Pro Gly Gly Tyr Gly Pro Gly Ser Ala
        340                 345                 350

Ser Ala Ala Ala Ala Ala Ala Gly Pro Gly Gln Gln Gly Pro Gly Gly
        355                 360                 365

Tyr Gly Pro Gly Gln Gln Gly Pro Ser Gly Pro Gly Ser Ala Ser Ala
        370                 375                 380

Ala Ala Ala Ala Ala Ala Gly Pro Gly Gly Tyr Gly Pro Gly Gln
385                 390                 395                 400

Gln Gly Pro Gly Gly Tyr Ala Pro Gly Gln Gln Gly Pro Ser Gly Pro
            405                 410                 415

Gly Ser Ala Ser Ala Ala Ala Ala Ala Ala Ala Gly Pro Gly Gly
            420                 425                 430

Tyr Gly Pro Gly Gln Gln Gly Pro Gly Gly Tyr Ala Pro Gly Gln Gln
        435                 440                 445

Gly Pro Ser Gly Pro Gly Ser Ala Ala Ala Ala Ala Ala Ala Ala
        450                 455                 460

Gly Pro Gly Gly Tyr Gly Pro Ala Gln Gln Gly Pro Ser Gly Pro Gly
465                 470                 475                 480

Ile Ala Ala Ser Ala Ala Ser Ala Gly Pro Gly Gly Tyr Gly Pro Ala
            485                 490                 495

Gln Gln Gly Pro Ala Gly Tyr Gly Pro Gly Ser Ala Val Ala Ala Ser
        500                 505                 510

Ala Gly Ala Gly Ser Ala Gly Tyr Gly Pro Gly Ser Gln Ala Ser Ala
        515                 520                 525

Ala Ala Ser Arg Leu Ala Ser Pro Asp Ser Gly Ala Arg Val Ala Ser
        530                 535                 540

Ala Val Ser Asn Leu Val Ser Ser Gly Pro Thr Ser Ser Ala Ala Leu
545                 550                 555                 560

Ser Ser Val Ile Ser Asn Ala Val Ser Gln Ile Gly Ala Ser Asn Pro
            565                 570                 575

Gly Leu Ser Gly Cys Asp Val Leu Ile Gln Ala Leu Leu Glu Ile Val
        580                 585                 590
```

```
Ser Ala Cys Val Thr Ile Leu Ser Ser Ser Ile Gly Gln Val Asn
        595                 600                 605

Tyr Gly Ala Ala Ser Gln Phe Ala Gln Val Val Gly Gln Ser Val Leu
        610                 615                 620

Ser Ala Phe
625
```